(12) United States Patent
Philip et al.

(10) Patent No.: US 7,173,002 B2
(45) Date of Patent: Feb. 6, 2007

(54) 150 KDA TGF-B1 ACCESSORY RECEPTOR ACTS A NEGATIVE MODULATOR OF TGF-B SIGNALING

(75) Inventors: Anie Philip, Montreal (CA); Betty Tam, Ville St. Laurent (CA)

(73) Assignee: McGill University, Montreal (CA)

( * ) Notice: Subject to any disclaimer, the term of this patent is extended or adjusted under 35 U.S.C. 154(b) by 48 days.

(21) Appl. No.: 10/475,711

(22) PCT Filed: Apr. 24, 2002

(86) PCT No.: PCT/CA02/00560

§ 371 (c)(1),
(2), (4) Date: May 13, 2004

(87) PCT Pub. No.: WO02/085942

PCT Pub. Date: Oct. 31, 2002

(65) Prior Publication Data

US 2004/0191860 A1    Sep. 30, 2004

Related U.S. Application Data

(60) Provisional application No. 60/356,163, filed on Feb. 14, 2002, provisional application No. 60/285,713, filed on Apr. 24, 2001.

(51) Int. Cl.
| | |
|---|---|
| A01N 37/18 | (2006.01) |
| A61K 39/00 | (2006.01) |
| A61K 35/12 | (2006.01) |
| G01N 33/53 | (2006.01) |
| C07K 14/00 | (2006.01) |

(52) U.S. Cl. .................. 514/2; 424/520; 424/185.1; 435/7.1; 530/300; 530/350

(58) Field of Classification Search .................. None
See application file for complete search history.

(56) References Cited

FOREIGN PATENT DOCUMENTS

| WO | WO 00/29448 | * | 5/2000 |
| WO | WO 02/070696 | | 9/2002 |

OTHER PUBLICATIONS

Lastres et al. 1996. J Cell Biol. 133:1109-1121.*
Li et al. 1999. FASEB J. 14:55-64.*
Onichtchouk et al. 1999. Nature. 401:480-485.*
Abrami, L. et al., The Journal of Biological Chemistry, 2001, vol. 276, No. 33, pp. 30729-30736.
Akhurst, R.J. et al., TRENDS in Cell Biology, 2001, vol. 11, No. 11, pp. S44-S51.
Blacker, D. et al., Nature America Inc., 1998. vol. 19, pp. 357-360.
Blobe, G.C. et al., The New England Journal of Medicine, 2000. vol. 342, pp. 1350-1358.
Border, W.A. et al., Letters to Nature—Nature Publishing Group, 1990. vol. 346, pp. 371-374.
Bordier, C., The Journal of Biological Chemistry, 1981, vol. 256, No. 4, pp. 1604-1607.
Boukamp, P. et al., The Journal of Cell Biology, 1988, vol. 106, pp. 761-771.
Boyd, F.T. et al., The Journal of Biological Chemistry, 1989, vol. 264, No. 4, pp. 2272-2278.
Broomfield, S.J. et al., Biochimica et Biophysica Acta, 1993, 1145, pp. 212-218.
Brown, D., Current Opinion in Immunolgy-Current Biology Ltd, 1993, vol. 5, pp. 349-354.
Brown, D.A. et al., Annu. Rev. Cell Dev. Biol., 1998, 14, pp. 111-136.
Chajek-Shaul, T. et al., Biochimica et Biophysica Acta, 1989, 1014, pp. 178-183.
Charng, M-J. et al., The Journal of Biological Chemistry, 1998, vol. 273, No. 16, pp. 9365-9368.
Cheifetz, S. et al., The Journal of Biological Chemistry, 1991, vol. 226, No. 31, pp. 20767-20772.
Cheifetz, S. et al., The Journal of Biological Chemistry, 1992, vol. 267, No. 27, pp. 19027-19030.

(Continued)

*Primary Examiner*—Lorraine Spector
*Assistant Examiner*—Shulamith H. Shafer
(74) *Attorney, Agent, or Firm*—Goudreau Gage Dubuc

(57) ABSTRACT

The present invention relates to a TGF-β1 binding protein called r150. This protein has a GPI-anchor contained in r150 itself and not on a tightly associated protein and that it binds TGF-β1 with an affinity comparable to those of the signaling receptors. Furthermore, the released (soluble) form of this protein binds TGF-β1 independent of the types I and II receptors. Also, the soluble form inhibits the binding of TGF-β to its receptor. In addition, evidence that r150 is released from the cell surface by an endogenous phospholipase C is provided. Also, the creation of a mutant human keratinocyte cell line with a defect in GPI synthesis which displays reduced expression of r150 is described. Our results using these mutant keratinocytes suggest that the membrane anchored form of r150 is a negative modulator of TGF-beta responses. These findings, taken together with the observation that r150 forms a heteromeric complex with the signaling receptors, suggest that this accessory receptor in either its membrane anchored or soluble form may antagonize TGF-β responses in human keratinocytes. Experiments with mutants confirmed that TGFβ1 activity can be modulated when the expression of the accessory receptor r150 is silenced. The complete nucleic acid and deduced amino acid sequences are now provided. The r150 cloned nucleic acid was used to study overexpression of r150. When r150 gene is overexpressed, TGFβ responses are increased. r150 and its derivatives or precursors (fragments, variants and nucleic acids encoding the same) will find a broad clinical utility, knowing that TGFβ1 is an important cytokine.

2 Claims, 24 Drawing Sheets

OTHER PUBLICATIONS

Chen, R. et al., Proc. Natl. Acad. Sci. USA, 1998, vol. 95, pp. 9512-9517.
Chen, R-H. et al., Letters to Nature—Nature, 1995, vol. 377, pp. 548-552.
Chen, Y-G. et al., The EMBO Journal, 1997, vol. 16, No. 13, pp. 3866-3876.
Choi, B-M. et al., Immunology and Cell Biology, 1996, 74, pp. 144-150.
Choi, M-E., American Physiological Society, 1999, 276, pp. F88-F95.
Choy, L. et al., The Journal of Biological Chemistry, 1998, vol. 273, No. 47, pp. 31455-31462.
Clark, R.A.F., The Molecular and Cellular Biology of Wound Repair, Second Edition, Plenum Press, 1996, pp. 3-35.
Datta, P.K. et al., The Journal of Biological Chemistry, 1998, vol. 273. No. 52. pp. 34671-34674.
Datta, P. K. et al., Molecular and Cellular Biology, 2000, vol. 20, No. 9, pp. 3157-3167.
Draper, L.B. et al., The Journal of Biological Chemistry, 1998, vol. 271, No. 1, pp. 398-403.
Dumont, N. et al., Molecular and Cellular Endocrinology, 1995, 111, pp. 57-66.
Germain, L. et al., Burns, 1993, 19, (2), pp. 99-104.
Glick, A.B. et al., Proc. Natl. Acad. Sci. USA, 1993, vol. 90, pp. 6076-6080.
Glick, A.B. et al., Genes & Development, 1994, vol. 8, pp. 2429-2440, only abstract provided.
Gonias, S.L. et al., The Journal of Biological Chemistry, 2000, vol. 275, No. 8, pp. 5826-5831.
Gougos, A. et al., The Journal of Biological Chemistry, 1990, vol. 265, No. 15, pp. 8361-8364.
Grainger, D.J, et al., Biol. Rev., 1995, 70, pp. 571-596.
Gressner, A.M. et al., Frontiers in Bioscience 7, 2002, d793-807.
Griswold-Penner, I. et al., Molecular and Cellular Biology, 1998. pp. 6595-6604.
Hebda, P.A., The Journal of Investigative Dermatology, vol. 91, No. 5, pp. 440-445.
Heldin, C.H. et al., Nature, 1997, vol. 390, pp. 465-471.
Hojo, M. et al., Nature, 1999, vol. 397, pp. 530-534.
Hooper, N.M., Identification of glycosyl-phosphatidylinositol . . . In Hooper NM and Turner AJ, 1995, A Practical Approach. 1NY: IRL Press. pp. 89-115.
Hooper, N.M., Mol Membr Biol, 1999, 16 (2), pp. 145-156, abstract only.
Horejse, V. et al., Viewpoint Immunology Today, 1999, vol. 20, No. 8, pp. 356-361.
Huse, M. et al., Cell, 1999, vol. 96, pp. 425-436.
Isaka, Y. et al., Nature Medicine, 1996, vol. 2, pp. 418-423.
Isaka, Y. et al., Kidney International, 1999, vol. 55, pp. 465-475.
Kawabata, M. et al., The Journal of Biological Chemistry, 1995, vol. 270, No. 50, pp. 29628-29631.
Khalil, N. et al., Ciba Found Symp. 1991, 157, pp. 194-207, abstract only.
Kingsley, D.M., Genes & Development, 1994, 8, pp. 133-146.
Kirsch, T. et al., Physiologische Chemie II—FEBS Letters 468, 2000, pp. 215-219.
Laiho, M. et al., The Journal of Biological Chemistry, 1990, vol. 265, No. 30, pp. 18518-18524.
Lefer, A.M. et al., Proc. Natl. Acad. Sci USA, Physiology, 1993, vol. 90, pp. 1018-1022.
Lefer, A.M. et al., Science, 1990, vol. 249, 4964, Research Library Core, pp. 61-64.
Letamendia, A. et al., The Journal of Biological Chemistry, 1998, vol. 273, No. 49, pp. 33011-33019.
Letterio, J.J. et al., Annu. Rev. Immunol., 1998, 16, pp. 137-161.
Li, C. et al., The FASEB Journal, 2000, vol. 14, pp. 55-64.
Lin, M. et al., BLOOD, 2002, vol. 99, No. 5, pp. 1683-1691.
Lisanti, M.P. et al., The Journal of Cell Biology, 1994, vol. 126, No. 1, pp. 111-126.
Lisanti, M.P. et al., Proc. Natl. Acad. Sci. USA, 1988, vol. 85, pp. 9557-9561.
Liu, J. et al., The Journal of Biological Chemistry, 1997, vol. 272, No. 11, pp. 7211-7222.
Lopez-Casillas, F. et al., The Journal of Cell Biology, 1994, vol. 124, No. 4, pp. 557-568.
Lopez-Casillas, F. et al., Cell, 1993, 73(7), pp. 1435-1444, Abstract only.
Luo, K. et al., The EMBO Journal, 1997, vol. 16, No. 8, pp. 1970-1981.
Markowitz, S. et al., Science, 1995, 268, 5215, pp. 1336-1338.
Massagué, J., Annu. Rev. Biochem. 1998, 67 pp. 753-791.
Massagué, J. et al., Cell, 2000, vol. 103, pp. 295-309.
McCaffrey, T.A., Cytokine & Growth Factor Reviews 11, 2000, 103-114.
McNeill, H. et al., Clinical Neuroscience and Neuropathology, 1994, NeuroReport 5, pp. 901-904.
Mehta, J.L. et al., Growth Factors, 1999, vol. 16, pp. 179-190.
Metz, C.N. et al., The EMBO Journal, 1994, vol. 13, No. 7, pp. 1741-1751.
Moulin, V. et al., 1997, Journal of Cellular Physiology, 171, pp. 1-10.
Movahedi, S. et al., Biochem. J., 1997, 326, pp. 531-537.
Mustoe, T.A. et al., Science, 1987, vol. 237, pp. 1333-1336.
Neer, E.J. et al., Nature, 1994, vol. 371, pp. 297-300.
Nosjean, O. et al., Biochimica et Biophysica Acta, 1997, 1331, pp. 153-186.
Nunes, I. et al., Cancer Research 56, 1997, pp. 495-499.
Oka, N. et al., The Journal of Biological Chemistry, 1997, vol. 272, No. 52, pp. 33416-33421.
Onichtchouk, D. et al., Nature, 1999, vol. 401, pp. 480-485.
Pasch, M.C. et al., The Society for Investigative Dermatology, Inc. , 1998, vol. 111, pp. 683-688.
Patel, B.N. et al., The Journal of Biological Chemistry, 1997, vol. 272, No. 32, pp. 20185-20190.
Peltonen, J. et al., J Invest Dermatol. 1991, 97(2), pp. 240-248, abstract only.
Pepin, M-C. et al., Proc. Natl. Acad. Sci., 1994, vol. 91, pp. 6997-7001.
Philip, A. et al., The Journal of Biological Chemistry, 1991, vol. 266, No. 33, pp. 22290-22296.
Philip, A. et al., Eur. J. Biochem., 1999, 261, pp. 618-628.
Pietenpol, J.A. et al., Proc. Natl. Acad. Sci., 1990, vol. 87, pp. 3758-3762.
Razani, B. et al., The Journal of Biological Chemistry, 2001, vol. 276, No. 9, pp. 6727-6738.
Roberts, A.B. et al., The Transforming Growth Factor-βs. Peptide Growth Factors and their Receptors I. NY: Springer-Verlag., 1990, pp. 419-472.
Roberts, A.B. et al., Transforming Growth Factor β., 196, In: The Molecular & Cellular Biology of Wound Repair (2nd ed.), Clark, R.A.F. (ed), Plenum Press, NY, pp. 275-308.
Rodriguez-Boulan, E. et al., Annu. Rev. Cell Biol., 1992, 8, pp. 395-427.
Rosen, C.L. et al., The Journal of Cell Biology, 1992, vol. 117, No. 3, pp. 617-627.
Saltiel, A.R., Invited Review, 1996, Diverse signaling pathways in the cellular actions of insulin. Am. J. Physiol., 270, pp. E375-E382.
Sambamurti, K. et al., The Journal of Biological Chemistry, 1999, vol. 274, No., 38, pp. 26810-26814.
Sargiacomo, M. et al., The Journal of Cell Biology, 1993, vol. 122, No. 4, pp. 789-807.
Schuh, A.C. et al., The American Society of Hematology, BLOOD, 2002, vol. 99, No. 5, pp. 1692-1698.
Screaton, R.A. et al., The Journal of Cell Biology, 2000, vol. 150, No. 3, pp. 613-625.
Sega, G.A., Mutation Research, 1984, 134, pp. 113-142.
Sellheyer, K. et al., Proc. Natl. Acad. Sci. USA., 1993, vol. 90, pp. 5237-5241.
Shah, M. et al., Journal of Cell Science, 1995, vol. 108, pp. 985-1002.
Sheppard, D., Chest, 2001, 120, 1 Supplement, pp. 49S-53S.
Shukla, S.D., Life Sciences, 1982, vol. 30, pp. 1323-1355.

Stevens, V.L., Selection of Mammalian Cell Mutants in GPI Biosynthesis, Methods in Molecular Biology, 1999, vol. 116, pp. 13-22.

Stevens, V.L. et al., Biochem. J., 1996, 313, pp. 253-258.

Taheri, M. et al., The Journal of Biological Chemistry, 2000, vol. 275, No. 35, pp. 26935-26943.

Tam, B.B.Y. et al., Journal of Cellular Biochemistry, 2001, vol. 83, pp. 494-507.

Tam, B.Y.Y. et al., Journal of Cellular Biochemistry, 1998, vol. 70, pp. 573-586, ABST.

Tam, B.Y.Y. et al., Journal of Cellular Physiology, vol. 176, pp. 553-564.

Tarutani, M. et al., Proc. Natl. Acad. Sci. USA, 1997, vol. 94, pp. 7400-7405.

Tsukazaki, T. et al., Cell, 1998, vol. 95, pp. 779-791.

Turner, A.J., PIG-tailed membrane proteins. Essays in Biochem, 1994, 28, pp. 113-127.

Venneker, G. et al., Journal of Pathology, 1994, vol. 172, pp. 189-197.

Wang, X.J. et al., Proc. Natl. Acad. Sci. USA, vol. 94, pp. 2386-2391.

Wang, T. et al., Cell, 1996, vol. 86, pp. 435-444.

Webb, D.J. et al., Protein Science, 2000, vol. 9, pp. 1986-1992.

Webb, D.J. et al., The Journal of Biological Chemistry, 1998, vol. 273, No. 21, pp. 13339-13346.

Welch, D.R. et al., Proc. Natl. Acad. Sci. USA, vol. 87, pp. 7678-7682.

Wieser, R. et al., The EMBO Journal, 1995, vol. 14, pp. 2199-2208.

Wong, S.H. et al., Eur. J. Biochem., 2000, 267, pp. 5550-5560.

Wrana, J. L. et al., Nature, 1994, vol. 370, pp. 341-347.

Wrana, J.L. et al., Cell, 1992, vol. 71, pp. 1003-1014.

Wrana, J.L. et al., Cytokine & Growth Factor Reviews 11, 2000, pp. 5-13.

Wurthner, J.U. et al., The Journal of Biological Chemistry, 2001, vol. 276, No. 22, pp. 19495-19502.

Xie, M. et al., The American Physiological Society, 1993, 265, pp. C1156-C1166.

Yamamoto, T. et al., Kidney International, 1994, vol. 45, pp. 916-927.

Yamamoto, T. et al., Clinical Immunology, 1999, vol. 92, No. 1, pp. 6-13.

Yamashita, H. et al., The Journal of Biological Chemistry, 1994, vol. 269, No. 3, pp. 1995-2001.

Yin, J.J. et al., The Journal of Clinical Investigation, 1999, vol. 103, No. 2, pp. 197-206.

Zaccaro, M.C. et al., The Journal of Biological Chemistry, 2001, vol. 276, No. 33, pp. 31023-31029.

Zambruno, G. et al., The Journal of Cell Biology, 1995, vol. 129, No. 3, pp. 853-865.

Zamze, S.E. et al., Eur. J. Biochem., 1998, 176, pp. 527-534.

O'Kane, S. et al., Int. J. Biochem. Cell Biol. 1997, vol. 29(1):63-78.

\* cited by examiner

Schematic diagram representing the cloned sequence of the r150 protein.

Expression of the cloned gene in HaCaT cells demonstrates that it represents r150. The expressed protein migrates at 150 kDa on SDS-PAGE and is detectable by an antibody (anti-CRD antibody) which detects GPI-anchor.

```
2206        acaactactccagtggagctccaagccttccaaccattttcattttttgaatcttcctactctgttatcagaggtgaagaattgcttggaaataactata  2310
(736)        T  T  P  V  G  L  G  A  P  G  P  P  P  I  P  L  A  L  P  T  S  V  I  A  G  G  P  A  L  G  I  T  I   (770)
2311        ttcaattatttgaaagatgccactgaggttaaggttaatcattgagaaaagtgacaaatttgatattccaatgaataaatgccacaggccaccag         2415
(771)        P  A  I  L  A  A  T  G  V  L  V  I  I  G  L  S  A L P A I L M T S A G I A T G H G                     (805)
2416        cagaccctctgttcccagtggagatgggcaactgctgttcttccatcagccaacacatctggagaaattcctatcacagtcacgctcttcaccact       2520
(806)        G  T  L  L  V  P  S  G  A  G  A  T  V  L  P  P  I  A  P  T  H  L  G  G  I  P  I  T  V  T  A  L  S  P  T  (840)
2521        gcttctgatgctgtcaccagtggcatgattttagtaaaggctgaaggaataagaaaatcatattcacaatccatcttattagacttgactgacaataggctacagagt (2625)
(841)        A  S  A  A  V  T  G  M  I  L  V  L  A  G  G  I  G  L  S  T  S  G  S  I  L  L  A  L  T  A  A  A  L  G  S     (875)
2626        accctgaaaacttgagtttctcattccctcctaatacagtgactgcagtgaaagagttcagatcactgcaattggatgatgtcctcatcaatggc      2730
(876)        T  L  T  L  S  P  S  P  P  P  A  A  T  V  G  S  A  V  G  I  T  A  I  G  A  V  L  G  P  S  I  A  G         (910)
2731        ttagcctcattgattggatcgcttatgccttatgccttatgcttagggaaccaatgatgatatttgctccaaatattacatttggatatatctgactaaaagaaacaactg  2835
(911)        L  A  S  L  I  A  M P T G C G G   A  M  I  A  P  A  I  T  I  L  A  T  L  T  L  L  G  L               (945)
2836        acagataatttgaaagaaaaagctcttcattatggagcaaggtacagagaagaacttcagtgctctttcagttgggaattat                      2940
(946)        T  A  A  L  G  L  A  L  S  P  M  A  G  G  T  G  A  G  L  L  T  G  A  G  S  P  S  A  P  G  A  T         (980)
2941        gaccctctgggagcacttggttgtcagctttgttcttaagatgtttcttgaagccgatcattgatcagaatgttacacagaacatacact              3045
(981)        A  P  S  G  T  L  S  A  P  V  L  A  C  P  L  G  A  A  P  T  I  A  I  A  G  A  V  L  H  T  T            (1015)
3046        tggcttaaggacatcaagaatccaacgcgttgaattttggattcatgtgagctP G A V I H S G L G G G A L S P V L T A             3150
(1016)        T  L  I  G  H  G  L  S  A  G  G  P  T  A  (1050)
3151        tatattgtaactctctcctgggatataagaaagtgatgcgtcaagatgtgcaagaggtctatccattttgagtctgaattcagtagaggaatttcagac  3255
(1051)        T  I  V  T  S  L  I  G  T  A  L  T  G  P  A  I  A  V  G  G  S  I  H  P  L  G  S  G  P  S  A  G  I  S  A  (1085)
3256        aattatactctagccctataactatgcattgtcatcagtgggagtcctaaagcgaaggaagtttgaatatgctgacttggagagcagaacaagaaggtggc 3360
(1086)       A T T  L  A  L  I  T  T  A  L  S  S  V  G  S  P  L  A  I  G  A  L  A  M  L  T  T  A  A  G  G  G  G  (1120)
```

FIGURE 17 (CONT.)

```
3361  atgcaattctgggtgtcatcagagtccaaacttctgactcctggcagccacgctcctgatatgaagttgcagccatgcactgctcacttcttacaa  3465
(1121) M  Q  F  W  V  S  S  E  S  Q  T  S  D  S  W  Q  P  R  L  Q  V  A  A  T  A  L  L  S  H  P  L  G  (1155)
3466  tttcagacttctgagggaatccaattatgagggtggctaagcaggcaaagaataagcttggtgtttgcatctactcaggatacactgtggctttaaaggct  3570
(1156) F  Q  T  S  E  G  S  S  L  L  S  A  S  T  G  P  A  S  L  G  V  C  I  Y  S  G  Y  T  V  A  L  K  A  (1190)
3571  ctgtctgaattgcagcctaatgaatacagaaaggacaaatatccaagtcctagctccaccaagtcctgtaaagttctgattgacacacac  3675
(1191) L  S  G  I  A  A  N  E  Y  R  K  D  K  Y  P  S  P  S  S  T  K  S  C  K  V  L  I  D  T  H  (1225)
3676  aaccgcttactcctcagacagcagcttgctctgtgtacagccaatggttttggattgtcagctcaatgttgta  3780
(1226) N  R  L  L  L  R  Q  Q  L  A  L  C  T  A  N  G  F  G  L  S  A  Q  C  C  (1260)
```

```
                           tttattttttaaaggactctgtgtaacactaacatttccagtagtcacatgtgattgttttgttttcgtagaa     4410
4339 gaatactgctctatttgaaaaaagagtttttttctttctcatgggttgcagggatggtgtacaacaggtcctagcatgtatagctgcatagattcttcacc     4515
4411 tgatctttgtgtggaagatcagaatgaatgcagttgtgtgctctatatttccctcacaaatctttagaattttttggagtgttgttttctccagaataa     4620
4516 aggtattacttttagaa                                                                                        4636
4521 ----------------
                           taggtattctcctcatttttgtgaaagaaatgaacctagatctttaagcattattacacatccatgtttgcttaaagatgattccct     4725
4637 ggggaatgggagaaaacagccagcaggaggagcttcatcgtgttcctcccttccaacctagcctccaacctgccaaccccaccaccatgccagtgg     4830
4726 tctcagtagaafacttcttaactgaatcttcttttcagatctagtggtgtgtcagtcagtacattactgtgctttcacaccatctcagaggtgaggagcatactgaaa     4935
4831 cccagccattgcccctccctctcttttctctgtagagaaatgtgagggcagtacatcctcagcctccacatcccacactcccacagtctctatttcaggggtgagagtcagagagcactgcaatatgtgcttc     5040
4936 attgccctggggtgctgtgtgtcttcgaagatcctagagcaggagagatcctagagcaggatacaacaaatactaggtaagtcactgcagaccgacctccctgcagtttggga     5145
5041 atgggattcgattcgaagatcctagagcaggagagatcctagagcaggatacaacaaatactaggtaagtcactgcagaccgacctccctgcagtttggga     5250
5146 aagaagctgggtttgtggagaatcagagcatctgacatgagcatctgacatgagcatctgaagaacctcttctagttcagggt     5355
5251 gtgagcattagaactgccagttgtctagtgacatgctgctgctgtgacttgaactttaagatgaactcttttcaatcctgagccgtatttccga     5460
5356 aggtaatataattatctgatgaatttaaagatgaaattttcaacaattaatgatctttattcaatctaagaaatggttagttttctcttttagctctatgcattcactcaagtggac     5565
5461 tactgaaatgattatagatatgtcaacaattaatgatctttattcaatctaagaaatggttagttttctcttttagctctatgcattcactcaagtggac     5670
5566 aggggaaaaagtaattgccatgggctccaaagaattgcttatgtttgctttattgtttctttagctatttaaaaataaatccatcaaaaataaagtatgcaaatgtatcttttt     5771
```

FIGURE 17 (CONT.)

Comparison between our sequence and alpha 2 Macroglobulin
(GI: 224053)

Identities = 63/197 (32%), Positives = 90/197 (46%), Gaps = 50/197 (25%)

```
Query: 621 YYLG--------------MFMNS--------------FAVFQECGLWVLTDANLTKDYI 651
           + G            +++N                 ++  ++ GL  T++ + K +
Sbjct: 605 GFPGPLNDQDDEDCINRHNVYINGITYTPVSSTNEKDMYSFLEDMGLKAFTNSKIRKPKM 664

Query: 652 DGVYDNAE----------YAERFMEENEGHIVDIHDFSLGSSPH---VRKHFPETWIWL 697
              E           Y    M     +V + +      PH   VRK+FPETWIW
Sbjct: 665 CPQLQQYEMHGPEGLRVGFYESDVMGRGHARLVHVEE------PHTETVRKYFPETWIWD 718

Query: 698 DTNMGSRIYQEFEVTVPDSITSWVATGFVISEDLGLGLTTTPVELQAFQPFFIFLNLPYS 757
              + S    E   VTVPD+IT W A  F +SED GLG+++T    L+AFQPFF+ L +PYS
Sbjct: 719 LVVVNSAGVAEVGVTVPDTITEWKAGAFCLSEDAGLGISST-ASLRAFQPFFVELTMPYS 777

Query: 758 VIRGEEFALEITIFNYL 775
           VIRGE F L+ T+ NYL
Sbjct: 778 VIRGEAFTLKATVLNYL 795
```

FIGURE 18

150 KDA TGF-B1 ACCESSORY RECEPTOR ACTS A NEGATIVE MODULATOR OF TGF-B SIGNALING

CROSS-REFERENCE TO RELATED APPLICATION

The present application claims priority to PCT/CA02/00560 filed on Apr. 24, 2002, which claims priority to provisional application No. 60/285,713 filed on Apr. 24, 2001, and to provisional application No. 60/358,713 filed on Feb. 14, 2002, all of which are hereby incorporated in their entirety by reference.

BACKGROUND OF THE INVENTION

Transforming growth factor-$\beta$ (TGF-$\beta$) is a 25 kDa multi functional growth factor which plays a central role in the wound healing process (Roberts and Sporn, 1990; O'Kane and Ferguson, 1997). It is an important regulator of the immune response (Letterio and Roberts, 1998), angiogenesis, reepithelialization (Roberts and Sporn, 1990), extracallular matrix protein synthesis and remodeling (Peltonen et al, 1991; Yamamoto et al, 1994). During wound healing, re-epithelialization initiates the repair process which is characterized by recruitment of epidermal stem cells, keratinocyte proliferation and the formation of an epithelial tongue of migrating keratinocytes at the wound edge (Clark, 1996). TGF-$\beta$ is chemotacfic to keratinocytes and induces the expression of integrins on the migrating epithelium (Helbda, 1988; Zambruno et al, 1995). In spite of its promigratory effect on keratinocytes, TGF-$\beta$ is a potent inhibitor to epithelial cell proliferation in vitro (Pietenpol et at, 1990) and in vivo (Glick et al, 1993). Targeted deletion of the TGF-$\beta$1 gene in keratinocytes causes rapid progression to squamous cell carcinoma (Glick et al, 1994). In addition, the epidermis of transgenic mice expressing a dominant negative TGF-$\beta$ receptor exhibits a hyperplastic and hyperkeratotic phenotype (Wang et al, 1997). These results support the importance of proper expression of TGF-$\beta$ and regulation of its function in epidermal development and maintenance of epidermal homeostasis.

TGF-$\beta$ is a member of the TGF-$\beta$ superfamily which also include activins, inhibins, bone morphogenic proteins, growth differentiation factor 1 (GDF-1) and glial-derived neurotropic growth factor (GDNF) (Kingsley, 1994).

There are three widely distributed TGF-$\beta$ receptors, type I, type II and type III, all of which have been cloned (Roberts and Sporn, 1990; Massague, 1998). The types I and II receptors are both transmembrane serine/threonine kinases that are essential for TGF-$\beta$ signal transduction. The type III receptor, also known as betaglycan, is a high molecular weight proteoglycan that is not required for signaling, but is believed to play a role in presenting the ligand to the type II receptor (Lopez-Casillas et al, 1993). Endoglin, is another TGF-$\beta$ receptor predominantly expressed on endothelial cells (Gougos and Letarte, 1990). According to the present model of TGF-$\beta$ signal transduction, binding of TGF-$\beta$ to the type II receptor which is a constitutively active kinase, leads to the recruitment and phosphorylation of the type I receptor (Wrana et al, 1994). The activated type I kinase phosphorylates the central intracellular mediators of TGF-$\beta$ signalling known as the Smad proteins (Heldin et al, 1997). Smad proteins can be classified into three groups: the pathway restricted Smads include the Smad2 and Smad3 which are phosphorylated by the type I receptor of TGF-$\beta$ or activin, while the Smads 1, 5 and 8 are implicated in BMP signalling. The phosphorylation of the pathway restricted Smads permits their interaction with the common Smad or Smad4 and this heteromeric complex then translocates into the nucleus where it regulates expression of target genes. Finally, there inhibitory Smads which include the Smad 7 and Smad 6 prevent the phosphorlyation of the R-Smads by the type I kinase. (Heldin et al, 1997, Massague, 1998; Wrana and Attisano, 2000)

In blood circulation, TGF-$\beta$1 is found bound to the carrier $\alpha_2$ macroglobulin ($\alpha_2$M; Webb et al. 1998). $\alpha_2$M binds many other cytokines and therefore lacks selectivity for TGF-$\beta$1. $\alpha_2$M polymorphism has been associated with Alzheimer's disease, which polymorphism is observed as a deletion in "the bait region" overlapping with TGF-$\beta$1 binding domina (Gonias et al. 2000 and Blacker et al 1998).

Although the types I and II receptors are central to TGF-$\beta$ signaling, it is possible that accessory receptors interacting with the signaling receptors modify TGF-$\beta$ responses. For example, both endoglin and type III receptor which form heteromeric complexes with the type II receptor have been reported to modulate TGF-$\beta$ function. When overexpressed in myoblasts, endoglin inhibited while type III receptor enhanced TGF-$\beta$ responses (Letamendia et al, 1998). In addition, endoglin was shown to antagonize TGF-$\beta$ mediated growth inhibition of human vascular endothelial cells (Li et al, 2000). Similarly, the newly identified type I-like receptor BAMBI which associates with TGF-$\beta$ family receptors can inhibit signaling (Onichtchouk et al, 1999).

There are also a number of molecules that can impact TGF-$\beta$ signal transduction by interacting with one or both of the TGF-$\beta$ signaling receptors. However, the exact physiological significance of many of these interactions are not clearly defined (for review, Massague, 1998). Three of these interacting proteins: the type II TGF-$\beta$ receptor interacting protein (TRIP-1) (Chen et al, 1995), B$\alpha$ ($\alpha$ subunit of protein phosphatase A) (Griswold-Prenner, 1998), and serine-threonine kinase receptor associated protein (STRAP) (Datta et al, 1998) all contain the highly conserved tryptophan-aspartic acid (WD) repeats. WD domains are important in protein-protein interactions and cellular functions such as cell cycle progression and transmembrane signaling (Neer et al, 1994). TRIP-1 is phosphorylated through its interaction with the type II receptor kinase and exerts an inhibitory effect on TGF-$\beta$ induced PAI-1 gene transcription, but has no effect on TGF-$\beta$ mediated growth inhibition (Choy and Derynck, 1998). On the other hand, B$\alpha$ associates with the type I receptor and positively modulates TGF-$\beta$ action. Finally, STRAP can interact with both the type I and II receptors and when overexpressed, it exerts an inhibitory effect on TGF-$\beta$ mediated transcriptional activation. In addition, STRAP can also interact with the inhibitory Smad7, but not Smad6. STRAP's interaction with Smad7 exerts a stabilizing effect on Smad7's association with the activated type I kinase receptor which prevents Smad2/3's association and subsequent phosphorylation (Datta and Moses, 2000).

The immunophilin, FKBP12, interacts with the TGF-$\beta$ type I receptor and acts as a negative modulator of TGF-$\beta$ function (Wang et al, 1996). It can interact with unactivated type I receptor and functions to stabilize the quiescent receptor state by protecting phosphorylation sites in the GS domain. Upon ligand stimulation, heteromerization and subsequent phosphorylation of the GS domain by the TGF-$\beta$ type II kinase results in the release of FKBP12 (Chen et al, 1997; Huse et al, 1999). In contrast, the TGF-$\beta$ type I receptor associated protein-1 (TRAP-1) interacts only with the activated type I receptor kinase (Charng et al, 1998).

TRAP-1 is not phosphorylated by the type I kinase and TRAP-1's interaction is reported to have an inhibitory effect on TGF-β signaling. However, a recent report describes a different function for TRAP-1 (Wurthner et al, 2001). In this study, TRAP-1 was found to associate with inactive TGF-β and activin receptor complexes and upon ligand stimulation, TRAP-1 is released. The conformationally altered TRAP-1 is then believed to associate and subsequently chaperone Smad4 to the activated Smad2. The α subunit of ras farnesyl protein transferase (FNTA) preferentially interacts with the activated type I receptor and is considered a substrate because it is phosphorylated by the type I kinase and released thereafter (Kawabata et al, 1995). However the functional significance of this phenomenon remains unexplained. The accessory receptors, endoglin and type III receptor which form heteromeric complexes with the type II receptor have also been reported to modulate TGF-β function. When overexpressed in myoblasts, endoglin inhibited while type III receptor enhanced TGF-β responses (Letamendia et al, 1998). Glycosylphosphatidyl inositol (GPI)-anchored proteins which lack transmembrane and cytoplasmic domains have also been shown to bind TGF-β. These proteins have been identified on certain cell lines (Cheifetz and Massague, 1991), but the identity of these GPI-anchored proteins and the role they may play in TGF-β signaling remain unknown. Recently, the present inventors reported the presence of GPI-anchored TGF-β binding proteins on early passage human endometrial stromal cells (Dumont et al, 1995), human skin fibroblasts (Tam and Philip, 1998) and keratinocytes (Tam et al, 1998). On human keratinocytes, they identified a 150 kDa GPI-anchored TGF-β1 binding protein designated as r150 that can form a heteromeric complex with the types I and II TGF-β receptors (Tam et al, 1998). In addition, they demonstrated that upon hydrolysis fom the cell surface by phosphatidylinositol phospholipase C (PIPLC), the soluble form of r150, retains its ability to bind TGF-β1 in the absence of the types I and II receptors. In addition, it was demonstrated that the GPI anchor is contained in a protein with a molecular weight of 150 kDa (Tam et al, 2001). This novel GPI-anchored TGF-β1 binding protein, r150, has the potential to antagonize or potentiate TGF-β action in keratinocytes. In the absence of the cDNA encoding r150, one way to examine the effect of r150's loss in TGF-β signaling is to enzymatically release the binding protein by PIPLC treatment prior to testing for alterations in TGF-β induced responses. However, the efficacy of exogenously added PIPLC is subject to variability, being affected by pH, temperature, and acylation of GPI-anchored proteins (Shukla, 1982; Chen et al, 1998), thus results obtained may be difficult to interpret. In addition, GPI-anchored proteins that are released may get re-synthesized and re-inserted in the plasma membrane soon after PIPLC hydrolysis. Hence, as an alternative, was have created and isolated a keratinocyte cell line that is mutated in GPI anchor biosynthesis. These cells display a significant loss of r150 from their cell surface, thus allowing a comparative examination of TGF-β mediated cellular responses in the GPI anchor deficient cell line versus the parental HaCat cells under stable experimental conditions GPI-anchored proteins lack transmembrane and cytoplasmic domains, and are attached to the cell membrane via a lipid anchor in which the protein is covalently linked to a glycosyl phosphatidylinositol moiety. GPI-anchored proteins have been reported to have roles in intracellular sorting (Rodriguez-Boulan and Powell, 1992), in transmembrane signaling (Brown, 1993) and to associate with cholesterol and glycosphingolipid-rich membrane microdomains (Brown and London, 1998; Hooper, 1999). Also, the GPI anchor enables a protein to be selectively released from the membrane by phospholipases (Metz et al, 1994; Movahedi and Hooper, 1997). r150 was characterized as GPI-anchored, based on its sensitivity to phosphatidylinositol phospholipase C (PIPLC). However, it is important to rule out other possibilities, namely, (i) r150 is not itself GPI-anchored, but is tightly associated with a protein that is GPI-anchored, and therefore is susceptible to release by PIPLC; (ii) r150 is a complex of two lower molecular weight proteins which became inadvertently cross-linked during the affinity labeling procedure.

It is now demonstrated that the GPI-anchor is contained in r150 itself and not on a tightly associated protein and that it binds TGF-β1 with an affinity comparable to those of the signaling receptors. Furthermore, the released (soluble) form of this protein binds TGF-β independent of the types I and II receptors. Also, the soluble form inhibits the binding of TGF-β to its receptor. In additiion, we provide evidence that r150 is released from the cell surface by an endogenous phospholipase C. Also, a mutant human keratinocyte cell line with a defect in GPI synthesis was created, which display reduced expression of r150. The results using these mutant keratinocytes suggest that the membrane anchored form of r150 is a negative modulator of TGF-beta responses. These findings, taken together with the observation that r150 forms a heteromeric complex with the signaling receptors, suggest that this accessory receptor in either its membrane anchored or soluble form and its down- or up-regulation may potentiate or antagonize TGF-β responses in human keratinocytes, respectively.

The complete amino acid of a molecule named CD109 was recently disclosed as well as the nucleic acids encoding same (Lin et al. 2002). Sequences comparisons with those of r150 suggest that CD109 is a r150 variant. No definite role has been assigned to CD109 by Lin et al.

SUMMARY OF THE INVENTION

This invention provides a molecule that binds TGF-β1 with a high level of selectivity. This molecule named r150 can be retrieved in a membrane anchored form or as a released free soluble form. Variants and parts of r150 which have the property to bind TGF-β1 are grouped under the name r150-like proteins or peptides. They include those defined in SEQ ID Nos: 2, 4, 8, 10 and 12. Their corresponding coding nucleic acids respectively defined in SEQ ID NOs: 1, 3, 5, 7, 9 and 11.

This invention provides for the use of a protein comprising any one of the following sequences in the making of a medication for inhibiting TGF-β1 activity in a biological tissue SEQ ID Nos: 2, 4, 6, 8, 10 and 12.

Also provided is the use of an antagonist to a protein comprising any one of the following sequences in the making of a medication for increasing TGF-β1 activity in a biological tissue: SEQ ID Nos: 2, 4, 6, 8, 10 and 12.

Also provided is the use of a nucleic acid encoding a protein comprising any one of the following sequences in the making of medication for inhibiting TGF-β1 activity in a biological tissue: SEQ ID Nos: 1, 3, 5, 7, 9 and 11.

Also provided is the use of a molecule which silences the expression of a nucleic encoding a protein comprising any one of the following sequences in the making of medication for increasing TGF-β1 activity in a biological tissue: SEQ ID Nos: 1, 3, 5, 7, 9 and 11. Particularly, the silencing molecule is an antisense nucleic acid.

The present inventors being the first to elucidate the complete nucleic acid sequence of r150 and of its deduced amino acid sequence, this invention provides an isolated nucleic acid encoding a protein comprising any one of the following sequences: SEQ ID Nos: 2, 4, 6, 8, 10 and 12.

In a specific embodiment, the nucleic acid comprises any one of the following nucleotide sequences: SEQ ID No: 1, 3, 5, 7, 9 and 11.

The nucleic acid is particularly one comprising the nucleotide sequence defined in SEQ ID No: 1.

The above nucleic acids may include crude nucleic acids or recombinant vectors; namely expression vectors capable of governing transcription and translation of the crude nucleic acids inserted downstream to a promotor, are preferred tools for producing r150-like proteins.

Recombinant host cells which comprise the nucleic acids or the recombinant vector are other tools. The vectors are normally selected to comprise sequences compatible with the host's machinery. Intervening sequences located 5' and 3' with regard to the crude nucleic acids are adapted or selected by the skilled artisan desirous to produce a particular type of host cells. The signal peptide may be charged also for another one more appropriate for a given cell type.

There host cells may be domesticated and used in a method of producing a r150-like protein. Such a method comprises the steps of:

growing a recombinant host cell in a culture medium supporting cell growth and expression of said nucleic acid:

recovering the protein from the culture medium or from the cell.

The nucleic acids may be antisense nucleic acids. They may be inserted in a recombinant vector, namely an expression vector and recombinant host cells which comprises such antisense nucleic acids can also be made.

It is further an object of this invention to provide a TGF-β1 binding reagent, which comprises a protein comprising any one of the following sequences: SEQ ID Nos 2, 4, 6, 8, 10 and 12.

Compositions of matter which comprise these reagents and a carrier are other objects of this invention.

The carrier may be a pharmaceutical carrier. Otherwise, it may be a solid support to which r150 is bound to immobilize TGF-β1.

DESCRIPTION OF THE INVENTION r150 is a TGF-β1 binding molecule. Its complete amino acid sequence as well as the nucleic acid sequence encoding same appear to have been first elucidated by the present inventors. Another group (Lin et al. 2002), using a very different approach (affinity binding to monoclonal antibodies) has found a blood cell surface antigen, which they called CD109. Sequence comparisons show that CD109 (SEQ ID Nos 5 and 6) comprises a 17 amino acid insertion at position 1218–1234 (51 nts). This addition accounts for the difference in amino acids number (1445 for CD109 versus 1428 for r150). Besides that, substitutions of nucleotides are noted: r150 amino acid thr$^{1224}$ is changed for a methionine (CD109 amino acid 1241). CD109 shows polymorphism at residue 703 (Schuh et al. 2002). A tyrosine or a serine represent different alleles of CD109. Such polymorphism would presumably exist for r150. It is possible that CD109 or r150 are responsible for the building of an immune response since allo antibodies are retrieved upon administration of CD109 isoforms. It may therefore be implied that an isoform compatible with the recipient subject's tissue may have to be selected as an administrable r150 active ingredient.

r150 binds or sequesters TGF-β1, in its membrane anchored form as well as in its free soluble form (SEQ ID Nos: 4 and 8). As a result, TGF-β1 availability is reduced. The effects induced by TGF-β1 are therefore negatively modulated (or inhibited). Such inhibition may be desirable in conditions where overproduction of TGF-β1 leads to pathological states (cancer is a specific example of such pathology). On the contrary, in other occasions, increasing TGF-β1 activity may be sought. For example, TGF-β1 encourages tissue or organ graft success. Therefore silencing r150 would have for effect to increase TGF-β1 availability and increase graft success.

r150 further appears to be related to $\alpha_2$ macroglobulin ($\alpha_2$M) and since the TGF-β binding domain has been determined for $\alpha_2$M by Webb et al. (1998), the corresponding domain in r150 is presumed to be located a region corresponding to $\alpha_2$ macroglobulin amino acids 666–706. These corresponds to r150 amino acids 651–683 (SEQ ID No: 10). Therefore, the r150 peptide having the sequence defined in SEQ ID NO: 10 is also contemplated as TGF-β1 binding peptide within the scope of the invention; the nucleic acid encoding this peptide is as well.

Webb et al. (2000) even found the minimal $\alpha_2$M TGF-β1 binding sequence which appears to be delineated by amino acid 717 and 733. The corresponding stretch in r150 is found between amino acid residues 694 and 712 (SEQ ID No.12).

Gomas et al. (2000) reported that $\alpha_2$M gene polymorphism has been associated with Alzheimer's disease, which polymorphism is observed as a deletion in "the bait region" overlapping with TGF-β1 binding domain. It is envisageable that r150 could be useful to sequester and neutralize TGF-β1 especially in diseases wherein $\alpha_2$M is deficient. Any portion of r150 or variants thereof that is capable of binding TGF-β1 activity is intended to be used in the making of a medication or a method or composition for inhibiting TGF-β1 activity. This includes proteins or peptides comprising sequences defined in SEQ ID NOs. 2, 4, 6, 8, 10 and 12. These r150-like proteins or peptides would include any molecule having at least 50% homology with the above sequences. On the opposite, any molecule having an antagonistic activity to the above r150-like proteins or peptides would find a use in the making of a medication or a method or a composition for increasing TGF-β1 activity.

Nucleic acids encoding the above r150-like proteins or peptides represent an alternative to the direct administration of proteins or peptides. Antisense nucleics would on the opposite silence the expression of r150-like proteins or peptides. All these nucleic acids include recombinants vectors, namely expression vectors, which are available and well known to the skilled artisan.

A very large body of literature describes diseases or disease models involving up and down regulation of TGF-β1 activity. Nowadays, TGF-β1 binding proteins decorin and an anti-TGF antibody are currently under clinical trials. The present r150-like proteins or peptides could represent a valuable and advantageous alternative to these molecules, because of their selectivity for TGF-β1 isoform, combined to their hydrosolubility.

Here is a non-exhaustive list of disease models where alteration of TGF-β action has been shown to be of therapeutic benefit:

Cancer progression:

Note: TGF-β has biphasic effects during tumorigenesis, acting early as a tumor suppressor, but later stimulating cancer progression.

(i) Suppression of tumor progression by TGF-β

Akhurst R. J. and Derynck R. (2001). TGF-β signaling in cancer a double-edged sward. TRENDS in Cell Biology 11: S44–S51.

Welch, Dr. et al (1990). Transforming growth factor-β stimulates mammary adenocarcinoma cell invasion and metastatic potential. Proc. Natl. Acd. Sci. USA 87: 7678–7682

Markowitz, S. et al. (1995) Inactivation of the type II TGF-β receptor in colon cancer cells with microsatellite instability. Science 268,1336–1338.

Massague .J. et al. (2000) TGF-β signaling in growth control, cancer, and heritable disorders. Cell 103, 295–309.

(ii) Stimulation of tumor progression by TGF-β

Hojo, M. et al. (1999) Cyclosporine induces cancer progression by a cell-autonomous mechanism. Nature 397, 530–534.

Yin, J. J. et al. (1999) TGF-β signaling blockade inhibits PTHrP secretion by breast cancer cells and bone metastases development. J. Clin. Invest. 103, 197–206.

Exogenous TGF-β1 promotes wound healing where as inhibiting TGF-β1 activity or enhancing TGF-β3 activity reduces scarring in animal models Roberts, A. B., and Sporn, M. B. (1996). Transforming growth factor R. A. F. (ed), Plenum Press, New York, p275–308.

Mustoe, T. A., Pierce, G. F., Thomason, A., Gramates, P., Sporn, M. B., and Deuel, T. F. (1987). Accelerated healing of incisional wounds in rats induced by transforming growth factor-β. Science 237: 1333–1336.

Quaglino, D., Nanney, L. B., Ditesheim, J. A., and Davidson, J. M. (1991). Transforming growth factor-β stimulates wound healing and modulates extracellular matrix gene expression in pig skin: incisional wound model. J. Invest. Dermatol. 97: 34–42.

O'Kane, S., and Ferguson, M. W. J. (1997). Transforming growth factor-βs and wound healing. Int. J. Biochem. Cell. Biol. 29:63–78.

Shah, M., Foreman, D. M., and Ferguson, M. W. J. (1995). Neutralization of TGF-β1 and TGF-β2 or exogenous addition of TGF-β3 to cutaneous rat wounds reduces scarring. J. Cell Science 108: 985–1002.

Choi, B-M., Kwak, H-J., Jun, C-D., Park, S-D., Kim, K-Y., Kim, H-R., and Chung, H-T. (1996). Control of scarring in adult wounds using antisense transforming growth factor-β1 oligodeoxynucleotides. Immunol. Cell Biol. 74:144–150.

Blocking TGF-β1 overproduction reduce tissue fibrosis (pulmonary fibrosis, liver cirhosis, glomerulonephritis, scleroderma and atherosclerosis).

Border et al, (1990). Suppression of experimental glomerulonephritis by antiserum against transforming growth factor beta 1. Nature 346 (6282): 371–374

Isaka Y., Brees D. K., lkegaya K., Kaneda Y., Imai E., Noble N. A., Border W. A. (1998). Gene therapy by skeletal muscle expression of decorin prevents fibrotic disease in rat kidney. Nat. Med. 2: 418–423.

Isaka Y., Akagi Y., Ando Y., Tsujie M., Sudo T., Ohno N., Border W. A., Noble N. A., Kaneda Y., Hori M., and Imai E. (1999). Gene therapy by transforming growth factor-beta receptor-IgG Fc chimera suppressed extracellular matrix accumulation in experimental glomerulonephritis [see comments]. Kidney Int. 55:465–475.

Khalil, N. and Greenberg A H (1991). The role of TGF-β in pulmonary fibrosis. Ciba Found Symp. 157: 194–207.

Yamamoto, T., Takagawa S., Katayama I., and Nishioka K. (1999). Anti-Sclerotic effect of transforming growth factor-beta antibody in a mouse model of bleomycin-induced scleroderma. Clin Immunol, 92(1):6–13.

Gressner, A. M., Weiskirchen, R., Breitkopf K., and Dooley S. (2002). Roles of TGF-beta in hepatic fibrosis. Front Biosci (7): d793–807.

Sheppard D. (2001). Integrin-mediated activation of transforming growth factor-beta(1) in pulmonary fibrosis. Chest 120(1 Suppl):49S-53S.

McCaffrey, T. A. (2000). TGF-βs and TGF-β receptors in atherosclerosis. Cytokine. Growth Factor Rev. 11: 103–114.

TGF-beta has tissue protective effects (against ischemia reperfusion injury) in the heart, brain and kidney.

Lefer A M., Ma X-L., Weyrich A S, Scalia R. (1993). Mechanism of the cardioprotective effect of TGF-β1 in feline myocardial ischemia and reperfusion. Proc. Natl. Acad. Sci. USA 90: 1018–1022.

Lefer A M, Tsao P, Aoki N, Palladino M A. (1990). Mediation of cardioprotection by transforming growth factor-β. Science 249: 61–64.

McNeill H. Williams C, Guan J, Dragunow M, Lawlor P, Sirimanne E, Nikolics K,

Gluckman P. (1994). Neuronal rescue with transforming growth factor-beta 1 after hypoxic-ischaemio brain injury. Neuroreport 5: 901–904.

Mehta J L, Yang B C, Strates B S, Mehta P. (1999). Role of TGF-beta1 in platelet-mediated cardioprotection during ischemia-reperfusion in isolated rat hearts. Growth Factors 16: 179–190.

Recombinant hosts comprising the above nucleic acids or recombinant expression vectors can be used as a biological machinery in the production of the r150-like proteins or peptides. The elucidation of the nucleic acid sequence of r150 therefore leads to a method of producing these proteins or peptides by recombinant technology.

A variety of TGF-β1 binding reagents and compositions may be derived from the present invention.

First, peptides such as those defined in SEQ ID. Nos: 10 and 12 may be used as such as a TGF-β1 binding reagent. Larger molecules like those defined in SEQ ID Nos 2, 4, 6 and 8 could be conjugated (through their anchoring region) to a carrier. The carrier may take the form, for example, of a solid or semi-solid medium (beads, chromatography columns, plates, etc.), to immobilize TGF-β1. Pharmaceutical compositions would take any suitable form, depending on the selected route of administration. A r150-like protein or peptide (SEQ ID Nos: 2, 4, 6, 8, 10 and 12) would be formulated with a pharmaceutically acceptable carrier. Doses equivalents those used by intravenous route for decorin and/or the TGF-antibody can be produced.

Objects, advantages and features of the present invention will become more apparent upon reading of the following non restrictive description of preferred embodiments thereof, given by way of example only with reference to the accompanying drawings.

BRIEF DESCRIPTION OF THE FIGURES

FIG. 17: Sequences of CD109, publishes by another, represent r150 putative variants. (Genbak accession numbers AF410459 and AAL84159.1.)

FIG. 18: Alignment of $α_2$-macroglobulin and r150 partial sequences.

EXAMPLE 1

Figure 1:
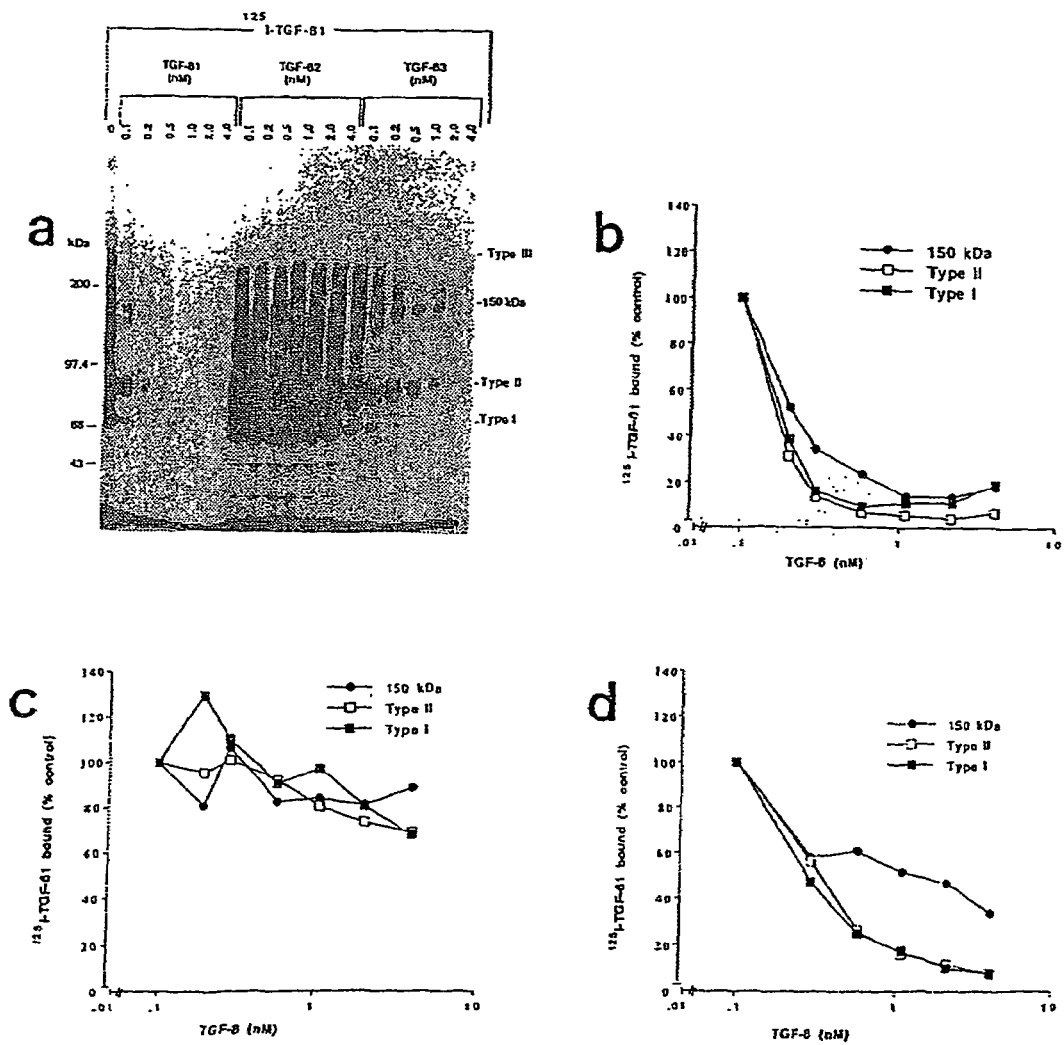
FIG. 1: Affinity cross-link labeling of human neonatal keratinocytes with $^{125}$I-TGF-β1. Confluent monolayers were affinity labeled with 100 pM $^{125}$I-TGF-β1 in the absence or presence of unlabeled TGF-β1, -β2, or -β3. Solubilized cell extracts were analyzed by SDS-PAGE under non reducing conditions and autoradiography (a). Competition curves for r150 and the types I and II TGF-βreceptors were derived by densitometric analysis of a typical autoradiogram. The data for each binding complex are expressed as a percent of the value in control wells incubated with $^{125}$I-TGF-β1 alone and are plotted against the concentration of unlabeled TGF-β1 (b), -β2 (c), or -β3 (d). The autoradiogram and competition curves are representative of three different experiments.

Characterization of TGF-β1 Binding Protien Different from other TGF-β Receptors

Methods

Cell Culture:

Neonatal keratinocytes were prepared from foreskin tissue obtained at newborn male circumcision as described by Germain et al (1993). The keratinocytes were cultured in keratinocyte serum free medium (Gibco, Burlington, Ontario) and cells of third to fifth passage were used for experiments. The immortalized keratinocyte cell line, HaCaT, was obtained from Dr. Boukamp (Heidelberg, Germany), and the mink lung epithelial cells (Mv1Lu) were from ATCC. Both cell types were maintained in Dulbecco's Minimal Essential Medium (D-MEM) supplemented with 5% FBS, 1 mM sodium pyruvate, 2 mM glutamine, 100 U/ml penicillin, 100 μg/ml streptomycin, and 0.25 μg/ml amphotericin (Gibco, Burlington, Ontario). All cells were maintained at 37° C. in an atmosphere of 5% $CO_2$/air.

Affinity Labeling of Cells:

Iodination of TGF-β1 (Collaborative Biomedical) was done as described (Philip and O'Connor-McCourt, 1991). Affinity labeling technique was performed as detailed previously (Dumont et al, 1995). Briefly, cell monolayers were washed with ice-cold binding buffer (D-PBS or Dulbecco's phosphate-buffered saline with $Ca^{2+}$ and $Mg^{2+}$, pH 7.4) containing 0.1% bovine serum albumin (BSA). Cells were incubated with 100–200 pM of $^{125}$I-TGF-β1 for three hours at 4° C. In some experiments, incubations were done in the absence or presence of increasing concentrations of unlabeled TGF-β isoforms to determine the competition profiles of the receptors. The receptor-ligand complexes were cross-linked with 1 mM Bis-(Sulfosuccinimidyl) suberate ($BS^3$, Pierce). The reaction was stopped by the addition of glycine and the cells were solubilized, and separated on 3–11% polyacrylamide SDS gel. The results were analyzed by using autoradiography followed by quantitative densitometry (Gel-Cypher, Lightools Inc, Encinitas, Calif. or ImageQuant, Molecular Dynamics, Sunnyvale, Calif.)

Temperature Induced Phase Separation in Triton X-114 of r150 and Hydrolysis by PIPLC:

Temperature induced phase separation in Triton X-114 and PIPLC treatment was performed as described previously with modifications (Bordier, 1981). Keratinocytes were affinity labeled with 150 pM of $^{125}$I-TGF-β1 and lysed in TBS (10 mM Tris-HCl, pH 7.5, 150 mM NaCl) containing 1% Triton X-114, 1 mM phenylmethylsufonyl fluoride and protease inhibitor cocktail (200 μg/ml BSA, 1 μg/ml leupeptin, 10 μg/ml benzamide, 10 μg/ml soyabean trypsin inhibitor and 2 μg/ml pepstatin) for 60 minutes at 4° C. The cell lysates were centrifuged at 13 000×g for 15 minutes at 4° C. The Triton X-114 soluble material was incubated at 30° C. for 10 minutes followed by a 10 minute centrifugation at 13 000×g at room temperature to separate the detergent rich phase from the aqueous detergent poor phase. An aliquot (20%) from each phase was precipitated with ethanol/acetone, and analyzed by SDS-PAGE and autoradiography. The remaining 80% of the detergent phase was utilized to determine the effect of PIPLC on the detergent solubility of r150 using the method of Lisanti et al (1988). Briefly, the GPI-anchored protein enriched detergent phase was incubated with or without 0.6 U/ml of PIPLC (Roche Diagnostics) for one hour at 37° C. with mild agitation. Temperature induced phase separation was then repeated. Both the aqueous and detergent phases were precipitated by adding ethanol/acetone, and subjected to SDS-PAGE and autoradiography.

Affinity Labeling of Soluble r150:

Neonatal keratinocytes were harvested by treating confluent monolayers with Hanks' balanced salt solution containing 5 mM EDTA (pH 7.5). The cell pellet was washed with D-PBS and treated with 0.6 U/ml of PIPLC or left untreated, for one hour at 37° C. with mild agitation.

The supernatant containing the released GPI-anchored proteins was collected and concentrated by Centricon 30 (Amicon). Aliquots of the concentrated supernatant were affinity labeled with 150 pM of $^{125}$I-TGF-β1 in the absence or presence of excess unlabeled TGF-β (7.5 nM) and analyzed by SDS-PAGE as described above except that the solubilization step was omitted.

$^{125}$I-TGF-β1 Binding to Mv1Lu Cells

To test whether soluble r150 regulates the binding of TGF-β to its receptors, the supernatant obtained from PIPLC treated HaCaT cells were used in a $^{125}$I-TGF-β1 Mv1Lu binding assay. The HaCaT cells; which display the r150 with identical properties as the neonatal keratinocytes (Tam et al, 1998), were grown in T-25 cm$^2$tissue culture flasks (Falcon) were left untreated or treated with PIPLC, and the resulting supernatants were concentrated by Centricon 30 (Amicon). Mv1Lu cells were incubated with 50 pM of $^{125}$I-TGF-β1 in the absence or presence of increasing doses of the concentrated supernatant for three hours at 4° C. The cells were washed, solubilized and the bound radioactivity was determined by a gamma counter.

To rule out the possibility that any alteration in $^{125}$I-TGF-β1 binding caused by the supernatants was not due to the presence of TGF-β1, the above binding assay was also done in the presence of the supernatant treated with an anti-TGF-β1 antibody. The supernatant was incubated with the antibody (15 μg/ml) overnight at 4° C. It was then precleared of immune complexes and excess antibody that may interfere with the assay, by incubating with a protein A Sepharose slurry (PharmaciaBiotech) for two hours before addition to the assay. The TGF-β1 antiserum (obtained from Dr. M. O'Connor-McCourt; Moulin et al, 1997) was purified on a HiTrap Protein G column (PharmaciaBiotech) following standard procedures. The specificity of the antibody was verified by Western Blot analysis Determination of TGF-β Concentration in HaCaT Supernatant:

The concentration of TGF-β1 was quantitated in the supernatants from HacaT calls left untreated or treated with PIPLC using a mink lung epithelial cells-luciferase assay as described by Nunes et al (1996). This quantitative bioassay for TGF-β is based on the ability of TGF-β to induce the expression of plasminogen activator inhibitor type 1 (PAI-1) gene. The mink lung epithelial cells stably transfected with an expression construct containing a truncated PAI-1 promoter fused to the luciferase reporter gene were provided by Dr. D. B. Rifkin (New York University Medical Center). Briefly, these cells were incubated with varying doses of HaCaT supernatant, and the luciferase activity (expressed as relative light units) was quantitated by a Berthold Luminometer. Recombinant TGF-β1 (Austral Biochemicals; 0.5 pM-50 pM) was used to create a standard curve.

Immunoaffinity Chromatography and Immunoblotting of r150:

Neonatal keratinocytes were harvested by treating confluent monolayers with Hanks' balanced salt solution containing 5 mM EDTA (pH 7.5). The cell pellet was washed with D-PBS and treated with 0.6 U/ml of PIPLC for one hour at 37° C. with mild agitation. The supernatant containing the released GPI-anchored proteins was purified through a TGF-β1 affinity column (made available by Dr. M. O'Connor-McCourt, Montreal, Quebec). The column was prepared by incubating one milligram of TGF-β1 in a 200 mM HCO$_3$ (pH 8.3) buffer containing 30% (v/v) of n-propanol with five milligrams of Reacti-gel (Pierce) for 72 hours at 4° C. The reaction was stopped by the addition of 200 μl of 2 M TBS (pH 7.4), and the gel was washed to remove any unbound TGF-β1. The supernatant containing the GPI-anchored medium was loaded on the column equilibrated with 60 mM Tris (pH 7.4) and eluted with a 10 mM citrate/300 mM NaCl buffer (pH 2.5). Fractions of 0.5 ml were collected, and each fraction was analyzed for binding to TGF-β1, and immunoblotted for the presence of GPI anchor.

To verify binding to TGF-β1, an aliquot from each fraction was affinity labeled with 150 pM of $^{125}$I-TGF-β1 and analyzed by SDS-PAGE and autoradiography as described above, except that the solubilization step was omitted.

The fraction containing r150 and adjacent fractions were immunoblotted with the anti-CRD antibody to detect the GPI anchor. The anti-CRD antibody is specific to the inositol 1,2 cyclic monophosphate moiety, known as the "cross-reacting determinant" (CRD) which is exposed in GPI-anchored proteins that have been hydrolyzed by PIPLC. The antibody obtained from Oxford GlycoSystems (Wakefield, Mass.), was raised against the inositol 1,2 cyclic monophosphate moiety of the trypanosome variant surface glycoprotein (VSG). Samples were analyzed on 3–11% polyacrylamide gradient SDS gels and transferred to nitrocellulose membrane. The membrane was blocked in TBS-T (30 mM Tris, 150 mM NaCl, pH 7.5, 0.5% Tween 20) containing 5% non-fat dry milk and was incubated overnight with 4 μg/ml of the anti-CRD antibody at 4° C. The blots were washed in TBS-T and incubated for three hours at room temperature with the alkaline phosphatase conjugated secondary antibody (1:1500) (Roche Diagnostics). The membrane was then subjected to chemiluminescence analysis (CDP-Star) as detailed by the manufacturers (Roche Diagnostics).

Immunoprecipitation of r150:

Two different anti-CRD antibodies (i) Oxford GlycoSystems antibody and (ii) an antibody raised against a mammalian GPI-anchored pig membrane dipeptidase (MDP) were used for immunoprecipitation studies. The latter antibody was isolated from the bulk of the anti-MDP antiserum by fractionation on a column of the immobilized form of the trypanasome variant surface glycoprotein. Both anti-CRD antibodies are specific to the inositol 1,2-cyclic monophosphate and have been well characterized (Zamze et al. 1988; Broomfield and Hooper, 1993). Cells were affinity labeled with 200 pM $^{125}$I-TGF-β1 and cell extracts were incubated with the anti-CRD antibody. The resulting immune complexes were treated with protein A Sepharose (Pharmacia-Biotech) slurry and the beads were pelleted by centrifugation, and were analyzed by SDS-PAGE under reducing conditions followed by autoradiography.

Results

Binding Affinity of r150 for TGF-β Isoforms:

The present inventors have previously reported that in addition to the types I, II and III receptors, keratinocytes express a novel GPI-anchored TGF-β1 binding protein r150 which forms a heteromeric complex with the TGF-β signaling receptors (Tam et al, 1998). Since this protein has the potential to regulate TGF-β signaling, it was further characterized. Here was determined the relative affinity of r150 for the three TGF-β isoforms and, this affinity for TGF-β1 approximates that of the TGF-β signaling receptors, which suggests that r150 is predominantly a TGF-β1 binding protein. Keratinocytes affinity labeled with $^{125}$I-TGF-β1 in the absence or presence of increasing concentrations of unlabeled TGF-β1, -β2 or -β3, were analyzed by SDS-PAGE and autoradiography (FIG. 1a), and competition curves were created from the autoradiogram for r150, type I and type II receptors using quantitative densitometry (FIGS. 1b, c, and d). r150 is not sensitive to reducing agents since its migration pattern is identical when the SDS-PAGE analysis is done under non-reducing (FIG. 1a) or reducing conditions (Tam et al, 1998). The half-maximal inhibition of $^{125}$I-TGF-β1 binding was determined from the competition curves as the TGF-β isoform concentration at which the inhibition was 50% of that observed when no unlabeled ligand was present (Table 1). The concentration of unlabeled TGF-β1 required for half maximal inhibition of $^{125}$I-TGF-β1 binding by r150 is only 1.2 and 1.3 times higher than that required by type I and II receptors respectively. Although r150 also binds TGF-β3, it does so with a much lower affinity as compared to the types I and II receptors since it requires a six-fold higher concentration of TGF-β3 to reach half-maximal inhibition of $^{125}$I-TGF-β1 binding than the types I or II receptors. Unlabeled TGF-β2, even at 40 times excess concentrations minimally inhibited $^{125}$I-TGF-β1 binding of r150.

Partitioning of the Membrane Bound and Released r150 in Triton X-114:

In order to ascertain that the membrane bound r150 is hydrophobic as expected of a GPI-anchored protein and that the released r150 behaves as a hydrophilic soluble protein, the temperature dependent phase separation property of the non-ionic detergent Triton X-114 was used. Phase separation using Triton-X 114 results in the partitioning of hydrophilic proteins into the aqueous detergent poor phase while integral membrane proteins and lipid attached proteins partition into the detergent rich phase. This procedure has been useful in distinguishing between the amphipathic (membrane bound) and hydrophilic (released from cell surface) forms of GPI-anchored proteins (Hooper, 1992).

Affinity labeled keratinocytes were subjected to Triton X-114 partitioning and the detergent rich phase containing hydrophobic proteins and the detergent poor phase containing the hydrophilic proteins were analyzed by SDS-PAGE. As expected of a GPI-anchored protein, r150 partitioned predominantly into the detergent rich phase, along with the transmembrane type I, II and III receptors (FIG. 2A). The partitioning of soluble r150 in Triton X-114 was then tested. When the detergent rich phase containing the membrane bound affinity labeled r150 was left untreated or treated with PIPLC, and the temperature-induced phase separation was repeated, the aqueous phase of the sample treated with PIPLC was enriched in r150 while that of the sample left untreated contained only low amounts of r150 (FIG. 2B). These results strongly indicate that the PIPLC-released r150 is indeed hydrophilic. In contrast, the detergent phase of samples left untreated with PIPLC contained the major portion of r150 while the detergent phase of samples treated with PIPLC contained minimal amounts of r150 (data not shown).

The Soluble r150 Binds TGF-β1

Was next examined whether r150 released from the cell surface is capable of binding TGF-β1

Figure 3:
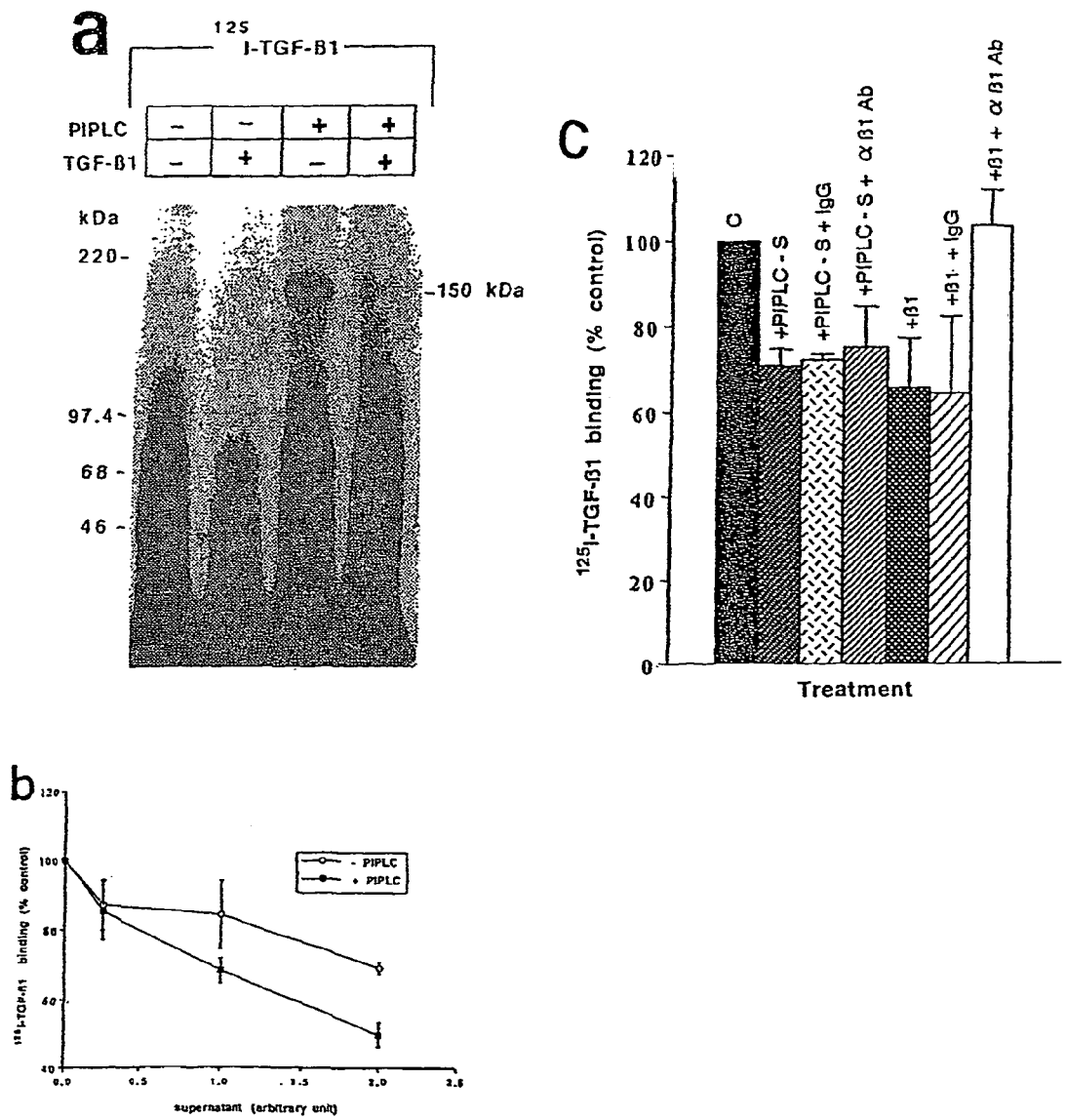
FIG. 3: (a) Affinity labeling of soluble r150 with $^{125}$I-TGF-β1. To verify that the soluble form of the r150 can bind to TGF-β1, human keratinocytes (HaCaT) were left untreated (−) or treated with 0.6 U/ml of PIPLC (+). The GPI-anchored proteins released into the supernatant were concentrated and an aliquot was affinity cross-link labeled with 150 pM of $^{125}$I-TGF-β1 in the absence or presence of excess unlabeled TGF-β1 and subjected to SDS-PAGE under reducing conditions. The result shown is representative of four different experiments. (b) inhibition of $^{125}$I-TGF-β1 binding to TGFβ receptors by soluble r150. Confluent monolayers of HaCaT cells grown in T-25 cm$^2$ culture flasks were left untreated or treated with 0.6 U/ml of PIPLC for 60 minutes at 37° C. The supernatants were collected and concentrated by Centricon. MvLu1 cells were affinity labeled with 50 pM $^{125}$I-TGF-β1 in the absence or presence of indicated doses of supernatants and $^{125}$I-TGF-β1 specifically bound was plotted as a function of the amount of supernatant used. The arbitrary unit of "1" is equivalent to a dose of supernatant from a T-25 cm$^2$ flask (approximately 1×10$^6$ cells). (c) Effect of anti-TGF-β1 on the inhibition of TGF-β1 binding to TGF-β receptors. Confluent monolayers of MvLu1 cells were affinity labeled with 50 pM $^{125}$I-TGF-β1 in the absence (C), or presence of PIPLC treated supernatant (+PIPLC-S), or PIPLC-S pretreated with non-immune rabbit IgG (15 μg/ml), or PIPLC-S pretreated with anti-TGF-β1 antibody (15 μg/ml). To demonstrate that the anti-TGF-β1 antibody effectively neutralizes TGF-β, experiments were also performed with 100 pM of TGF-β1 (+β1), β1 pretreated with non-immune rabbit IgG (15 μg/ml), or β1 pretreated with anti-TGF-β1 antibody (15 μg/ml). The values shown in (b) and (c) are the mean (+/−S.D.) of at least three to five different experiments.

Data shown in FIG. 3a demonstrate that soluble r150 in the supernatant obtained from keratinocytes treated with PIPLC could be affinity labeled with $^{125}$I-TGF-β1. This binding was specific since it was markedly reduced when the labeling was done in the presence of unlabeled TGF-β1. unlabeled TGF-β1 did not exhibit any competition for these complexes.

The low molecular weight bands below 97.4 kDa appear to be nonspecific since unlabeled TGF-β1 did not exhibit competition for these complexes in a reproducible manner. The fact that released r150 binds TGF-β1 indicates that r150 is capable of binding the ligand in the absence of type I, II and III TGF-β receptors or an intact membrane structure. Interestingly, detectable amounts of r150 were observed in the supernatant not treated with PIPLC, which led us to suspect that there might be an endogenous phospholipase capable of releasing r150.

Figure 5:
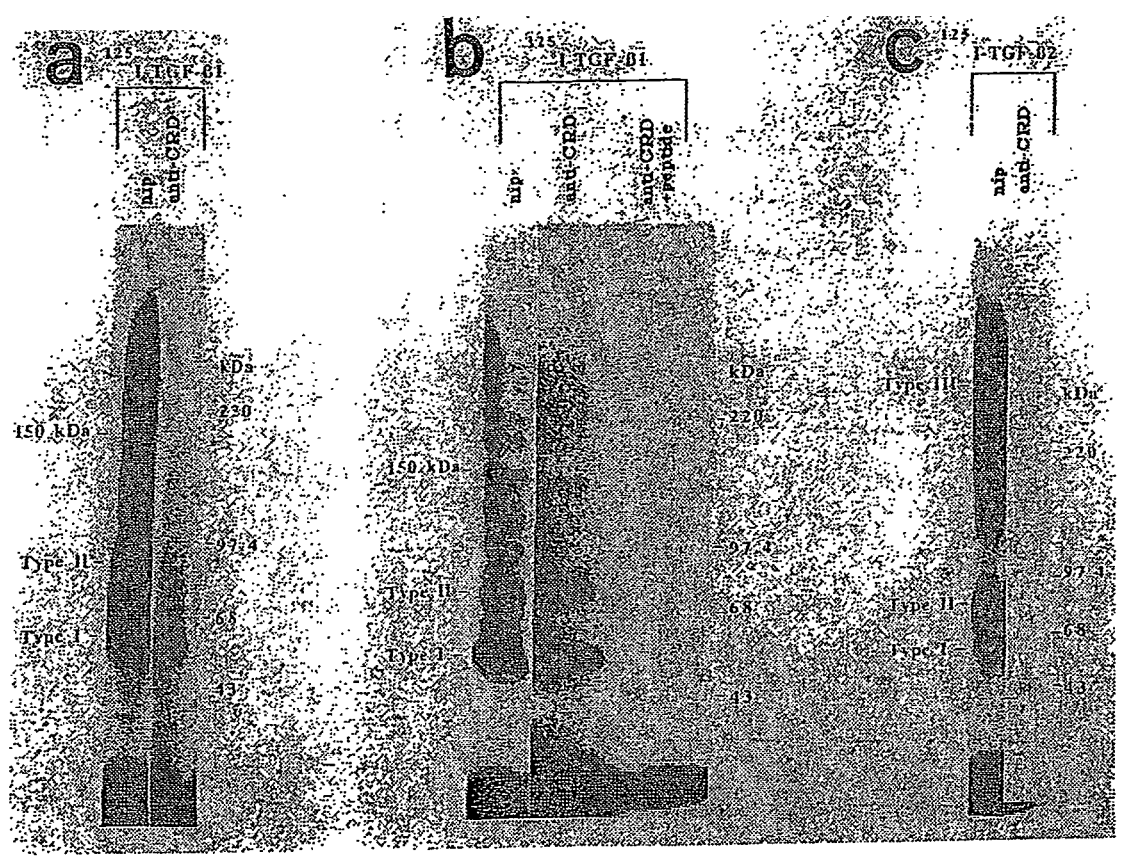
FIG. 5: Immunoprecipitation of affinity labeled TGF-β binding complexes on human neonatal keratinocytes with the anti-CRD antibodies. Keratinocytes not treated with PIPLC were affinity labeled with 100 pM $^{125}$I-TGF-β1 (a & b) or $^{125}$I-TGF-β2 (c) and were not immunoprecipitated (nip) or subjected to immunoprecipitation with an anti-CRD antibody against trypanosomal sVSG (Oxford GlycoSystems) (a & c), or with an anti-CRD antibody against porcine membrane dipeptidase (Broomfield and Hooper, 1993) (c). In the lane marked anti-CRD+peptide the immunoprecipitation was carried out using the anti-CRD antibody which was proincubated with PIPLC treated membrane dipeptidase. Immune complexes were subjected to SDS-PAGE under reducing conditions and analyzed by autoradiography. The results shown are representative of at least four to five experiments.

That the soluble r150 can inhibit TGF-β1 binding to TGF-β receptors was demonstrated using a binding assay. As seen in FIG. 3b, the supernatant from PIPLC treated keratinocytes competed in a dose dependent fashion for $^{125}$I-TGF-β as seen by decreased binding to MvLu1 cells. The supernatant from a T-25 cm$^2$ flask treated with PIPLC inhibited binding by 33% (p<0.005) and 50% (p<0.04) at doses of 1 and 2 respectively (approximately 1×10$^6$ cells, represented as an arbitrary unit of "1" in FIG. 3b). The inhibition of binding with the supernatant from cells not treated with PIPLC is consistent with the observation that detectable amounts of r150 is present in this supernatant, alluding to the presence of an endogenous phospholipase capable of releasing r150 (FIG. 3a; also see below, FIG. 5). This inhibition of $^{125}$I-TGF-β1 binding to MvLu1 cells corresponded to 15%, and 31% (p<0.03 in both cases), respectively for doses 1 and 2. In the PIPLC treated supernatants, the inhibition of binding at doses 1 and 2 was significantly higher (p<0.03 in both cases) than in the untreated supernatants.

To rule out the possibility that the competition observed by PIPLC treated supernatant was due to TGF-β, the supernatant was neutralized with anti-TGF-β1 antibody prior to being used in the binding assay. Neutralization with this antibody had no effect on the inhibition by the r150 enriched supernatant (FIG. 3c). In contrast, 100 pM TGF-β1 markedly inhibited $^{125}$I-TGF-β1 binding and this binding could be neutralized by anti-TGF-β1 antibody but not by non-immune IgG. Furthermore, using a PAI-luciferase assay no TGF-β was detected in the supernatants of cells untreated or treated with PIPLC (data not shown). Taken together, these results suggest that the released form of r150 is capable of binding to TGF-β1 and modulating ligand binding to TGF-β receptors.

Identification of a GPI-Anchor in r150:

Although r150 is sensitive to PIPLC, it is possible that it is not itself GPI-anchored, but is associated with a protein that is GPI anchored. Also, it is conceivable that it is a complex of two lower molecular weight proteins which became inadvertently cross-linked during the affinity labeling procedure. In order to eliminate these possibilities, Western blot analysis of r150 was performed after its release from the cell membrane using an anti-CRD antibody specific for an epitope which becomes exposed in GPI anchored proteins only upon treatment with PIPLC.

Figure 4:
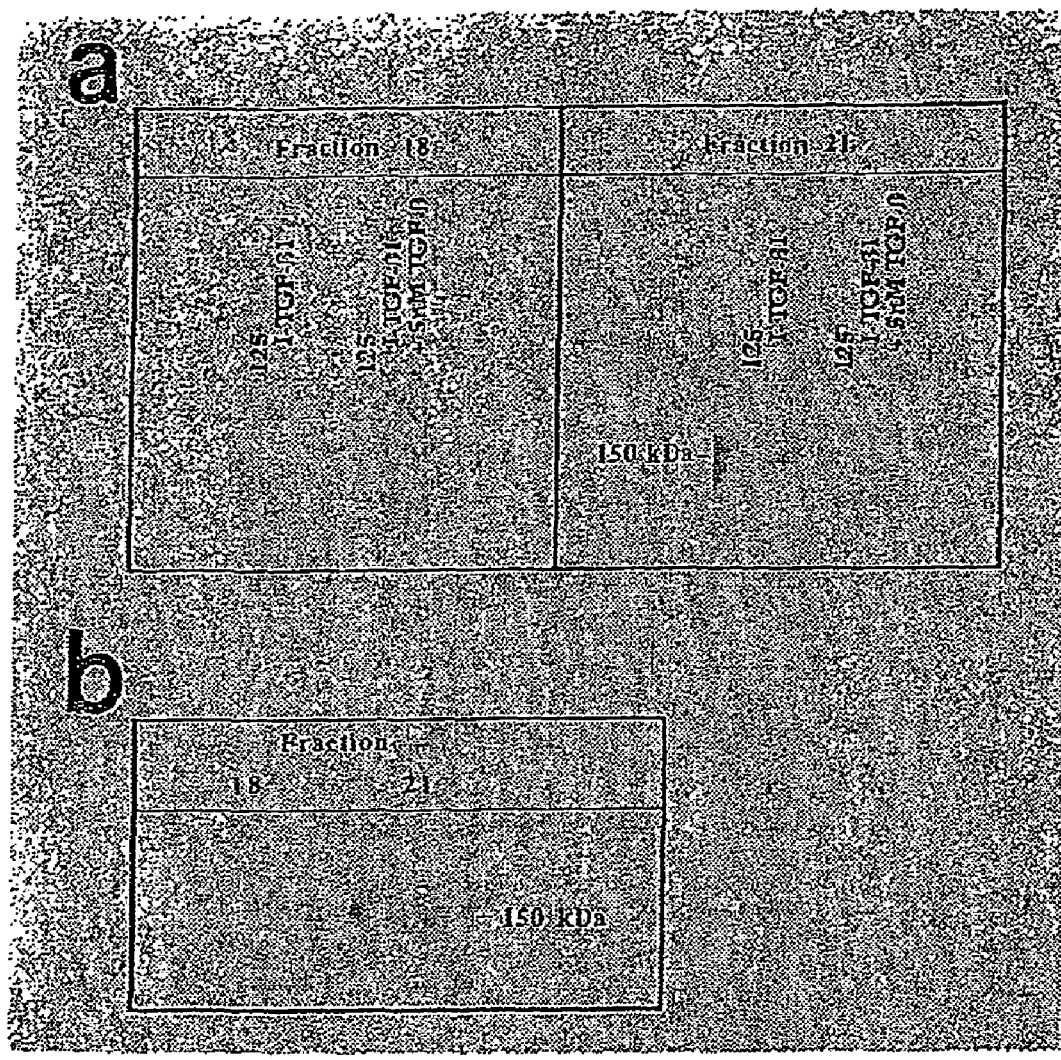
FIG. 4: Identification of a GPI-anchor in r150. Human neonatal keratinocytes were harvested and treated with PIPLC (as described in Materials and Methods). The supernatant containing the GPI-anchored proteins were purified using a TGF-β1 affinity column (see Materials and Methods for details). After the addition of the sample to the column, 0.5 ml fractions were collected during washing and elution. (a) An aliquot from each fraction was affinity labeled with 150 pM of $^{125}$I-TGF-β1 in the absence or presence of excess unlabeled TGF-β1 and samples were analyzed by SDS-PAGE under reducing conditions. Only fraction 21 demonstrated an affinity labeled protein at 150 kDa while in adjacent fractions no 150 kDa band was detectable. Affinity labeling pattern obtained for fraction 21 and fraction 18 are shown. (b) Selected fractions were subjected to SDS-PAGE and transferred to a nitrocellulose membrane, and the samples were immunoblotted with an anti-CRD antibody (Oxford GlycoSystems). A 150 kDa protein was detected in fraction 21 but not in adjacent fractions (fraction 18). Immunoblotting with the anti-CRD antibody was performed twice and the affinity cross-link labeling experiments of soluble r150 was done at least three times.

Keratinocytes were treated with PIPLC and the supernatant was purified on a TGF-β1 affinity column. Analysis of fractions by affinity labeling and SDS-PAGE demonstrated that the fraction 21, but not adjacent fractions (represented by fraction 18) contained a 150 kDa TGF-β1 binding protein (FIG. 4a). The binding of $^{125}$I-TGF-β1 to this protein is specific since it was blocked in the presence of 5 nM TGF-β1. These results confirm that soluble r150 binds TGF-β1.

When the fractions were analyzed by Western blotting with the anti-CRD antibody, it was revealed that fraction 21, but not other fractions contained a protein of relative molecular weight of 150 KDa which was recognized by the anti-CRD antibody. Detection of a 150 kDa protein by the anti-CRD antibody in the absence of chemical cross-linking demonstrates that r150, but not an associated protein, contains a GPI-anchor and, that r150 does not represent two smaller proteins which got inadvertently cross-linked (FIG. 4b). FIG. 4b also shows that r150 was not detectable in an adjacent fraction (fraction 18).

Evidence to Indicate that an Endogenous Phospholipase C Releases r150 in Human Keratinocytes:

Next, whether the anti-CRD antibody can immunoprecipitate r150 and/or coprecipitate the types I and II TGF-β receptors was tested. During the course of these studies, it was observed that the anti-CRD antibody immunoprecipitated r150 from $^{125}$I-TGF-β1 labeled keratinocytes, even in the absence of PIPLC treatment (FIG. 5). This result was reproducible using two different anti-CRD antibodies: the Oxford GlycoSystems antibody that is raised against the CRD epitope of variant surface glycoprotein of *Trypanosoma brucei* (Oxford GlycoSystems), and the antibody specific for the CRD epitope of the porcine membrane dipeptidase (MDP, Broomfield and Hooper, 1993). Since both anti-CRD antibodies are specific for the inositol 1,2-cyclic monophosphate epitope exposed only upon PIPLC treatment, recognition by the two antibodies in the absence of PIPLC treatment indicates that an endogenous phospholipase C cleaved r150 to expose this epitope. The anti-CRD antibody not only precipitated the r150, but also coprecipitated the types I and II receptors. Interestingly, the intensities of the types I and II bands were much stronger than that of the r150 itself. The coimmunoprecipitation of the types I and II receptors demonstrates the heteromeric complex formation of r150 with those receptors (FIGS. 5a, b) which confirms the inventors' previous finding (Tam et al, 1998). The immunoprecipitation with the anti-CRD antibody is specific because the precipitation of labeled complexes is efficiently blocked when the PIPLC hydrolyzed form of MDP which contains the epitope to which the antibody was raised against was included in the reaction (FIG. 5b). These complexes are not detected when the cells were affinity labeled with $^{125}$I-TGF-β2 because r150 has a much lower affinity for TGF-β2 than for the TGF-β1 and TGF-β3 isoforms in these cells (FIG. 5c).

Discussion

The present inventors have shown that a novel 150 kDa TGF-β1 accessory receptor (r150) forms a heteromeric complex with the TGF-β signaling receptors on human keratinocytes (Tam et al. 1998). This accessory receptor was described as GPI-anchored based on its sensitivity to PIPLC. Here it is demonstrated that the GPI-anchor is contained in r150 itself and not on an associated protein and that it binds TGF-β1 with an affinity similar to those of the types I and II TGF-β receptors. In addition, evidence is provided that r150 is released from the cell surface by an endogenous phospholipase C. The most important finding in the present work is that the released (soluble) form of r150 binds TGF-β1 independent of the signaling receptors.

r150 has been characterized as GPI-anchored, based on its sensitivity to phosphatidylinositol specific phospholipase C (PIPLC). In order to prove that the GPI-anchor is present in the r150 itself, it was necessary to rule out other possibilities, namely: (i) r150 is not itself GPI-anchored, but is tightly associated with a protein that is GPI-anchored. Upon PIPLC treatment, the associated GPI-anchored protein is cleaved which results in the release of both the proteins into the supernatant. This has been shown to be the case for lipoprotein lipase which was initially identified as GPI-anchored protein based on its sensitivity to PIPLC; but it was later found that its PIPLC sensitivity was a result of close association with a GPI-linked heparan sulfate proteoglycan (Chajek-Shaul et al, 1989). (ii) r150 is a noncovalently associated complex of two lower molecular weight proteins whose combined molecular weights equate 150 kDa, of which one component is GPI-anchored. During affinity labeling, the two proteins get inadvertently crosslinked by the chemical crosslinker $BS^3$, and thus upon analysis by SDS-PAGE, the cross-linked complex is detected at 150 kDa.

By immunoblotting the purified, soluble form of the r150 with the anti-CRD antibody that can specifically recognize the epitope exposed by the cleavage of the GPI-anchor by PIPLC, the above two possibilities were eliminated. Elution from a TGF-β1 affinity column and detection as a 150 kDa protein in the absence of cross-linking, together with its ability to be recognized by the anti-CRD antibody, prove that r150 has a relative molecular weight of 150 kDa and that the GPI-anchor is contained in r150 itself. There are two GPI-anchored proteins expressed in mammalian tissues that have similar molecular weights as r150. These include an isoform of NCAM (140 kDa) (Rosen et al, 1992) and ceruloplasmin (135 kDa) (Patel and David, 1997). However, immunoprecipitation with antibodies specific to these proteins did not Immunoprecipitate r150 affinity labeled with $^{125}$I-TGF-β1 (data not shown).

Figure 2:
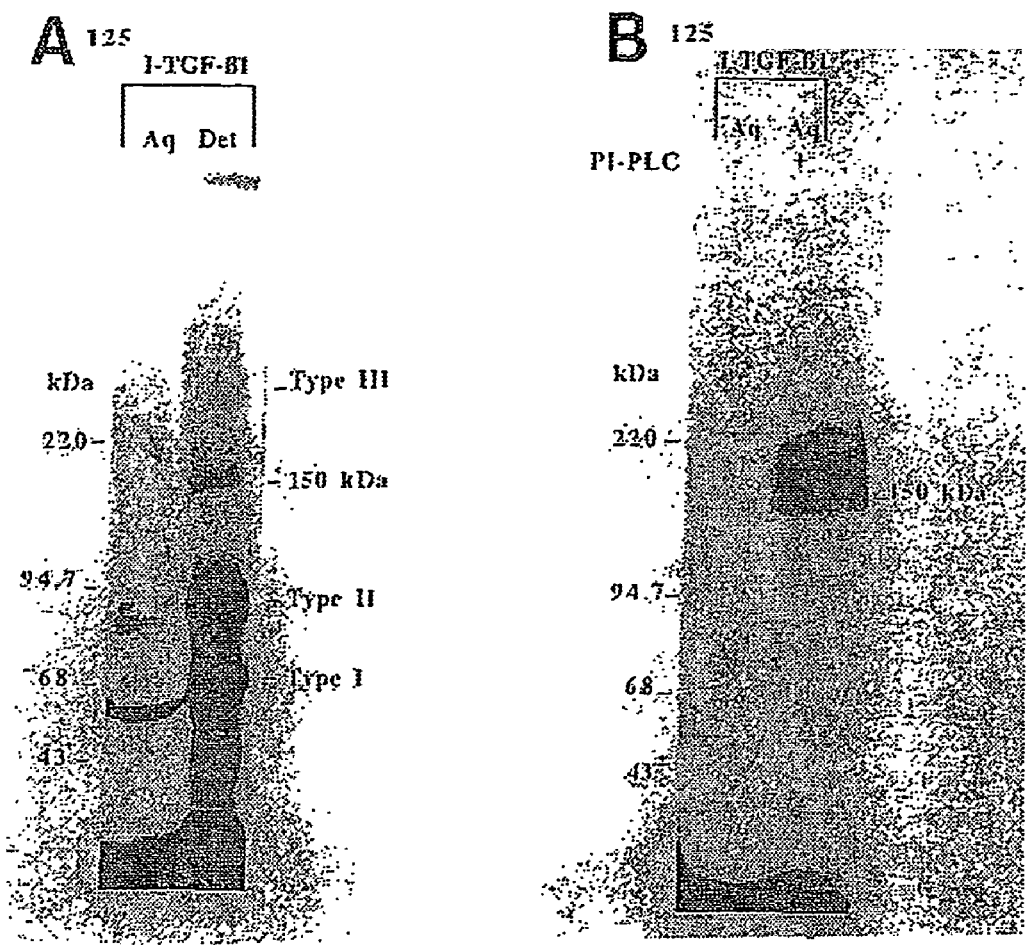
FIG. 2: Temperature induced phase separation in Triton X-114 of TGF-β binding proteins on human neonatal keratinocytes. Keratinocytes affinity labeled with $^{125}$I-TGF-β1 were lysed in 1% Triton X-114. The Triton X-114 soluble material was incubated at 30° C. for 10 minutes followed by centrifugation at room temperature to induce phase separation of the detergent rich phase and the aqueous detergent poor phase. A: An aliquot (20%) from each phase was precipitated with ethanol/acetone, and analyzed by SDS-PAGE under reducing conditions. $^{125}$I-TGF-β1 labeled proteins in the aqueous (Aq) and the detergent rich (Det) phases, representative of three different experiments, are shown. B: The remaining 80% of the detergent phase was utilized to determine the effect of PIPLC treatment on the partitioning of r150 in Triton X-114. The detergent phase was incubated in the absence (−) or presence (+) of 0.6 U/ml of PIPLC followed by temperature induced phase separation and ethanol/acetone precipitation as above, to distinguish between the hydrophilic and amphipathic forms of the proteins. Analysis of the $^{125}$I-TGF-β1 labeled proteins in the aqueous phases of PIPLC treated (+) and untreated (−) samples, by SDS-PAGE under reducing conditions are shown. The results shown are representative of two different experiments.

The soluble r150 is capable of binding to TGF-β1 as shown by affinity labeling of the released protein, and retention on the TGF-β1 affinity column. This suggests that r150 can bind TGF-β in the absence of types I, II and III receptors or an intact membrane. That soluble r150 has the potential to modulate TGF-β binding to its receptors was demonstrated by its ability to inhibit $^{125}$I-TGF-β1 binding to receptors on mink lung cells, Although studies of the inhibition of TGF-β binding to its receptors by r150 used cellular supernatant and not purified r150, this inhibition is most likely due to r150 itself, since there was no measurable TGF-β and neutralizing anti-TGF-β antibody had no effect on this inhibition. The inhibition obtained by the supernatant not treated by PIPLC is likely due to endogenous release of r150 (FIG. 5). As expected, exogenous addition of PIPLC resulted in significantly higher inhibition of binding since more r150 will be released. In addition, r150 is the major TGF-β binder released by PIPLC (FIG. 2). The other potential binder, α2-macroglobulin is unlikely to be released in sufficient quantity during the one hour incubation.

That soluble r150 binds TGF-β1 is reminiscent of what is observed of the ectodomain of type III receptor which has been shown to be released by a not yet characterized mechanism (Lopez-Casillas et al, 1994: Philip et al, 1999). The soluble r150 may act as an antagonist by preventing the binding of TGF-β to the signaling receptors as has been suggested for the soluble type III receptor (Lopez-Casillas et al, 1994). This is supported by our finding which suggests that the soluble r150 inhibits $^{125}$I-TGF-β1 binding to receptors on mink lung cells. But unlike the type III receptor, r150 would antagonize TGF-β1 activity in an isoform specific manner, since it has a low affinity for TGF-β2 and a moderate affinity for TGF-β3, as determined by competition experiments using unlabeled TGF-β isoforms. Furthermore, affinity cross-link labeling of keratinocytes with $^{125}$I-TGF-β1 or $^{125}$I-TGF-β3 did not demonstrate labeling of r150 (data not shown). Recently, a soluble type I receptor has been cloned from a rat kidney cDNA library (Choi, 1999). In contrast to the soluble type III receptor, the soluble type I receptor requires the co-expression of the type II receptor in order to bind TGF-β. However, It appeared to potentiate TGF-β signal transduction and the author has suggested that this potentiation may be due to the stabilization of the heteromeric TGF-β signaling receptor complex. The observation that the soluble r150 can bind the ligand independently of signaling receptors, and modulate TGF-β binding to its receptors (present work), together with fact that the membrane bound r150 binds TGF-β1 and forms heteromeric complex with the type I and II receptors (Tam et al, 1998) raise the possibility that r150 in its membrane bound or soluble form may act as antagonist of TGF-β signaling by regulating ligand availability, or stability of the signaling receptor complex or by directly affecting the signal transduction process.

It is predicted that r150 has dual roles in TGF-β signaling depending on whether it exists as a cell surface anchored protein or as the soluble form. Consequently, a potential mechanism for the regulation of its action would be the hydrolysis of the GPI-anchor. Both the release of the protein from the cell surface and the ability of the soluble form to sequester TGF-β may modulate TGF-β receptor function. Such a possibility in vivo is supported by our observation that an endogenous phospholipase C releases r150 from the cell surface. Since the anti-CRD antibody only recognizes GPI-proteins released from the cell surface by PIPLC, and the cells were not pretreated with PIPLC, the results indicate that there is an endogenous phospholipase C in keratinocytes capable of hydrolyzing r150 at the same site as the PIPLC. The soluble r150 identified in the cellular extract is not due to protease activity since proteolytic cleavage will result in a protein of lower molecular weight. Neither can it be due to failure of cells to add the GPI anchor during synthesis, since the antibody will not recognize that protein. It is of interest to note here that r150 was detectable upon overexposure of films in the PIPLC untreated aqueous fractions obtained by Triton X-114 partitioning (data not shown).

Although the presence of a mammalian PIPLC has not been definitively established, the activity of PIPLC-like enzymes have been implicated in the insulin signaling pathway in rat liver (Satiel, 1996). Furthermore, Movahedi and Hooper (1997) have demonstrated that the insulin stimulated release of GPI-anchored proteins from differentiated 3T3-L1 adipocytes occurs via the action of an endogenous phospholipase C. We choose the general term of phospholipase C for the enzyme that releases the r150 in keratinocytes, since the identity and specificity of the enzyme is not confirmed. Nevertheless, our results suggest that the release of r150 involves an enzyme that hydrolyzes r150 at the same site as PIPLC. PIPLD hydrolyze the GPI-anchor at a different site from PIPLC which does not result in the formation of the inositol 1,2-cyclic monophosphate, and therefore the anti-CRD antibodies that we used in this study cannot recognize PIPLD cleaved proteins (Broomfield and Hooper, 1993). However, PIPLD is expressed in mammalian serum and has been shown to be present in keratinocytes (Xie et al, 1993). Lin et al. (2002), who describe a cell suface antigen named CD109, which appears to be very similar to r150, propose that some GPI anchors are acylated on inositol, because of CD109 sensitivity to phospholipidase D. It is possible that the activity of both enzymes may be involved in regulating the cell surface expression of r150 on human keratinocytes.

GPI-anchored proteins have been reported to bind TGF-β on certain cell lines (Cheifetz and Massague, 1991). More recently, the present inventors reported the presence of GPI-anchored TGF-β binding proteins on early passage human endometrial stromal cells (Dumont et al, 1995) and human skin fibroblasts (Tam and Philip, 1998). Both endometrial stromal cells and skin fibroblasts displayed a 180 kDa GPI-anchored TGF-β1 binding protein and a 65 kDa TGF-β2 binding protein. However, whether the GPI anchor is present in the proteins themselves has not been ascertained for any of them, and the identities of these proteins remain unknown. Interestingly, GPI-anchored proteins have been implicated in the maintenance of the epidermis. When the expression of GPI-anchored proteins was abrogated in the skin by the tissue specific deletion of the PIG-A gene, a gene essential for GPI-protein synthesis, mutants died shortly after birth and their skin was wrinkled and scaly in comparison to that of the wild type (Tarutani et al, 1997). Since TGF-β has an important role in epidermal homeostasis, it is conceivable that the GPI-function which is compromised in these mutants is related to dysregulated TGF-β action due to the loss of r150.

Our results from the competition experiments demonstrating that r150 has high affinity for the TGF-β1 isoform suggest that it is an endogenous ligand for this protein. Whether the membrane bound or soluble form of r150 acts as scavenger receptors regulating ligand availability, whether they participate directly in the modulation of downstream signaling, or if the release of the soluble form is a regulated event in vivo, remain to be determined. Identification of its structure should facilitate resolution of these issues. Elucidating the mechanism by which r150 functions as an accessory molecule in TGF-β signaling in keratinocytes may be critical to understanding the molecular mechanisms underlying the regulation of TGF-β action.

EXAMPLE 2

Creation of Keratynocyte Cell Line Mutants Deficient in GPI Anchor Biosynthesis

Materials and Methods

Cell Culture: An immortalized human keratinocyte cell line, HaCat, was obtained from Dr. P. Boukamp (Hedielberg, Germany). HaCat is a spontaneously immortalized cell line which displays no major differences in differentiation as compared to normal keratinocytes. It possesses a transformed phenotype, but is not tumourigenic (Boukamp et al, 1988). HaCat cells were cultured in D-MEM containing 10% fetal bovine serum, 1 mM sodium pyruvate, 2 mM glutamine and 100 U/ml penicillin, 100 µg/ml streptomycin, and 0.25 µg/ml amphotericin (all Gibco, Burlington, Ontario).

Doubling Time: 8×10⁵ Cells were Seeded at in 60 mm Dishes (Falcon) in Duplicate. At Indicated Times, Cells were Trypsinized and Counted Using a Hemocytometer Affinity labeling of cells: Affinity cross-link labeling techniques were performed as detailed by Dumont et al (1995). Briefly, monolayers of cells were washed with ice cold binding buffer [PBS with Ca2+ and Mg2+, pH 7.4 (D-PBS) containing 0.1% BSA] three times over a thirty minute period. Cells were then incubated at 4° C. for three hours with 100 pM of $^{125}$I-TGF-β1 in the presence or absence of excess non-radioactive TGF-β1 (Austral Biochemical, Genzyme Inc. or R & D Systems respectively). The receptor-ligand complexes were then cross-linked with 1 mM Bis(Sulfocsuccinimidyl)suberate (BS3) (Pierce, Rockford Ill.). After 10 minutes, the reaction was stopped by the addition of 500 mM glycine and further incubated for 5 minutes. The cells were then washed twice with D-PBS and lysed with solubilization buffer (20 mM Tris-HCl, pH 7.4 containing 1% Triton X-100, 10% glycerol, 1 mM EDTA, 10 µM phenylmethylsulfonylfluoride (PMSF), 200 µg/ml BSA, 1 µg/mL leupeptin, 10 µg/ml soyabean trypsin inhibitor, 10 µg/ml benzamide and 2 µg/ml pepstatin). The solubilized material was collected and ⅕ volume of 5× electrophoresis sample buffer (0.25 M Tris-HCl, pH 6.8, 5% SDS, 50% glycerol and trace bromophenol blue) was added. The samples were run on a 1.5 mm-thick 3%–11% SDS-PAGE under nonreducing or reducing (in the presence of 5% β-mercaptoethanol) conditions. Results were analyzed using autoradiography followed by quantitative densitometry. [$^{14}$C] methylated molecular weight protein markers included myosin (H-chain) (200–220 kDa), phosphorylase-b (97.4 kDa), bovine serum albumin (68 kDa), ovalbumin (43 kDa), and carbonic anhydrase (29 kDa), β-lactoglobulin (18.4 kDa) and lysozyme (14.3 kDa) (Gibco or Amersham-Pharmacia Biotech).

Affinity labeling of soluble r150. Confluent monolayers of keratinocytes were treated with 0.6 U/ml of PIPLC for one hour at 37° C. with mild agitation. The supernatant containing the released GPI-anchored proteins was collected and concentrated by Centricon 30 (Amicon). To perform affinity labeling of the soluble form of r150, aliquots of the concentrated supernatant were affinity cross-link labeled with 100–150 pM of $^{125}$I-TGF-β1 in the absence or presence of excess unlabeled TGF-β1 as described above except that the solubilization step was omitted. Binding complexes were analyzed by SDS-PAGE and autoradiography.

Isolation and cloning of a keratinoyte cell line mutated in GPI anchor biosynthesis. The preparation of a keratinocyte cell line mutated in GPI anchor biosynthesis was performed as described by Stevens (1999). HaCat cells grown to 50–60% confluence in a T-75 cm2 flask were treated with 300 µg/ml of ethylmethane sulfonate (EMS) for 24 hours at 37° C. in an atmosphere of 5% CO₂/air. EMS is one of the most common chemical mutagens used to generate cells that are defective in GPI anchor biosynthesis (Sega, 1984). Cells were then allowed to recover for an additional 48 hrs. in normal growth medium. Fluorescence activated cell sorting (FACS) was performed to select those cells which lost the expression of GPI-anchored proteins from their cell surface. Since the identity of the r150 was not known, GPI anchor deficient cells were negatively sorted for another GPI-anchored protein, CD59. Briefly, cells were trypsinized and approximately 2×10⁶ cells were resuspended in one milliliter of FACS buffer (PBS containing 1% FBS) and incubated with 4 µg of fluorescein isothiocyanate (FITC)-conjugated mouse anti human CD59 monoclonal antibody (BD Pharmagin, Mississauga, ON.) or mouse FITC-conjugated IgG$_{2a}$ monoclonal antibody for 45 minutes on ice. After the incubation, the cell pellet was washed once and resuspended in one milliliter of FACS buffer. Propidium iodide (3 µg/ml) (Sigma) was added to the cells prior to sorting which was performed using the FACS Vantage (Becton Dickinson). Cell sorting was repeated two additional times. At the third and final FACS, a single CD59 negative cell was seeded into each well of a 96 well plate using the FACS Vantage automated cell deposition unit. In the surviving clones, the cell surface expression of CD59 was analyzed by flow cytometry to determine which cells expressed deficient levels of GPI-anchored proteins. Affinity cross-link labeling with $^{125}$I-TGF-β1 was performed to characterize the expression of the r150.

Luciferase assay. The p3TP-Lux and CMVβ-galectosidase (CMVβB-gal) gene constructs were gifts from Dr. O'Connor-McCourt (Biotechnology Research Institute, Montreal, Quebec). The p3TP-Lux construct contains three tetradecanoyl phorbol acetate (TPA)-responsive elements and TGF-β responsive elements from the PAI-1 promoter fused to the luciferase reporter gene (Wrana et al, 1992). Briefly, 2.5×10⁵ HaCat cells, plated in a 12 well plate, were transiently transfected with 1 µg each of p3TP-Lux and CMVβ-gal cDNAs using the Superfect reagent as recommended by the manufacturers (Qiagen, Mississauga, Ontario). The cells were allowed to recover overnight and were serum starved for three to four hours prior to treatment with various doses of TGF-β1 or TGF-β2 for the indicated times (Austral Biochemicals). For the luciferase assay, cells were solubilized in 150 µl of lysis buffer (BD Pharmagin, Mississauga, Ontario) for 30 minutes at 4° C. In an opaque 96 well plate, 45 µl of lysate was added to 10 µl of ATP cocktail [0.1 M ATP, 0.5 M KH₂PO₄ (pH 7.8), 1 M MgCl₂]. Luciferase activity was measured upon addition of 100 µl of 25 mM luciferin (Roche Dagnostics) in 0.1 M KH₂PO₄ (pH 7.8) using an EG & G Berthold Microplate Luminometer. For the β-galactosidase assay, in a 96 well plate, 5 µl of the lysate was added to 100 µl of β-gal buffer (60 mM Na₂HPO₄, 40 mM NaH₂PO₄, 10 mM KCl, 1 M MgCl₂ and 50 mM β-merocaptoethanol) containing 1.5 ng/ml of ortho-nitrophenyl β D-galactopyranoside (ONPG) (Sigma). The samples were incubated at 37° C. until a satisfactory colour reaction was obtained. The colour reaction was then measured at 420 nm using a spectrophotometric plate reader (Molecular Dynamics, Sunnyvale, Calif.). Values were derived from transfections performed in duplicate or triplicate and all experiments were performed at least three times.

In vitro kinase assay. HaCat and GPI anchor mutated cells grown in T-75 cm 2 flasks were serum starved overnight and left untreated or treated with 100 pM TGF-β1 for 20 minutes at 37° C. The cells were scraped in 200 µl of lysis buffer (50 mM Tris pH 7.5, 150 mM NaCl, 50 mM NaF, 50 mM β-glycerophosphate, 1 mM sodium orthovanadate, 1 mM DTT. 5 mM EDTA pH 8.0, 1% NP-40, 10% glycerol, 10 µM PMSF, 200 µg/ml BSA, 1 µg/mL leupeptin, 10 µg/ml soyabean trypsin inhibitor, 10 µg/ml benzamide and 2 µg/ml pepstatin) and further incubated in the lysis buffer for 30 minutes on ice. The cells were pelleted and the solubilized extract was precleared with 40 µl of protein A Sepharose slurry (Amersham-Pharmacia-Biotech) and 3 µg/ml of polyclonal rabbit IgG antibody for two hours at 4° C. One mg of protein was incubated with 3 µg/ml of anti-type II TGF-β receptor antibody (Santa Cruz) overnight at 4° C. The immune complexes were then incubated with 50 μl of protein A Sepharose slurry for two hours at 4° C. The beads were pelleted and washed three times with 0.5 ml of lysis buffer and one time with 0.5 ml of kinase buffer [50 mM Tris (pH 7.4), 10 mM $MgCl_2$, 1 mM $CaCl_2$]. After the last wash, 20 μl of kinase buffer was added to the pellets and incubated with 10 μCi of gamma$^{32}$P-ATP (NEN) for 30 minutes at 30° C. The reaction was halted by the addition of 5 μl of 5× sample buffer (0.25M Tris-HCl, pH 6.8, 5% SDS, 50% glycerol and trace bromophenol blue) containing 5% β-mercaptoethanol and boiled for 5 minutes. The extracts were separated on a 7.5% polyacryalamide SDS-PAGE gel and analyzed by autoradiography.

Western blotting of phosphorylated Smad2. HaCat and GPI anchor mutated cells were grown in 60 mm dishes (Falcon) to 70–80% confluency and serum starved overnight. Cells were washed with PBS and were treated with with various doses of TGF-β1 or TGF-β2 for the indicated times at 37° C. The cells were solubilized with 500 μl of lysis buffer for at least 30 minutes at 4° C. with mild agitation. The cell lysates were collected and centrifuged for 10 minutes at 12 000×g. The protein concentration of the each sample was normalized to 50 μg using the BioRad protein assay kit as recommended by the manufacturers. ⅕ volume of 5× electrophoresis reducing sample buffer was added to the sample and boiled for 5 minutes. The samples were separated on a 7.5% SDS-polyacrylamide gel and transferred to a nitrocellulose membrane. The membrane was blocked for at least three hours to overnight in blocking buffer [TBS-T buffer: 30 mM Tris (pH 7.5), 150 mM NaCl, 0.05% w/v Tween 20, containing 5% w/v of skim milk powder]. The blot was then incubated for 60 minutes at room temperature with the PS2 antibody (1:2000 in TBS-T buffer) which recognizes the phosphorylated C-terminus of Smad2 (a gift from Dr. S. Souchelnytskyi, Uppsula, Sweden). The blot was then washed in TBS-T buffer and incubated for 45 minutes at room temperature with a secondary anti-rabbit antibody conjugated to horseradish peroxidase (HRP) (1:5000) (Pierce, Rockford, Ill.). The membrane was then subjected to chemiluminescence analysis (ECL) as detailed by the manufacturers (Amersham-Pharmacia-Biotech). In order to determine equal protein loading, membranes were immunoblotted with a goat polyclonal anti-Smad2 antibody (Santa Cruz) that is raised against a peptide near the N-terminus, or a rabbit polyclonal anti-STAT3 antibody (Santa Cruz) which recognizes a peptide mapping at the C-terminus.

Results

Figure 6:
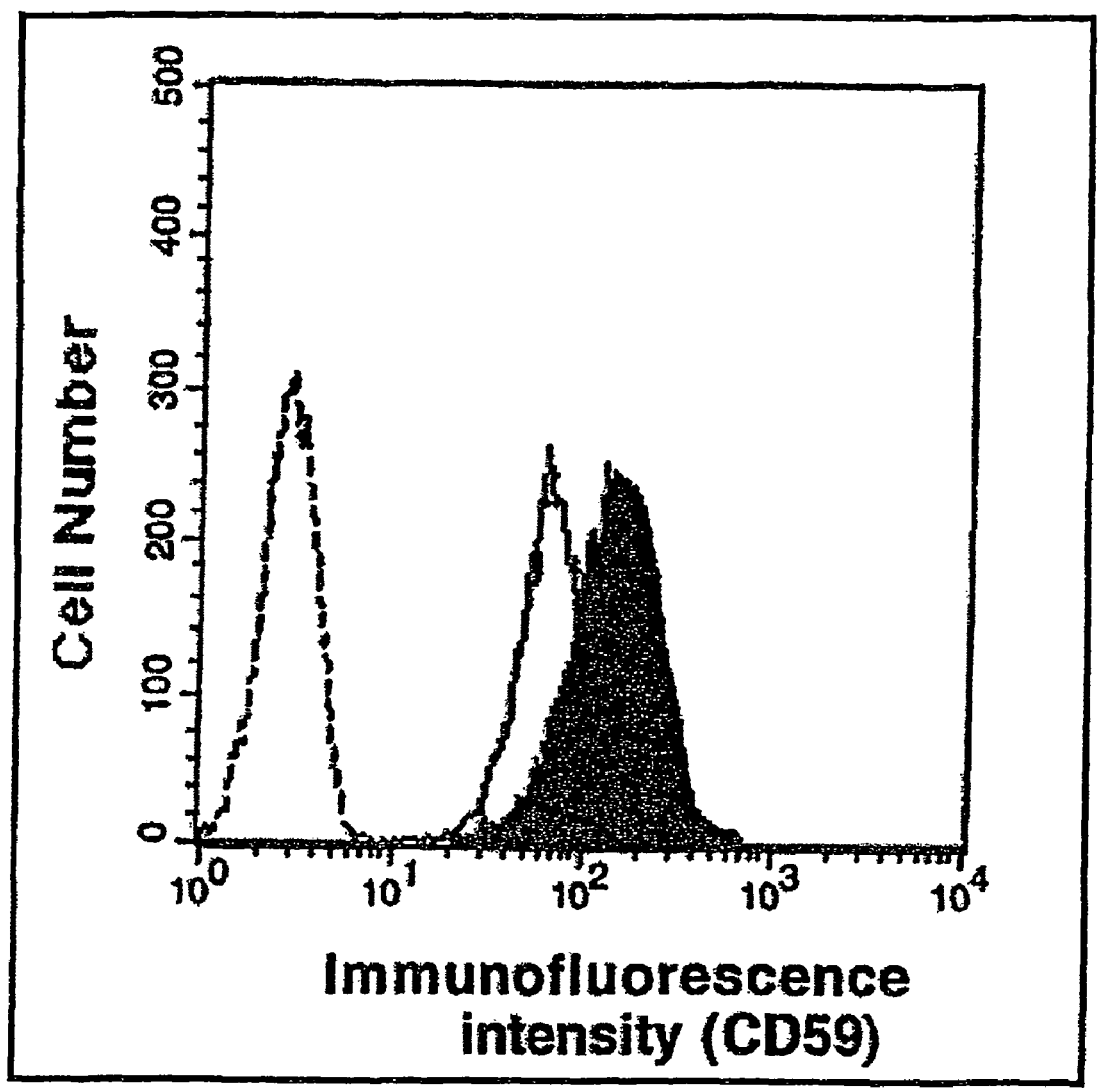
FIG. 6A: Expression of CD59 is decreased in keratinocytes mutated in GPI anchor biosynthesis. A representative histogram of the expression of CD59 in a GPI anchor deficient clone, GPI M (white columns) and parental HaCat cells (black columns) as assessed by flow cytometry using an anti-CD59-FITC labeled antibody. The immunoflourescence intensity of CD59 in the GPI anchor deficient cells was approximately 50% to that of the HaCat cells. The control performed in the absence of antibody is also included (doted peak). Flow cytometry was performed at least three times.
FIG. 6B: Cell surface expression of r150 is markedly decreased in GPI anchor mutated cells. Confluent monolayers of HaCat and GPI M cells were affinity labeled with 100 pM $^{125}$I-TGF-β1. Solubilized cell extracts were analyzed on SDS-PAGE under reducing conditions.

Isolation and Cloning of a Cell Line Mutated in GPI Anchor Biosynthesis:

HaCat cells were treated with 300 μg/ml of ethylmethanesulfonate (EMS) for 24 hours as described in "Materials and Methods." EMS is an ethylating agent that has been used to cause mutagenesis of genes, including those involved in the biosynthesis of the GPI anchor (Sega, 1984; Stevens, 1999). Because the identity of the r150 is not known, another GPI-anchored protein that is strongly expressed in human keratinocytes was used in the cloning of GPI anchor deficient cells. CD59 is a 21 kDa GPI-anchored protein that is expressed in keratinocytes and is an inhibitor of the membrane attack complex (Venneker et al, 1994; Pasch et al, 1998). After EMS treatment, cells were stained with an anti-CD59 antibody conjugated to FITC and negatively sorted. Cells selected into the CD59 negative population were cloned using the FACS Vantage automated cell deposition unit. Ten clones survived and were reanalyzed for CD59 expression by flow cytometry. Two clones displayed decreased expression of CD59 on their cell surface and were presumed to be mutated in GPI anchor biosynthesis (termed GPI M and GPI M1). FIG. 6A demonstrates the flow cytometric analysis of parental HaCat cells as compared to GPI M cells. Though the expression of CD59 was not completely abolished in the GPI M cells, the immunofluorescence intensity of CD59 was analyzed to be approximately half that of HaCat cells (56.3%+/−7.4, p<0.0006). Similar results were obtained with the GPI M1 cells.

Figure 6B:
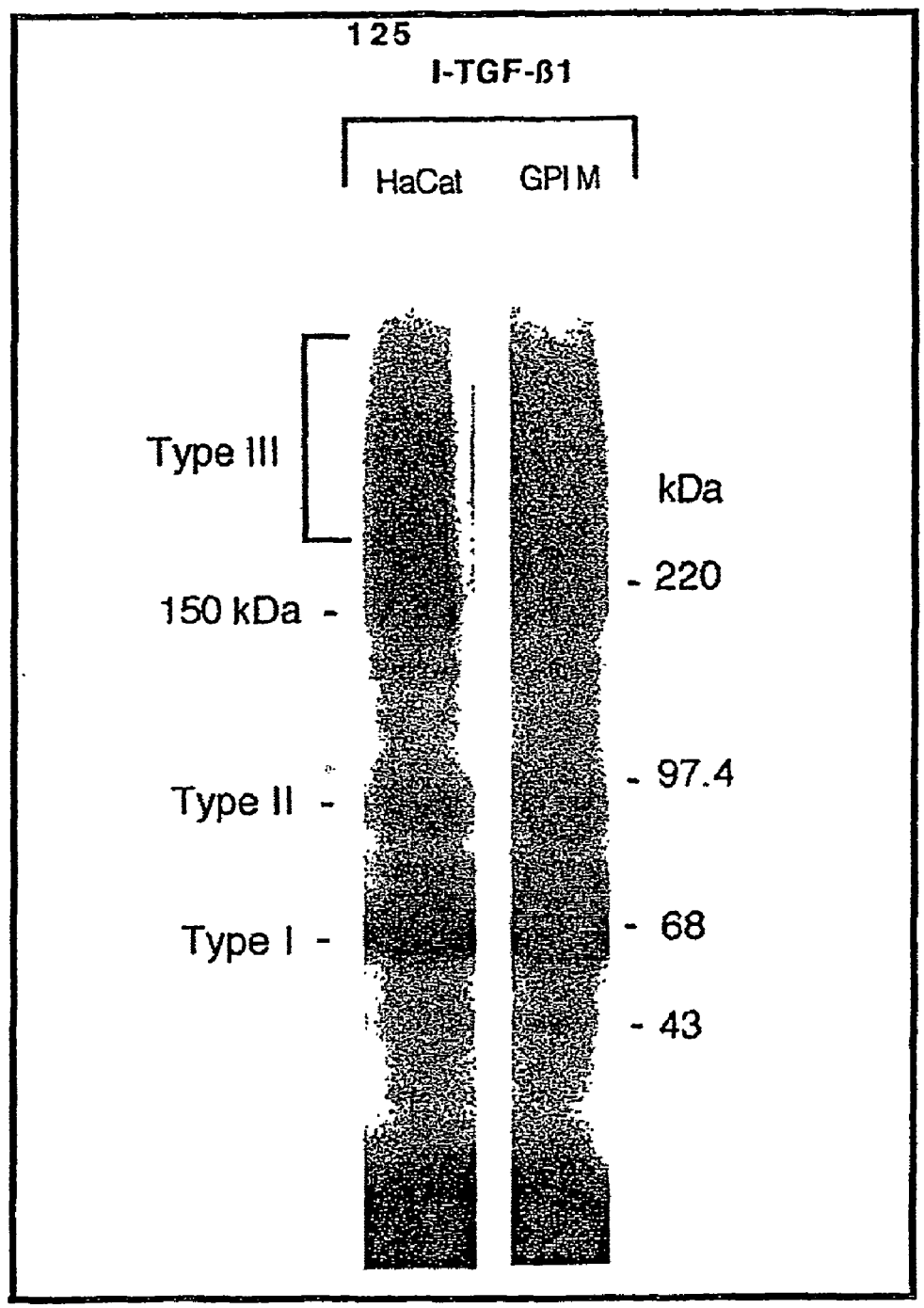

In order to ascertain that the GPI anchor mutated cells are deficient in r150, affinity labeling with $^{125}$I-TGF-β1 was performed. As demonstrated in FIG. 6B, GPI M cells exhibit a significant loss of r150 on their cell surface as compared to HaCat cells. The expression of the types I, II and III receptors and their binding to $^{125}$I-TGF-β1 are unaffected in the GPI M cells and appear identical to that of parental HaCat cells.

Figure 7:
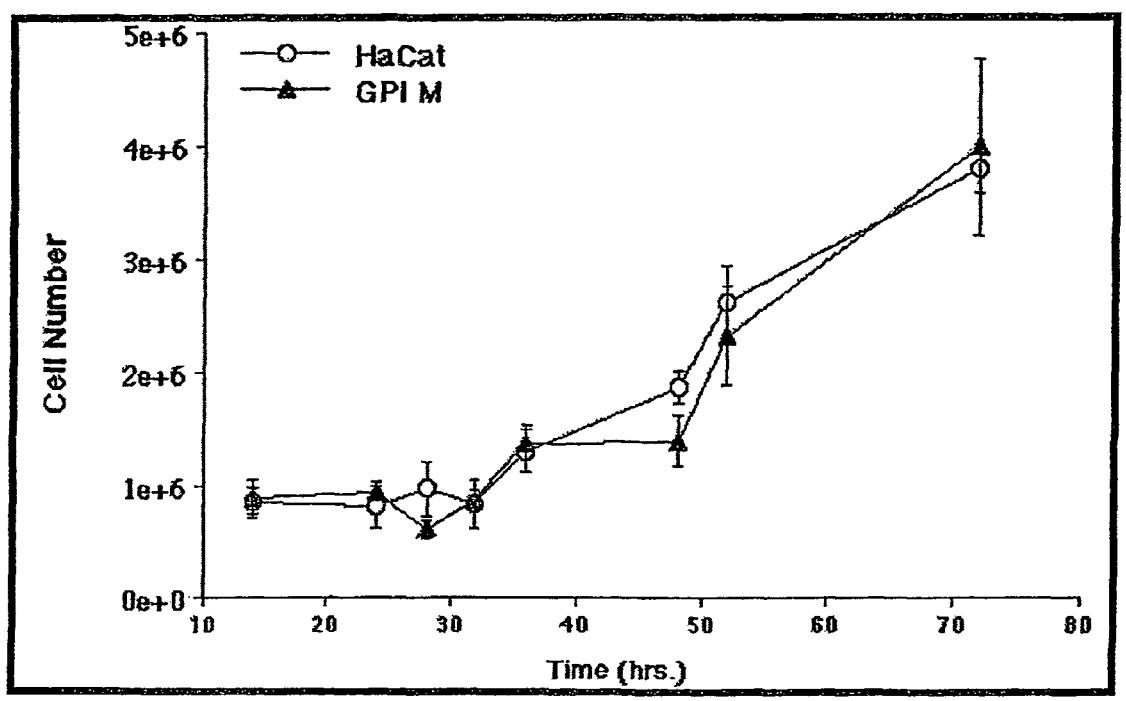
FIG. 7A: Doubling time curves of HaCat and GPI anchor mutated cells. HaCat and GPI M cells were seeded at 8.0×10$^5$ cells in 60 mm dishes in duplicate and the cell number for each was determined at 14, 24 28, 32, 36, 48, 52 and 72 hours using a heamacytometer.
FIGS. 7B and C: The cellular morphology of GPI anchor mutated cells is identical to that of HaCat cells. Microscopic representation (10× magnification) of HaCat (FIG. 7B) or GPI M cells (FIG. 7C) under normal culture conditions.
Figure 7:
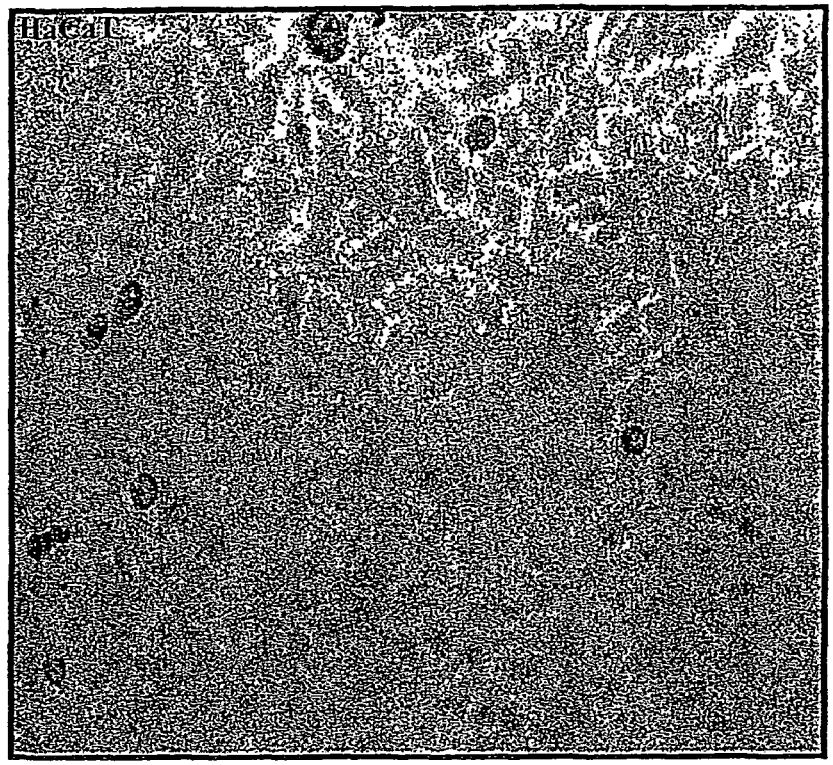
Figure 7:
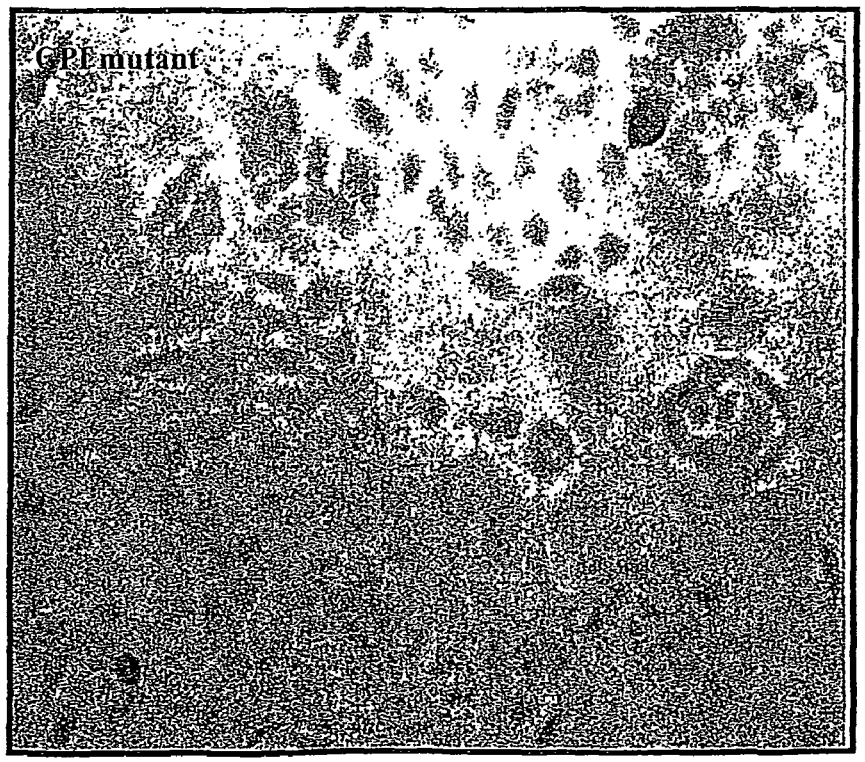

Cell Growth and Morphology are Unchanged in GPI Anchor Mutated Cells:

A deficiency or loss of the cell surface expression of GPI-anchored proteins as a result of EMS mutagenesis is reported not to affect cell morphology or cell cycle progression (Stevens, 1999). In order to confirm that cell growth was not altered in the GPI anchor deficient keratinocyte cell line, the doubling time of these cells was determined. As seen in FIG. 7A, GPI M cells display a similar doubling time (approximately 16 hrs.) as the parental HaCat cells. In addition, the cellular morphology of GPI M cells (FIG. 7C) is unchanged to that of the HaCat (FIG. 7B).

r150 Negatively Modulates TGF-β Stimulated Transcription:

TGF-β1 induced transactivation of the p3TP-Lux reporter construct in GPI M and HaCat cells was then evaluated. As demonstrated in FIG. 8A, upon treatment with 10 pM TGF-β1 for 4 hours, the GPI M cells display an approximately 30% higher fold increase of luciferase activity, as compared to HaCat cells (p<0.05). In response to 100 pM TGF-β1, the difference between the GPI M and HaCat cells rises to 50% (p<0.003). Interestingly, the fold induction in the HaCat cells with 10 pM and 100 pM TGF-β1 treatment remain similar to each other (3.3 and 3.9 respectively), while the GPI M cells display a dose response, demonstrating fold increases of 4.9 and 8.4 respectively.

Figure 8:
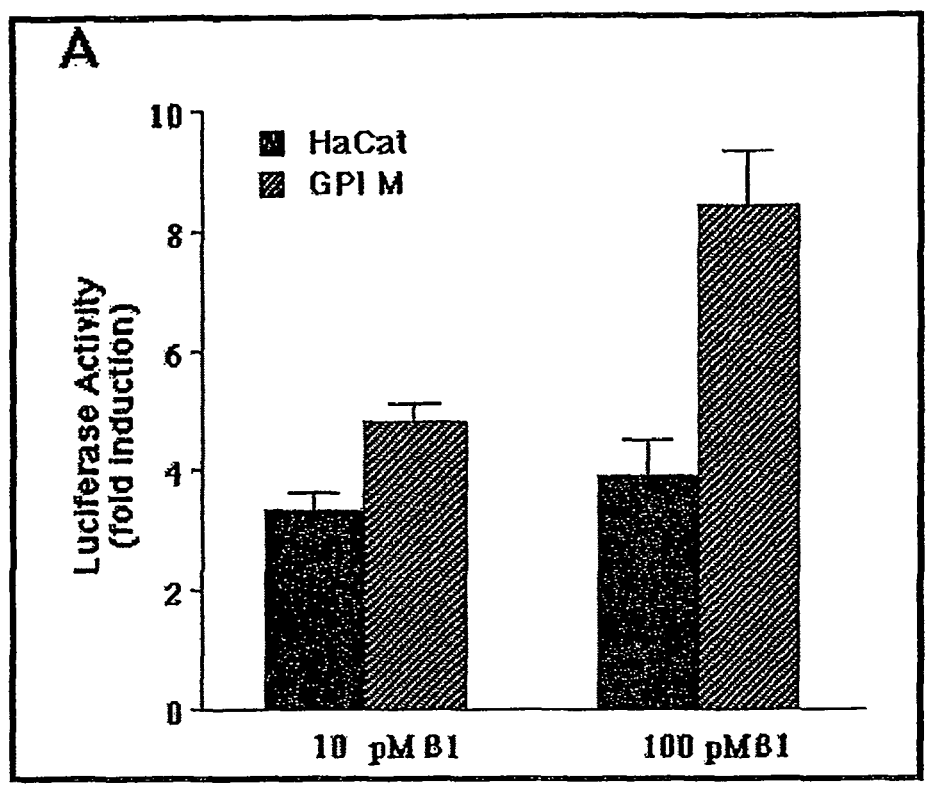
FIGS. 8A and B: Enhanced TGF-β stimulated transcriptional response in GPI anchor mutated cells. HaCat and GPI M cells were transiently transfected with 1 μg of p3TP-Lux reporter gene construct and were left untreated or treated under serum free conditions with the indicated concentrations of TGF-β1 for 4 hrs (FIG. 8A) or 16 hrs (FIG. 8B). The luciferase activity was normalized to β-galactosidase activity expressed from a co-transfected CMVβgal plasmid. The data is representative of at least three independent experiments. Error bars represent standard deviation.
Figure 8:
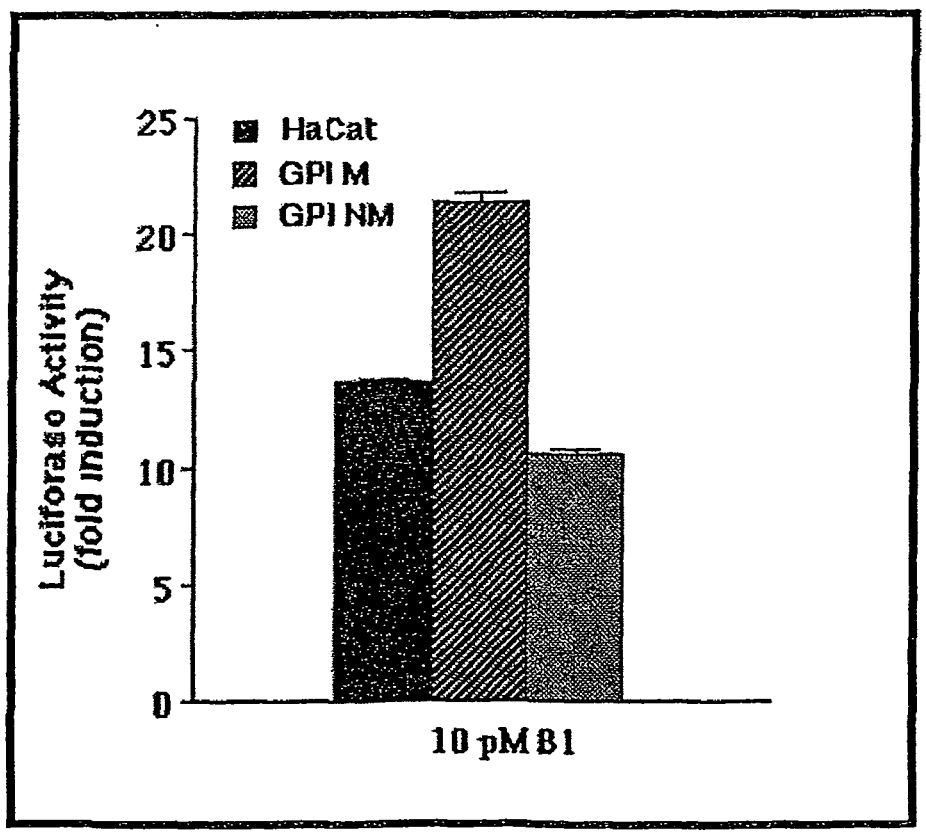

Upon 16 hours of TGF-β1 treatment, the GPI M cells display a markedly enhanced response to 10 pM and 100 pM TGF-β1 compared to the parental HaCat (FIG. 3B). Also, a dose response to the 10 pM and 100 pM TGF-β1 are evident for both cell types. A clone of HaCat cells that was subjected to the same cloning procedure as the GPI M cells, but not mutated in GPI anchor biosynthesis (GPI NM) was included as a control. Upon 10 pM TGF-β1 treatment, GPI M cells display the highest fold induction of 21.4 compared to the 13.6 and 10.6 increases demonstrated by the HaCat and GPI NM cells (p<0.005 for GPI M vs HaCat). Similarly, in response to 100 pM TGF-β1, the fold induction exhibited by the GPI M cells is approximately twice that of HaCat and GPI NM cells (91.2 compared to 50.2 and 51.3 respectively) (p<0.01 for GPI M vs HaCat). In response to 100 pM TGF-β2, there is no significant difference in the stimulation of luciferase activity among the GPI M, HaCat and GPI NM cells (FIG. 8C).

Figure 9:
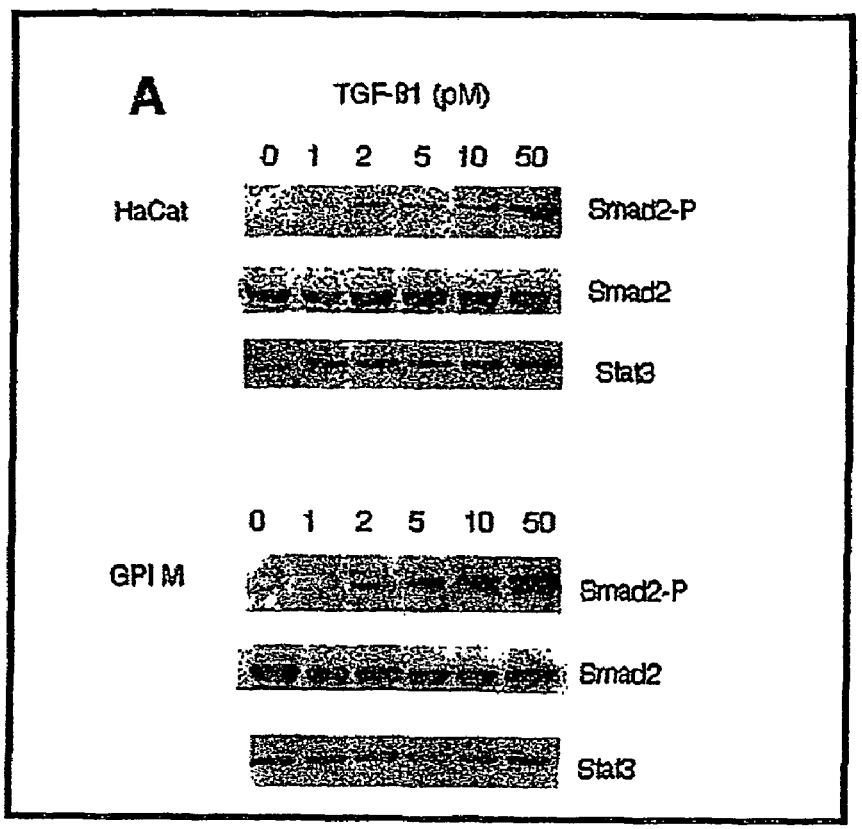
FIGS. 9A and B: GPI anchor mutated cells display enhanced responses at low doses of TGF-β1. HaCat and GPI M cells were left untreated or treated with the indicated doses of TGF-β1 (FIG. 9A) and TGF-β2 (FIG. 9B) under serum free conditions for 20 minutes. Immunoblotting was performed using a rabbit polyclonal antibody specific to the phosphorylated form of Smad2. Immmunoblotting was repeated with an anti-Smad2 antibody that recognizes total Smad2 (unphosphorylated and phosphorylated forms) or an anti-STAT3 antibody to demonstrate equal protein loading. This data is representative of three different experiments.
Figure 9:
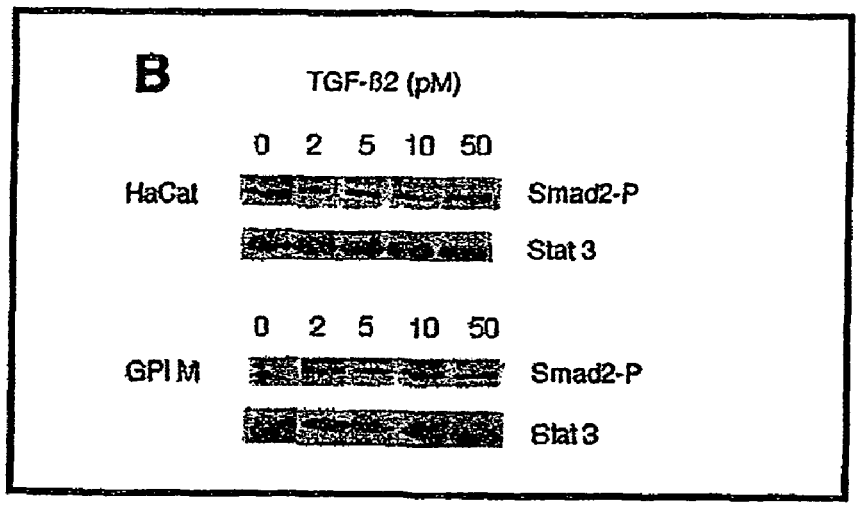

GPI Anchor Mutated Cells Display Enhanced Smad2 Phosphorylation at Low Doses of TGF-β1:

In order to determine if the loss of r150 had any affect on the endogenous phosphorylation of Smad2, HaCat and GPI M cells were treated with 1–50 pM of TGF-β1 for 20 minutes and immunoblotting was performed with an antibody raised against the phosphorylated form of Smad2. As demonstrated in FIG. 9A, GPI M cells display an enhanced level of Smad2 phosphorylation as compared to the parental HaCat. In both cell types, Smad2 phosphorylation becomes detectable at 2 pM TGF-β1 and increases in a dose dependent fashion. However, GPI M cells exhibit an enhanced Smad2 phosphorylation in response to low (2 and 5 pM), intermediate (10 pM) and higher (50 pM) doses of TGF-β1 in comparison to the HaCat cells. Immunoblotting with an anti-Smad2 antibody that detects both the unphosphorylated and phosphorylated forms of Smad2 not only demonstrates equivalent protein loading, but shows that the enhanced Smad2 phosphorylation is not a result of an increased expression of total Smad2. Equal protein loading of HaCat and GPI M cell lysates is also confirmed upon immunoblotting with an anti-STAT3 antibody. Enhanced Smad2 phosphorylation in the GPI M cells is not evident in response to TGF-β2, as HaCat and GPI M cells appear to demonstrate the same weak pattern of TGF-β2 induced Smad2 phosphorylation (FIG. 9B).

Figure 10:
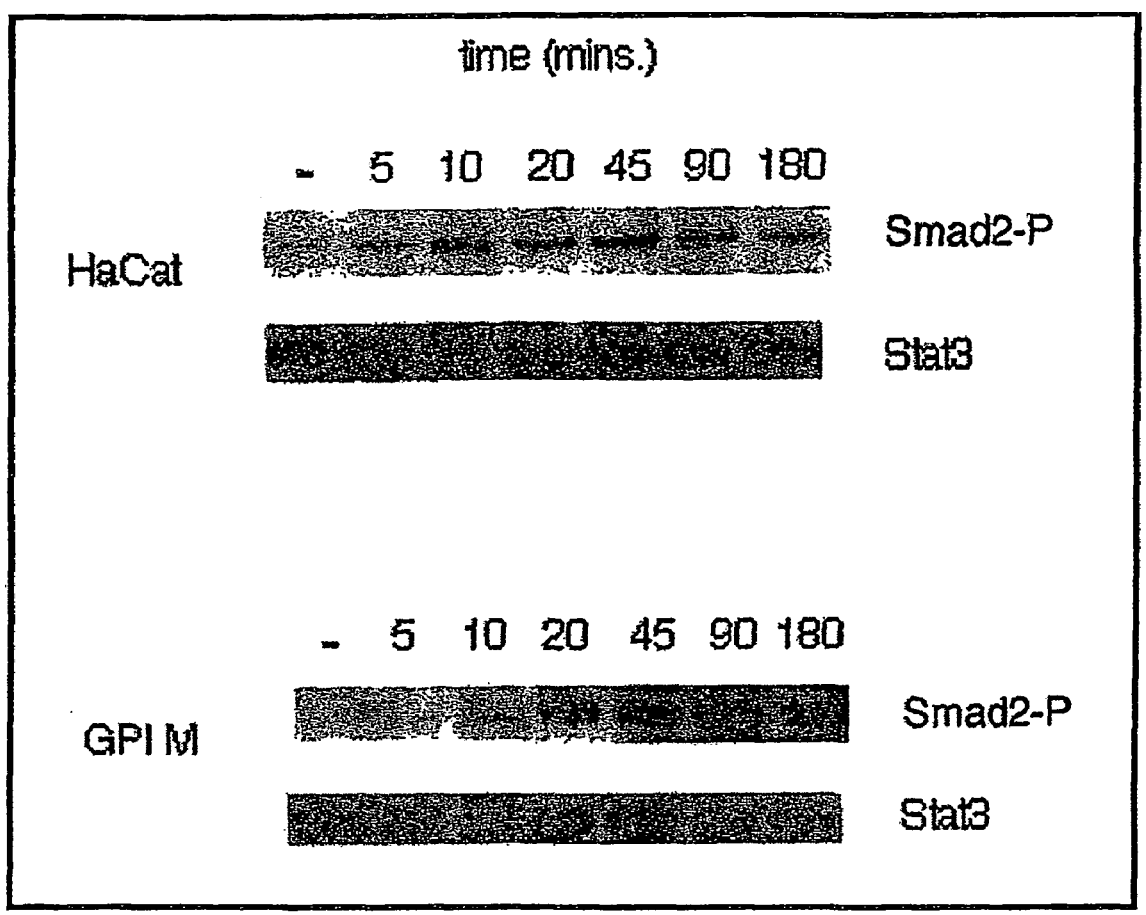
FIGS. 10A, B and C: Elevated Smad2 phosphorylation is sustained in GPI anchor mutated cells. HaCat and two GPI anchor deficient clones GPI M (FIG. 10A) and GPI M1 (FIG. 10B) or a keratinocyte clone that was not GPI anchor mutated, GPI NM (FIG. 10C) were treated with 100 pM TGF-β1 for the indicated times. The control lane (−) received no TGF-β1 treatment. Imnnunoblotting was performed using a rabbit polyclonal antibody specific to the phosphorylated form of Smad2. The same nitrocellulose membrane was reblotted and with an anti-STAT3 antibody to demonstrate equal protein loading. This data is repesentative of at least three different experiments.
Figure 10:
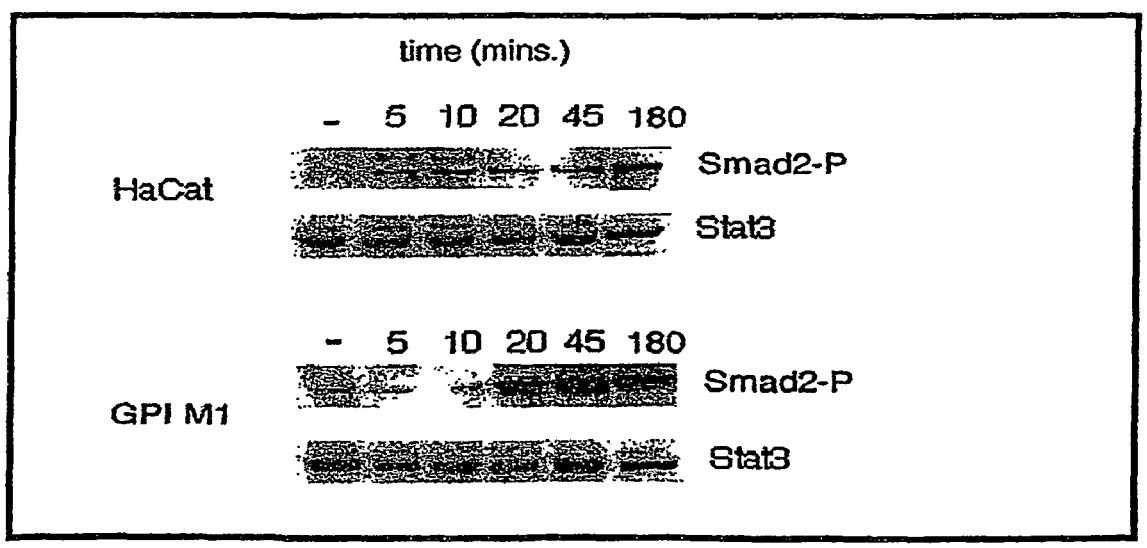
Figure 10:
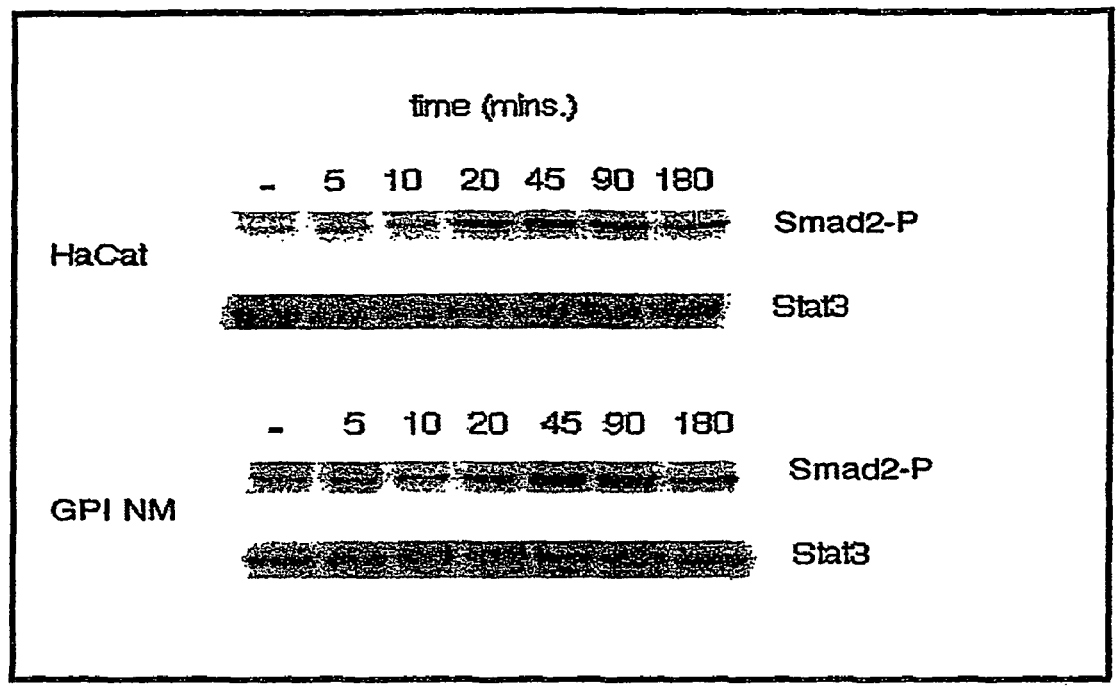

Elevated Smad2 Phosphorylation is Sustained in GPI Anchor Mutated Cells:

Was further examined if the GPI anchor deficient cells exhibit enhanced Smad2 phosphorylation as compared to HaCat cells upon prolonged exposure to TGF-β1 (FIG. 10). In response to 100 pM TGF-β1 for the indicated times, maximal stimulation of Smad2 phosphorylation in HaCat cells is achieved at 10 minutes and maintained for 180 minutes. In GPI M cells, Smad2 is maximally phosphorylated between 45–90 minutes, followed by a moderate decrease in its phosphorylation at 180 minutes. In comparison to HaCat cells, the GPI M cells display a significantly elevated Smad2 phosphorylation which is evident at 45 minutes and is sustained until 180 minutes. The second GPI anchor mutated clone (GPI M1) also exhibits enhanced Smad2 phosphorylation in response to TGF-β1 (FIG. 10B). In this experiment, the GPI M1 cells display an elevated level of TGF-β1 induced Smad2 phosphorylation as compared to HaCat cells starting at 20 minutes and is sustained until 180 minutes. On the other hand, Smad2 phosphorylation in GPI NM control cells is similar to that of HaCat cells for all the time periods studied in response to TGF-β1 (FIG. 10C). Immunoblotting with the anti-STAT3 antibody demonstrates equal protein loading of the cell lysates. These results indicate that only the GPI anchor deficient cells (GPI M and GPI M1) exhibit enhanced TGF-β1 stimulated phosphorylation of endogenous Smad2 as compared to the parental HaCat cells.

Autophosphorylation of Type II Kinase in HaCat and GPI Anchor Mutated Cells.

Since r150 can interact with the TGF-β signaling receptors in human keratinocytes, and TGF-β induced Smad2 phosphorylation is enhanced in GPI anchor deficient cells, we analyzed for alterations in the autophoshorylated state of the constitutively active type II receptor kinase using the in vitro kinase assay. As demonstrated in FIG. 11, GPI M cells do not display any marked differences in type II receptor kinase phosphorylation as compared to the parental HaCat cells in either the absence or presence of 100 pM TGF-β1. The moderate decrease in TGF-βRII kinase autophosphorylation displayed by the GPI M cells, as compared to HaCat cells, did not occur in a reproducible manner.

Discussion

A keratinocyte cell line mutated in GPI anchor biosynthesis (GPI M) derived by CD59 negative based FACS from HaCat cells treated with EMS (Stevens, 1999) was created and isolated. In comparison to the parental HaCat, these cells demonstrate a significant loss in expression of the novel GPI-anchored TGF-β1 accessory receptor, r150, from their cell surface. There is no alteration in TGF-β types I and II receptor expression, nor in their abilities to bind TGF-β1. In addition, GPI M cells do not show any differences in cellular morphology or doubling time. However, these cells display an enhanced transactivation of the TGF-β responsive p3TP-Lux reporter gene construct as compared to HaCat cells. Furthermore, GPI M cells display an enhanced Smad2 phosphorylation in response to TGF-β1 treatment in a time and dose dependent manner. Taken together, the present work indicates that the novel accessory receptor, r150 acts as a negative modulator of TGF-β action in human keratinocytes.

In the isolated GPI anchor deficient cell lines, the cell surface expression of CD59 is still detectable by flow cytometry, thus indicating that the cells do not display a complete abrogation of GPI-anchored proteins. However, a decrease in immunofluorescence intensity of approximately 50% exhibited by the GPI M cells is comparable to the loss of GPI-anchored proteins from the cell surface after PIPLC treatment (Screaton et al, 2000). In addition, $^{125}$I-TGF-β1 affinity cross-link labeling of GPI M cells demonstrate a significant loss of r150 from their cell surface as compared to HaCat cells. That GPI anchor biosynthesis is not completely abolished in these cells is likely due to the presence of GPI anchor biosynthetic genes that are resistant to EMS mutagenesis (Stevens et al, 1996). The present inventors are the first to report of the isolation of a GPI anchor deficient keratinocyte cell line.

EMS is an ethylating agent that has been used to cause mutagenesis of genes, including those involved in the biosynthesis of the GPI anchor (Sega, 1984; Stevens, 1999). There is a mutation frequency of approximately one in a million cells upon treatment of mammalian cells with this mutagen in the dose range of 100–400 μg/ml. Hence, to "knock out" two copies of a gene, the frequency becomes 1 000 000×1 000 000 (Boyd and Massague, 1989; V. Stevens, personal communication). At this low frequency, the assumption is made that there is one mutation in each cell that is selected and cloned. For example, using this methodology, Stevens et al (1996) created a Chinese Hamster Ovary (CHO) cell line mutated in GPI anchor biosynthesis. This cell line has been recently used to study the role of GPI-anchored proteins in the development of Alzheimer's disease (Sambamurti et al, 1999) and in the "cross-talk" between caveolae and GPI-enriched lipid microdomains (Abrami et al, 2001). In addition, prior to the cloning of the TGF-β receptors, EMS mutagenesis was used to create the mutant Mv1Lu cell lines known as "R" and "DR" which do not express the type I and types I and II TGF-β receptors respectively (Boyd and Massague, 1989; Laiho et al, 1990). These TGF-β unresponsive R and DR mutant cell lines continue to be used to delineate components of the TGF-β signaling pathway (Massague, 1998). Therefore, the main drawback of the above model is that the expression of all GPI-anchored proteins may be affected. Thus, it is possible that the loss of other GPI proteins besides r150 may have an impact on TGF-β signaling. However, none of the presently identified mammalian GPI-anchored proteins can bind TGF-β or are implicated in TGF-β signaling (for review, Low, 1989; Turner. 1994). The novel 150 kDa accessory receptor is the strongest candidate because it appears to be the only GPI-anchored protein that binds to TGF-β1 in keratinocytes. Furthermore, it has the potential to modulate TGF-β signaling through its interaction with the types I and II TGF-β receptors. Other GPI-anchored TGF-β binding proteins such as 180 kDa TGF-β1 binding protein and two GPI-anchored TGF-β2 binding proteins at 60 kDa and 140 kDa were identified in certain cell lines including a human asteosarcoma cell line (Cheifetz and Massague, 1991). In human fibroblasts, the present inventors identified a 180 kDa GPI-linked TGF-β1 binding protein, as well as a 65 kDa GPI-anchored TGF-β2 binding protein which do not interact with the types I and II receptors (Dumont et al, 1995; Tam and Philip, 1998). However, early passage human keratinocytes and HaCat cells do not appear to express any of GPI-anchored TGF-β binding complexes with the above mentioned relative molecular weights (Chapter 4; Tam et al, 1998). Together, it is likely that the observed differences in TGF-β1 induced cellular responses exhibited by the GPI M cells is due to the loss of r150.

The GPI anchor deficient cells display an increased transactivation of the PAI-1 promoter driven luciferase gene construct upon 4 and 16 hours of TGF-β1 treatment. The fold induction demonstrated by the GPI M cells is approximately twice that of HaCat cells and of an isolated keratinocyte clone that was not characterized as being mutated in GPI anchor biosynthesis (GPI NM). The conclusion that r150 is a negative modulator of TGF-β responses is confirmed by enhanced phosphorylation of endogenous Smad2 exhibited by the GPI anchor deficient cells as compared to the parental HaCat. This phenomenon is reproducible in both GPI anchor mutants that were cloned (GPI M and GPI M1). In comparison to the HaCat cells. both GPI M and GPI M1 demonstrate a significantly elevated level of Smad2 phosphorylation which is detectable after 20–45 minutes of TGF-β1 treatment and sustained for as long as 180 minutes. Additionally, the GPI M cells demonstrate an enhanced Smad2 phosphorylation in response to different doses of TGF-β1 (2–50 μM) as compared to the parental HaCat cells. Upon treatment with TGF-β2, there is no detectable alteration in the pattern of Smad2 phosphorylation between HaCat and GPI M cells, indicating that the loss of r150 may not impact TGF-β2 responsiveness. This is also seen in the p3TP-Lux luciferase assay, whereby the HaCat and GPI M cells display similar levels of TGF-β2 induced luciferase activity. This is not surprising since r150 has virtually no affinity for TGF-β2 (Tam et al, 1998). The increased intensity and duration of the TGF-β1 induced Smad2 phosphorylation likely contributes to the enhanced transactivation of the PAI-1 promoter in the GPI anchor deficient cells.

r150's interaction with the types I and II receptors is reminiscent of another accessory receptor, endoglin. Endoglin is a 180 kDa homodimeric transmembrane protein that binds TGF-β1 and TGF-β3, and can interact with the types I and II receptor (see section 1.2.2; Cheifetz et al, 1992; Yamashita et al, 1994b). Like the r150, it possesses no kinase domain, but endoglin displays a short cytoplasmic region that is constitutively phosphorylated (Yamashita et al, 1994b). Furthermore, overexpression of endoglin exerts an inhibitory effect on TGF-β mediated growth inhibition, PAI-1 induction and angiogenesis (Letamendia et al, 1998; Li et al, 2000). However, unlike r150, endoglin cannot bind TGF-β in the absence of the type II receptor and hence, its interaction with the signaling receptors is a ligand induced phenomenon. Furthermore, endoglin is predominantly expressed in endothelial cells while our studies indicate that r150 is not found in endothelial cell types (Wong et al, 2000; Tam and Philip, unpublished observations). Therefore, it is possible that the mechanisms by which r150 and endoglin exert their inhibitory effects are distinct from each other.

Figure 11:
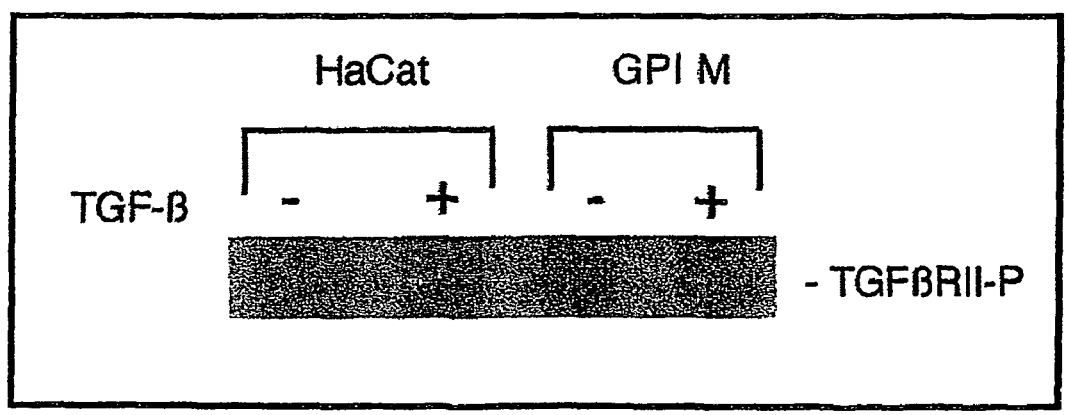
FIG. 11: Autophosphorylation of type II kinase in HaCat and GPI anchor mutated cells. HaCat or GPI M cells were left untreated (−) or treated (+) with 100 pM of TGF-β1 for 20 minutes. Precleared lysates were immunoprecipitated with 3 μg/ml of anti-type II receptor antibody overnight. Following adsorption to protein A sepharose beads, 10 μCi of gamma $^{32}$P was added to the immunocomplexes and incubated for 30 minutes at 30° C. to allow phosphorylation to occur. The reaction was halted by the addition of sample buffer and immunocomplexes were then subjected to SDS-PAGE under reducing conditions. This data is representative of two different experiments.

What are the potential molecular mechanisms by which r150 regulates TGF-β signaling? Through its interaction with the TGF-β signaling receptors, r150 may modulate the serine/threonine kinase activity of the types I or II receptors. The autophosphorylation of key residues in the type II receptor is important in the regulation of kinase function (Luo and Lodish, 1997). In vitro kinase assay with the anti-type II receptor antibody indicates that there is no marked difference in the type II autophosphorylation in GPI anchor deficient cells as compared to that of HaCat cells in the absence or presence of TGF-β1 (FIG. 11). It is possible that r150 may interact with the type I receptor to hamper its phosphorylation by the type II receptor, and hence, activation of the type I kinase. This would be similar to the action of FKBP12, an immunophilin which interacts with the type I kinase and exerts an inhibitory effect on TGF-β mediated cellular responses (Wang et al, 1996). However, our attempts to assess the phosphorylation of the type I kinase by the in vitro kinase assay with the anti-type I receptor antibody using previously described methods were unsuccessful (Wrana et al, 1994; Wieser et al, 1995). Alternatively, r150's interaction with the type II receptor may exert a negative regulatory effect on TGF-β signaling as is seen with TRIP-1, a WD domain protein that specifically associated with the type II receptor and suppresses TGF-β induced transactivation of the PAI-1 promoter (Choy and Derynck, 1998). However, it is presently unclear if r150 interacts with the signaling receptors in the absence of TGF-β, or if the interaction is a strictly a ligand induced phenomenon. In addition, it is unknown if r150 preferentially interacts with the type I or type II receptor.

Our previous work indicates that soluble r150 retains its ability to bind TGF-β1 in absence of the types I and II receptors and of an intact membrane (Tam et al, 2001). Hence, it is likely that r150 binds to TGF-β1 independently from the TGF-β signaling receptors when attached to the cell surface. This is in contrast to the type I receptor kinase and endoglin which only recognize TGF-β bound to the type II receptor (Cheifetz et al, 1992; Wrana et al, 1994; Letamendia, 1998). Therefore, the membrane-anchored form of r150 may regulate TGF-β1 binding to its receptors. This possibility can be interpreted from the results which show that GPI anchor deficient cells display an enhanced Smad2 phosphorylation even at low and intermediate doses of TGF-β1 (2–10 pM) as compared to the parental HaCat. Furthermore, in the p3TP-Lux luciferase assay, a dose response is demonstrated by the mutant cells upon 4 hours of 10 pM (4.9 fold induction) and 100 pM TGF-β1 (8.4 fold induction) treatment. In contrast, the fold increases in HaCat cells are similar at both doses (3.3 and 3.9 respectively). Hence, the access of TGF-β1 to its receptors appears to be ameliorated in the absence of r150. Therefore, unlike the type III receptor whose role is to facilitate binding of TGF-β to its signaling receptors, r150 may not play the role as an "enhance" of TGF-β binding (Lopez-Casillas et al, 1993). As a result, the membrane-anchored r150 may act to sequester TGF-β1, but not TGF-β2 or TGF-β3, away from the signaling receptors on the call surface. Thus, in the absence of r150. Lower amounts of TGF-β1 can induce the heteromerization of the types I and II receptors which can surpass the signaling threshold required to activate the type I kinase, leading to Smad2 phosphorylation.

r150 may potentially have a role in the cellular "compartmentalization" of the types I and II receptors and of the R-Smads. There is an emerging theme in signal transduction biology whereby signaling molecules can be compartmentalized into membrane entities known as caveolae and "lipid rafts." These are organized lipid microdomains which as serve centres in which signaling molecules of various pathways can effectively interact (Sargiacomo et al, 1993; Horejsi et al, 1999). GPI-anchored proteins have been detected in caveolae or lipid rafts in association with other signaling molecules such as Src-like kinases, G-proteins, PKC, and PDGF receptor (Sargiacomo et al, 1993; Lisanti et al, 1994; Oka et al, 1997; Liu et al, 1997). The association of r150, a GPI-anchored protein, with the types I and II receptors suggests that the TGF-β receptors may also be organized in these plasmalemmal entities. This is a possibility since caveolin-1, the main scaffolding protein in caveolae, was recently reported to co-localize with the types I and II receptors and Smad2 in caveolae-enriched membrane fractions. The type I receptor was demonstrated to directly associate with caveolin-1 which resulted in the downregulation of TGF-β mediated transcriptional responses and suppression of ligand induced Smad2 phosphorylation (Razani et al, 2001). Furthermore, the FYVE domain in Smad anchor for receptor activation (SARA), a protein that plays a prominent role in controlling the subcellular localization of Smad2, was required to maintain SARA localized in punctate "spots" near the cell surface as characterized by immunofluorescence microscopy (Tsukazaki et al, 1998). SARA was shown to recruit Smad2 into these domains where TGF-β receptors also co-localized. The identity of these "spots" were not confirmed, but are speculated to be lipid rafts. Presently, it is not known whether SARA interacts with r150. That SARA and r150 may synergistically act to localize r150 into lipid microdomains is an interesting possibility. within caveolae or lipid rafts, the TGF-β signaling machinery may also potentially interact with signaling molecules of other pathways that reside in these structures. This would provide a structural explanation as to how TGF-β can elicit the participation of multiple signaling pathways.

GPI-anchored proteins are implicated in the maintenance of skin homeostasis. Targeted deletion of the GPI anchor biosynthetic gene, PIG-A, in the epidermis of transgenic mice results in smaller pups exhibiting skin with a wrinkled appearance and thickened stratum corneum as compared to wild type mice (Tarutani et al, 1997). This defect in skin development is the apparent cause of death of these mice within 1–3 days after birth. Interestingly, transgenic mice engineered to overexpress TGF-β1 in the epidermis also demonstrate a compact stratum corneum with an increase in the stratified cell layers as compared to wild type mice (Sellheyer et al, 1993). Due to the overexpression of TGF-β1, there is a significant reduction in the number of proliferating epidermal cells as determined by pulse labelling with 5-bromodeoxyuridine. Death of these transgenic mice is also attributed to abnormal skin development. Taken together, the targeted overexpression of TGF-β1 in the epidermis appears to mimic that of the PIG-A deletion. It is possible to envision that the ablation of r150's expression in the epidermis as a consequence of the PIG-A deletion would result in the loss of its inhibitory effects in TGF-β action, thus contributing to the subsequent hyperactivity of TGF-β1 signaling in the skin. Hence, r150 may play an essential role in skin development as a key regulator of TGF-β's function in epidermal differentiation and homeostasis.

In conclusion, studies of TGF-β responses in the GPI anchor deficient keratinocytes have provided critical insight into r150's function in TGF-β signaling. The present results indicate that r150 negatively modulates TGF-β action in human keratinocytes. In r150 deficient keratinocytes, TGF-β induced Smad2 phosphorylation and PAI-1 expression are enhanced. It is conceivable that r150 may directly modulate type I and II kinase activity through its interaction with the signaling receptors. In addition, due to r150's ability to bind TGF-β1 on its own, the membrane bound and soluble r150 may regulate ligand availability by acting as a scavenger receptor. Delineation of r150's structure is necessary to elucidate the precise molecular mechanisms by which this novel accessory receptor regulates TGF-β signaling.

EXAMPLE 3

Sequence of r150 and Nucleic Acids Encoding the Same

Figure 12:
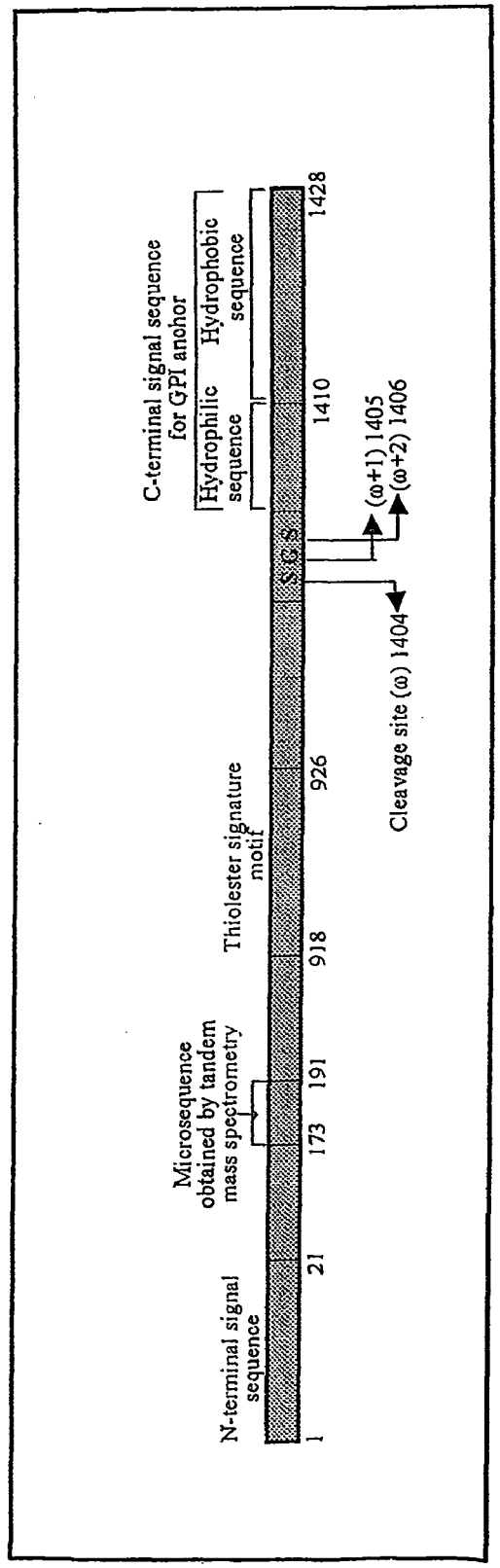
FIG. 12: Schematic diagram representing the cloned sequence of the r150 protein.

Cloning of r150 and expression of r150 gene confirm that r150 is an inhibitor of TGF-responses: To determine its structural identity, r150 was purified on a TGF-1 affinity column and analyzed by tandem mass spectrometry (Harvard Microchemistry Facility, Harvard Univ) which allowed us to obtain a 19 amino acid microsequence. This matched to the 5' end of an express sequence tagged (EST) cDNA clone of unknown function from human placenta. Subsequently, sequencing by PCR using seven primers, the full sequence was obtained. Alignment and conserved domain analysis revealed it to be a novel protein of 1428 amino acids with an N-terminal signal sequence and a C-terminal GPI anchor attachment signal sequence (FIG. 12 and SEQ ID No: 2). The most likely GPI anchor cleavage site (ω) is at amino acid residue 1404. The predicted molecular mass and structural features indicate that this gene product represents r150. This novel TGF-accessory receptor has a thiolester signature motif and belongs to the complement C3/2-macroglobulin superfamily as recently found in Lin et al, (2002). These authors, using a very different strategy (affinity binding of blood cells types with monoclonal antibodies) have identified a protein which has 1445 amino acids, which is very similar to r150. No definite function has been assigned to this protein called CD109, considered by the present inventors to be a variant of r150. Expression studies in HaCaT and 293 cells confirm that the cDNA encodes a 150 kDa GPI-anchored protein.

Figure 13:
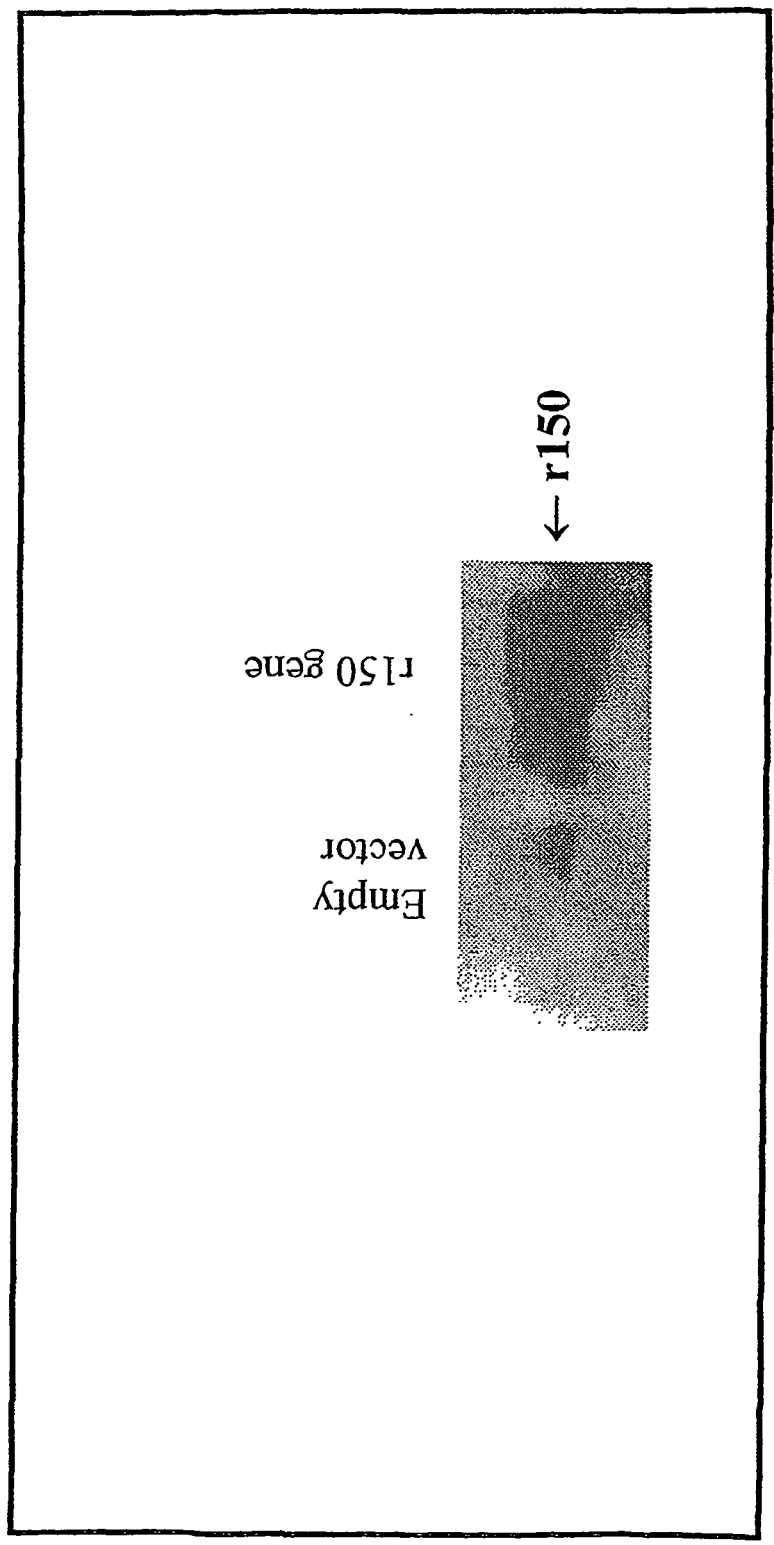
FIG. 13: HaCaT or 293 cells were transfected with r150 gene or the empty vector (pCMV sport 6) and cell lysates were fractionated by SDS-PAGE and transferred onto nitrocellulose membrane and immunoblotted with anti-CRD antibody. The Western blot shown is representative of four experiments (two each with HaCaT and 293 cells).
Figure 14:
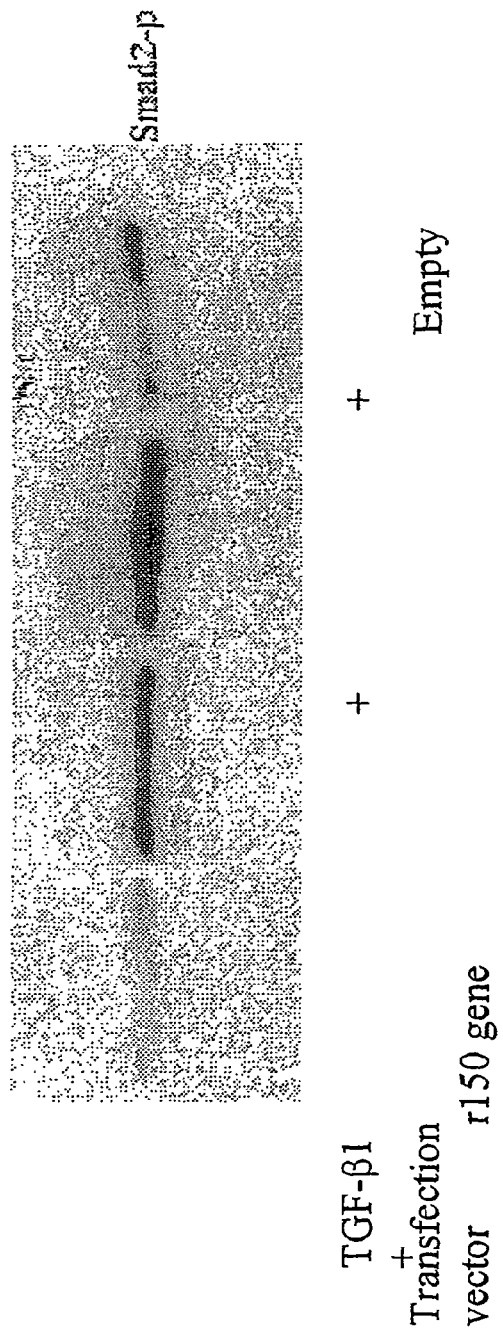
FIG. 14: HaCaT or 293 cells were transfected with r150 gene or the empty vector (pCMV sport 6) or were left untransfected. Cells were allowed to recover for 24 hrs and were treated with 100 pM TGF-1 for 30 minutes. Cell lysates were then Western blotted with an anti-phosphoSmad2 antibody.
Figure 15:
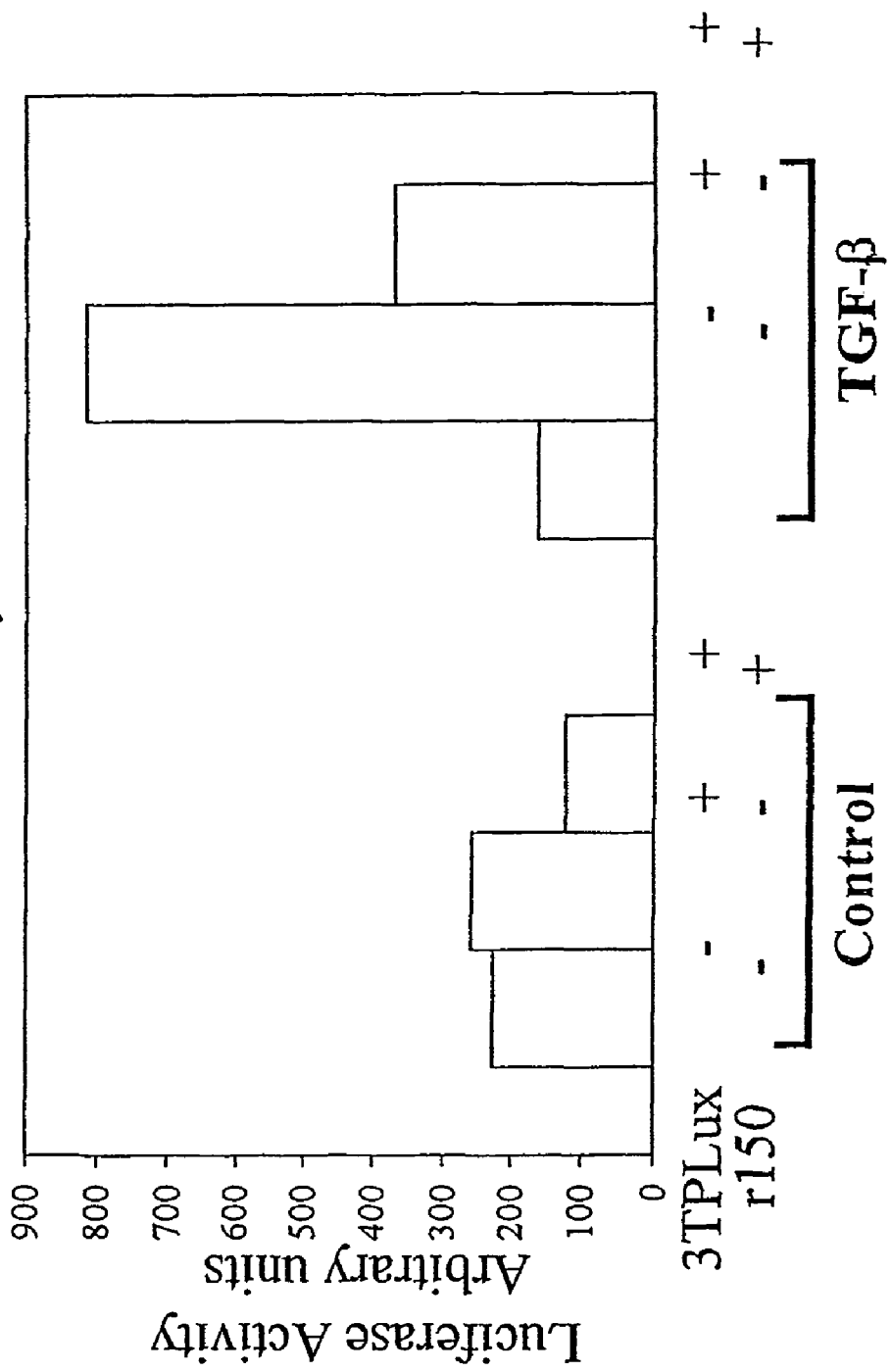
FIG. 15: HaCaT or 293 cells were transfected with r150 gene or the empty vector (pCMV sport 6) or were left untransfected. Cells were allowed to recover for 24 hrs and were treated with 100 pM TGF-1 for 24 hours, or were left untreated. The luciferase activity was normalized to glactosidase activity obtained from a cotransfected CMV gal palsmid.
Figure 16:
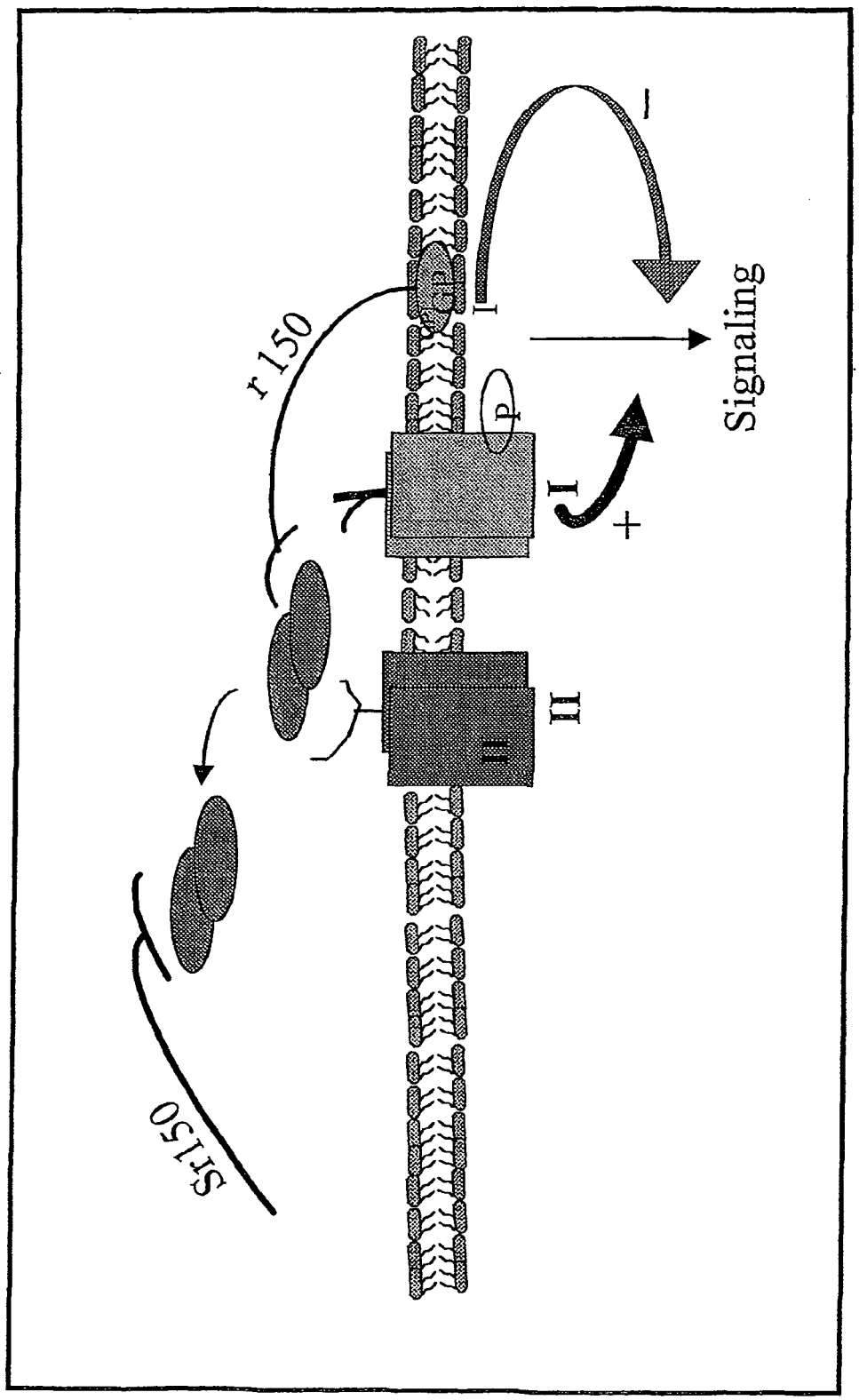
FIG. 16: Schematic model of the mechanism by which r150 inhibits TGF-responses.

Transfection of HaCaT and 293 cells with the r150 gene (SEQ ID NO: 1) and detection of the expressed protein by an antibody specific for GPI anchor (anti-CRD antibody) demonstrate that the expressed protein migrates at 150 kDa and that it contains a GPI anchor as expected of r150 (FIG. 13). Furthermore, overexpression of r150 in HaCaT and 293 cells results in strong negative modulation of TGF-induced Smad 2 phosphorylation and gene promoter activity, providing strong evidence to confirm that r150 is an inhibitor of TGF-signaling and responses. Cells transfected with r150 displayed markedly decreased Smad 2 phosphorylation upon stimulation with TGF- when compared with untransfected cells or cells transfected with the empty vector (FIG. 14). Similarly, transfection of cells with the 3TPLUX promoter-reporter construct (encoding plasminogen activator inhibitor promoter linked to the luciferase reporter gene) resulted in a marked decrease in both the basal and TGF-induced promoter activity (FIG. 15). Taken together, our results demonstrate that r150 is an inhibitor of TGF-signaling and responses in vitro and implicate r150, in its membrane anchored and/or soluble form, as a key regulator TGF-action in vivo (FIG. 16).

Figure 17:
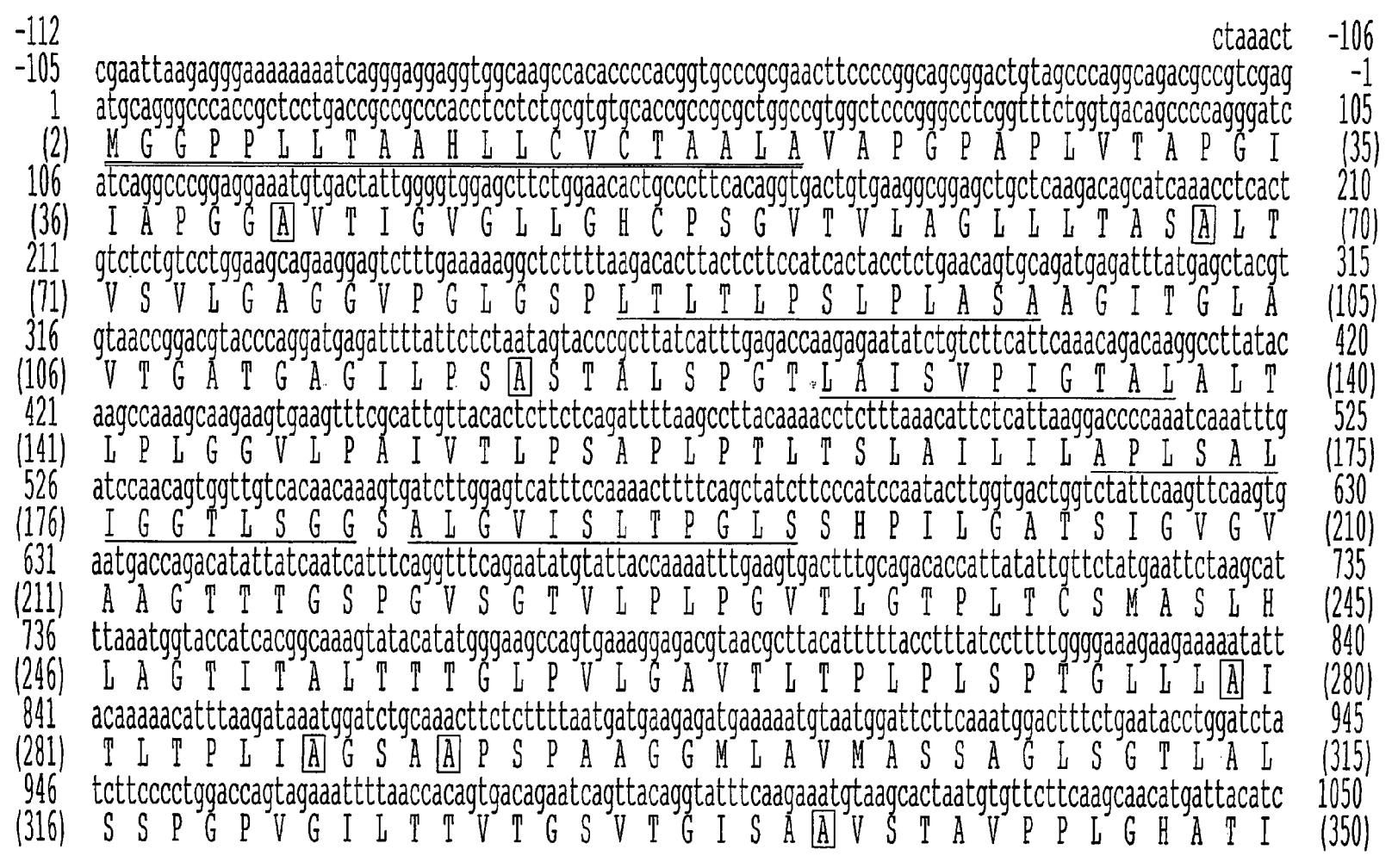
Figure 17:
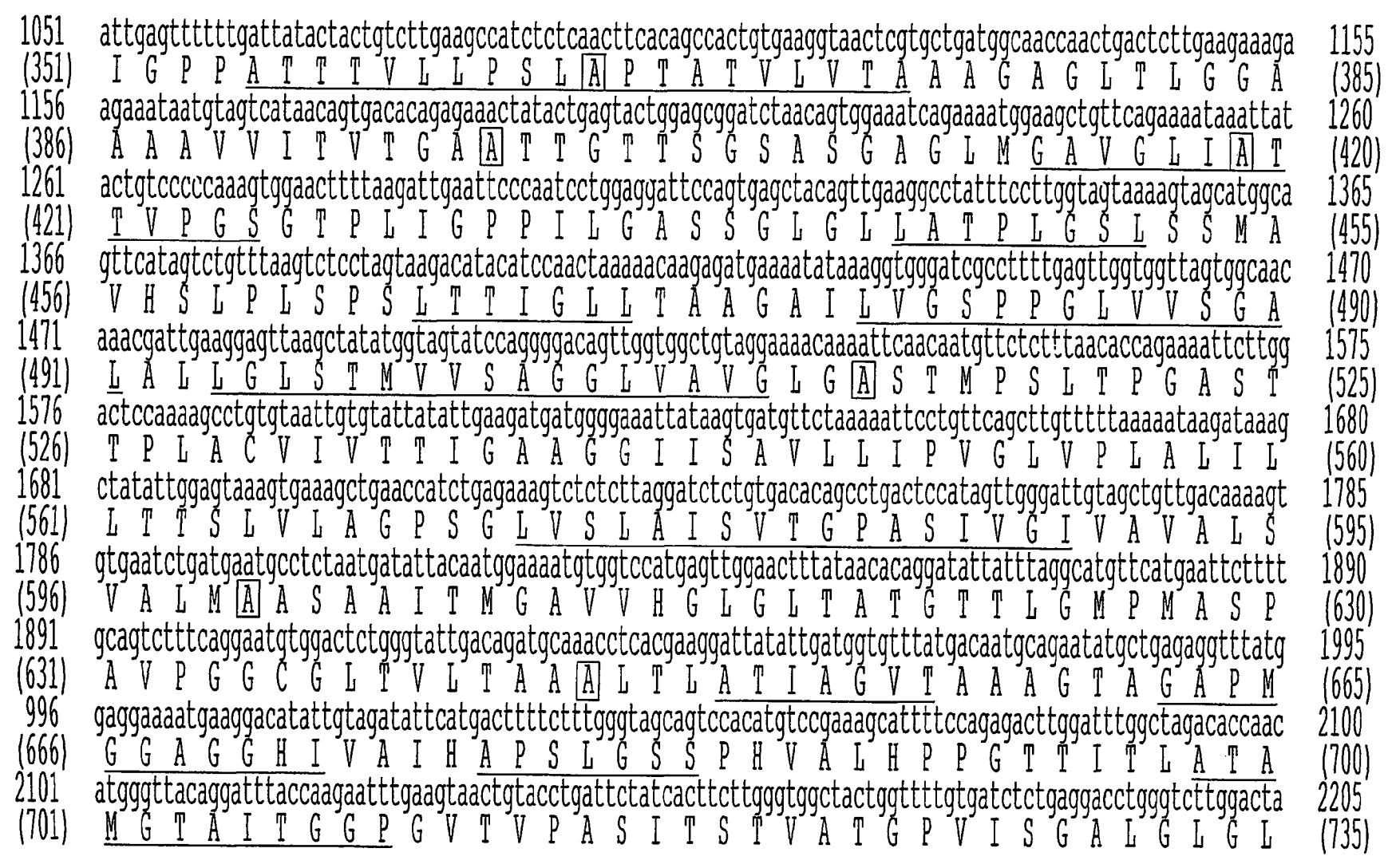

Sequence comparisons with the ones disclosed by Lin et al (2002) and Schuh et al. (2002) provide indications of variants (see FIG. 17). Some amino acid residues may change, but would presumably not change the property of binding TGF-β1. At least two types of r150-like would exist: one with Tyr, one with Ser at position 703. The TGF-β1 binding region can be predicted by sequence comparison with the sequences disclosed for $\alpha_2$ macroglobulin (Webb et al. 1998). The TGF-β1 binding domain is ascribed between amino acids 591 and 774 of $\alpha_2$-M protein sequence. The minimal binding sequence appears to be the 16-mer WDL-WUNSAGVAEVGU (Webb et al. 2000). r150 corresponding sequence shows little homology with this sequence. However, the surrounding sequences are more homologous to r150. Besides that, r150 appears to be much more selective than $\alpha_2$M for TGF-β1. It is therefore possible that the above 16-mer is sort of a "consensus" sequence with allows versatility in the binding of a plurality of cytokins. The corresponding r150 sequence would be much more specific to TGF-β1. This sequence is SEQ ID No: 12 for r150 and its coding nucleic acid is defined in SEQ ID NO: 11. Any protein comprising this particular minimal 16mer is within the scope of this invention.

EXAMPLE 4

Mapping the TGF-β Binding Domain of r150

To confirm that r150 binding domain corresponds to th one found for $\alpha_2$M, the following procedure is performed.

The ligand binding domain of r150 is mapped by producing deletion mutants of r150 and analyzing ligand binding activity. The requirement for the GPI anchor for r150 function is examined using chimeric constructs in which the C-terminal GPI anchor sequence of r150 is replaced with the transmembrane domain (TM) or the GPI anchor sequence of an irrelevant protein, and determining alterations in TGF-β responses. The deletion mutagenesis and creation of chimeric constructs is done as described previously in collaboration with Dr. Uri Saragovi, McGill. (Taheri et al, 2000; Zaccaro et al, 2001)

Deletion mutants are generated using progressive digestion of r150 cDNA using BAL-31 exonuclease starting ~20 amino acids down stream from the signal peptide. Digests are repaired and the fragments are sub-cloned to reattach the signal peptide. The deletion mutants, the full length r150 or the empty vector are expressed in COS-7 cells and in GPI mutant keratinocytes as previously described (Pepin et al, 1994). Cells will then be affinity labeled with 125I-TGF-β1 and analyzed by SDS-PAGE to determine ligand binding activity as described previously (Tam and Philip, 1998). The generation of chimeric constructs (r150 in which its GPI anchor sequence is replaced with the TM of insulin receptor or with the GPI anchor sequence of NCAM), was performed using overlapping PCR as previously described (Screaton et al, 2000; Zaccaro et al, 2001). Wild type r150 and the chimeric constructs are expressed in COS-7 cells and in GPI mutant keratinocytes, and TGF-β responses are determined.

Although the present invention has been described hereinabove by way of preferred embodiments thereof, it can be modified, without departing from the spirit and nature of the subject invention as defined in the appended claims.

REFERENCES

Blobe, G C., Schiemann, W P., Lodish, H. (2000). Role of Transforming growth factor-β in human disease. NEJM. 342: 1358.

Bordier C. 1981. Phase separation of integral membrane proteins in Triton X-114 solution. J Biol Chem 256: 1604–1607.

Boyd F T., and Massague J. (1989). Transforming growth factor-β inhibition of epithelial cell proliferation linked to the expression of a 53 kDa Membrane receptor. J. Biol. Chem. 264: 2272–2278.

Broomfield S J, Hooper N M. 1993. Characterization of an antibody to the cross-reacting determinant of the GPI-anchor of human membrane dipeptidase. Biochim Biophys Acta 1145: 212–218.

Brown D. 1993. The tyrosine kinase connection: how GPI-anchored proteins activate T cells. Curr Opinion Immunol 5: 349–354.

Brown D A, London E. 1998. Functions of lipid rafts in biological membranes. Ann Rev Cell Develop Biol 14: 111–136.

Chajek-Shaul T. Halimi O, Ben-Naim M. Stein O, Stein Y. 1989. Phosphatidylinositol-specific phospholipase releases lipoprotein lipase from the heparin releasable pool in rat heart cell cultures. Biochim. Biophys Acta 1014: 178–183.

Cheifetz S. and Massague J. (1991). Isoform specific transforming growth factor-β binding proteins with membrane attachments sensitive to phosphatidyl-specific phospholipase C. J. Biol. Chem. 266: 20767–20772.

Cheifetz S., Bellon T., Cales C., Vera S., Bernabeau C., Massague J., and Letarte M. (1992). Endoglin is a component of the TGF-β receptor system in human endothelial cells. J. Biol. Chem. 267: 19027–19030.

Chen R., Walter E I., Parker G., Lapurga J P., Millan J L., Ikehara Y., Udenfriend S., and Medof M E. (1998). Mammalian glycosylphosphatidylinositol anchor transfer to proteins and post-transfer deacylation. Proc. Natl. Acad. Sci. USA 95: 9512–9517.

Choi M E. 1999. Cloning and characterization of a naturally occurring soluble form of TGF-β type I receptor. Am J Physio 276: F88–F95.

Choy L., and Derynck R. (1998). The type II TGF-β receptor-interacting protein TRIP-1 acts as a modulator of the TGF-β response. J. Biol. Chem. 273: 31455–31462.

Clark R A F. 1996. Wound Repair: overview and general considerations. In: Clark R A F, editor. The Molecular and Cellular Biology of Wound Repair. New York: Plenum Press, pp.3–35.

Dumont N, O'Connor-McCourt M D, Philip A. 1995. Transforming growth factor-β on human endometrial cells: identification of the type I, II and III receptors, and glycosyl-phosphatidyl inositol anchored TGF-β binding proteins. Mol Cell Endocrinol 111: 57–66.

Germain L. Rouabhia M, Guignard R. Carrier L, Bouvard V, Auger F A. 1993. Improvement of human keratinocyte isolation and culture using thermolysin. Burns 19: 99–104.

Glick A B, Kulkarni A, Tannenbaum T. Hennings H, Flanders K C, O'Reilly M, Sporn. M B, Karlsson S, Yuspa S H. 1993. Loss of expression of TGF-β in skin and skin tumors is associated with hyper proliferation and high risk of malignant conversion. Proc Natl Acad Sci USA 90: 6076–6080.

Glick, A B, Lee, M M, Darwiche, N, Kulkarni, A B, Karlsson, S, Yuspa, S H. 1994. Targeted deletion of TGF-β1 gene causes rapid progression to squamous cell carcinoma. Genes and Dev 8: 2429–2440.

Gougos A, Letarte M. 1990. Primary structure of endoglin, an RGD-containing glycoprotein of human endothelial cells. J Biol Chem 265: 8361–8364.

Grainger D J, Metcalfe J C. 1996. A pivotal role for TGF-beta in atherogenesis. Biol Rev 70: 571–596.

Hebda P A. 1988. Stimulatory effects of TGF-β and EGF on epidermal cell outgrowth and porcine skin explant cultures. J. Invest, Dermatol. 91: 440–445.

Heldin C H, Miyazono K, ten Dijke P. 1997. TGF-β signaling from cell membrane to nucleus through SMAD proteins. Nature 390: 465–471.

Hooper N M. 1992. Identification of glycosyl-phosphatidylinositol anchor on membrane proteins. In Hooper N M and Turner A J, editors. Lipid Modification of Proteins: A Practical Approach. New York: IRL Press. pp. 89–115.

Hooper N M. 1999. Detergent-insoluble glycosphingolipid/cholesterol-rich membrane domains, lipid rafts and caveolae. Mol Memb Biol 16: 145–156.

Kingsley D M (1994). The TGF-β superfamily: new members, new receptors, and new genetic tests of function in different organisms. Genes & Devel. 8:133–146.

Laiho M., Weis F M B., and Massague J. (1990). Concomitant loss of TGF-β receptor types I and II in TGF-β resistant cell mutants lmplicates both receptor types in signal transduction. J. Biol. Chem. 265: 18518–18524.

Lefer A M, Ma X-L, Weyrich A S, Scalia, R. (1993). Mechanism of the cardioprotective effect of TGF-beta 1 in feline myocardial ischemia and reperfusion. Proc Natl Acad Sci USA 90: 1018–1022.

Letamendia A. Lastres P. Botella L M, Raab U. Langa C. Velasco B, Attisano L. And Bernabeu C. (1998). Role of Endoglin in cellular responses to TGF-β. J. Biol. Chem. 273: 33011–33019.

Letterio J J, Roberts A B. 1998. Regulation of immune responses by TGF-β. Ann Rev Immuno 16: 137–161.

Li C., Hampson I N., Hampson L., Kumar P., Bernabeu C., and Kumar S. (2000). CD10[5] antagonizes the inhibitory signaling of TGF-β1 on human vascular endothelial cells. FASEB J. 14: 55–64.

Li Chengang, Hampson I N, Hampson L, Kumar P, Bernabeu C, Kumar S. 2000. CD105 antagonizes the inhibitory signaling of transforming gowth factor-β1 on human vascular endothelial cells. FASEB J. 14: 55–64.

Lisanti M P, Sargiacomo M, Graeve L, Saltiel A R, Rodriguez-Boulan E. 1988. Polarized apical distribution of glycosyl phosphatidylinositol-anchored proteins in renal epithelial cell lines. Proc Natl Acad Sci USA 85: 9557–9561.

Lisanti M P., Scherer P E., Vidugiriene J., Tang Z L., Hermanowski-Vosatka A., Tu Y H., Cook R F., and Sargiacomo M. (1994). Characterization of caveolin-rich membrane domains isolated from an endothelial rich source-implications for human disease. J. Cell. Biol. 126:111–126.

Liu J., Oh P., Horner T., Rogers R A., and Schnizler J E. (1997). Organized endothelial cell surface signal transduction distinct from GPI-anchored protein microdomains. J. Biol. Chem 272: 7211–7222

Lopez-Casillas F, Payne H M, Andres J L, Massague J 1994. Betaglycan can act as a dual modulator of TGF-β access to signaling receptors: mapping of ligand binding and GAG attachment sites. J Cell Biol 124: 557–568.

Lopez-Casillas F, Wrana J L, Massague J 1993. Betaglycan presents ligand to the TGF-β signaling receptor. Cell 73: 1435–1444.

lopez-Casillas, F., Wrana, J. L. and Massague, J. (1993). Betaglycan presents ligand to the TGF-β signaling receptor. Cell 73; 1435–1444.

Low M G. (1989). Glycasylphosphatidylinostiol: a versatile anchor for cell surface proteins. FASEB J. 3: 1600–1608.

Luo K., and Lodish H F. (1997). Positive and negative regulation of type II TGF-β receptor signal transduction by autophosphorylation on mutiple serine residues EMBO J. 8: 1970–1997.

Massague J. (1998). TGF-β signal transduction. Annu. Rev. Biochem. 67:753–791.

McNeil H. Williams C, Guan J. Dargunow M, Lawlor P, Sirimanne E, Nikolics K, Gluckman P. 1994. Neuronal escue with trnsforming growth factor-beta 1 after hypoxic-ischaemic brain injury. Neuroreport 5: 901–904.

Mehta, J L. Yang B C, Strates, B S, Mehta P. 1999. Role of TGF-beta 1 in platelet-mediated cardioprotection during ischemia-reperfusion in isolated rat hearts. Growth Factors 16; 179–190.

Metz C N, Brunner G, Choi-Muira N H, Nguyen H. Gabrilove J, Caras I W, Altszuler N. Rifkin D B, Wilson E L, Davitz M A. 1994. Release of GPI-anchorecd membrane proteins by a cell-associated GPI-specific phospholipase D. EMBO 13: 1741–1751.

Moulin V, Auger F A, O'Connor-McCourt M, Germain L. 1997. Fetal and postnatal sera differentially modulate human dermal fibroblast phenotypic and functional features in vitro. J Cellul Physio 171:1–10.

Movahedi S. Hooper N M. 1997. Insulin stimulates the release of the GPI-anchored membrane dipeptidase from 3T3-L1 adipocytes through the action of a phospholipase C. Biochem J 326: 531–537.

Nosjean O., Briolay, A. and Roux, B. (1997). Mammalian GPI proteins: sorting, membrane residence and functions. Biochim. BioPhys. Acta. 1331: 153–186.

Nunes I, Kojima S, Rifkin D B. 1996. Effects of endogenously activated TGF-β on growth and differentiation of retinoic acid treated HL-60 cells. Cancer Res 56: 495–499.

O'Kane S. Ferguson M W J. 1997. Transforming growth factor-βs and wound healing. Int J Biochem Cell 29: 63–78.

Oka N., Yamamoto M., Schwencke C., Kawabe J., Ebina T., Ohno S. and Couet J., Lisanti, M P., and Ishikawa, Y. (1997). Caveolin interaction with protein kinase C. J. Biol. Chem. 272: 33416–33421.

Onichtchouk D, Chen Y-G, Dosch R. Gawantka V, Dellus H. Massague J. Niehrs C. 1999. Silencing of TGF-β signaling by the psuedoreceptor BAMBI. Nature 401: 480–484.

Pasch M C., Okada N., Bos J D., and Asghar S S. (1998). Effects of UVB on the synthesis of complement proteins by keratinocytes. J. Invest.Dermatol. 111: 683–688.

Patel B N, David S. 1997. A Novel Glycosyl phosphatidylinositol-anchored form of ceruloplasmin is expressed by mammalian astrocytes. J Biol Chem 272: 20185–20190.

Peltonen J, Hsaio L L, Jaakkola S, Solberg S. Aumailley M, Timpl R, Chu M L. Uitto J. 1991. Activation of collagen gene expression in keloids: co-localization of type I and type IV collagen and TGF-β1 mRNA. J Invest Dermatol 97: 240–248.

Philip A, Hannah R. O'Connor-McCourt M. 1999. Ectodomain cleavage and shedding of the type III transforming growth factor-β receptor in lung membranes. Eur J Biochem 261: 618–628.

Philip A, O'Connor-McCourt M D. 1991. Interaction of TGF-β with alpha 3-macroglobulin: role in transforming growth factor-β clearance. J Biol Chem 266: 22290–22296.

Pietenpol J A, Holt J T, Stein R W, Moses H L. 1990. TGF-β1 suppression of c-myc gene transcription: role in inhibition of keratinocyte proliferation. Proc Natl Acad Sci USA 87: 3758–3762.

Razani B., Zhang X L., Bitzer M., van Gersdorff G., Bottinger E P., and Lisanti M P, (2001). Caveolin-1 regulates TGF-β/SMAD signaling through an interaction with the TGF-β type I receptor. J. Biol. Chem. J. Biol. Chem. 276: 6727–6738.

Roberts A B, Sporn M B. 1990. The transforming growth factor-βs. In Sporn M B and Roberts A B, editors. Peptide Growth Factors and their Receptors I. New York: Springer-Verlag. pp. 419–472.

Rodriguez-Boulan, E., Powell. S K. (1992). Polarity of epithelial and neuronal cells. Ann. Rev. Cell Biol. 8: 395–427.

Rosen C L, Lisanti M P, Salzer J L. 1992. Expression of unique sets of GPI-linked proteins by different primary neurons in vitro. J Cell Biol 117: 617–627.

Saltiel A R. 1996. Diverse signaling pathways in the cellular action of insulin. Am J Physio 270: E375–E382.

Sargiacomo M., Sudol M., Tang Z., and Lisanti M. (1993). Signal transducing molecules and GPI-linked proteins form Caveolin-rich insoluble complex in MDCK cells. (1993). J. Cell Biol. 122: 789–807.

Satiel, A R. Diverse signalling pathways in the cellular actions of insulin. Am.J.Physiol. 270: E375–E385.

Screaton R A., DeMarte L., Draber P., and Stanners C P. (2000). The specificity for the differentiation blocking activity of carcinoembryonic antigen resides in its GPI anchor. J. Cell. Biol. 150: 613–625.

Sega G A. (1984). A review of the genetic effects of ethyl methanesulfonate. Mut. Res. 134: 113–142.

Sellheyer K., Bickenbach J R., Rothnagel J A., Bundman D., Longley M., Greig T., Roberts A B., and Roop D R. (1993). Inhibition of skin development by overexpression of TGF-β1 in the epidermis of transgenic mice. Proc. Natl. Acad. Sci. USA. 90: 5237–5241.

Shukla S D. (1982). Phosphatidylinostol specific phospholipase C. Life Sci. 30: 1323–1355.

Stevens V L. (1999). Selection of mammalian cell mutants in GPI biosynthesis. In: Gelb M H (Ed.). Protein Lipidation Protocols. Totowa: Humana Press. pp. 13–22.

Stevens V L., Zhang H., and Harreman M. (1998). Isolation and characterization of a Chinese hamster ovary (CHO) mutant defective in the second step of glycosylphosphatidylinositol biosynthesis. Biochem. J. 313: 253–258.

Tam B Y Y, Germain L, Philip A. 1998. TGF-β receptor expression on human keratinocytes: a 150 kDa GPI-anchored TGF-β binding protein forms a heteromeric complex with the types I and II receptors. J Cell Biochem 70: 573–586.

Tam B Y Y, Philip A. 1998. Transforming growth factor-β receptor expression on human skin fibroblasts: dimeric complex formation of type I and type II receptors and identification of glycosyl phosphatidylinositol-anchored TGF-β binding proteins. J Cell Physio 176: 553–564.

Tam B Y Y., Germain L., Hooper N M., and Philip A. Characterization of a 150 kDa accessory receptor to TGF-β on keratinocytes: direct evidence for a GPI-anchor and ligand binding of the released form. J. Cell. Biochem. In press.

Tarutani M, Itami S. Okabe M, Ikawa M, Tezuka T. Yoshikawa K, Kinoshita T. Takeda J. 1997. Tissue-specific knockout of the mouse Pig-a gene reveals important roles for GPI-anchored proteins in skin development. Proc Natl Acad Sci USA 94: 7400–7405.

Tarutani, M., Itami, S., Okabe, M., Ikawa, M., Tezuka, T., Yoshikawa K., Kinoshita, T., Takeda, J. (1997). Tissue specific knockout of the mouse Pig-a gene revels important roles for GPI-anchored proteins in skin development. Pro. Natl. acad. Sci. USA. 94: 2386–2391.

Tsukazaki T., Chiang T A., Davison A F., Attisano L., and Wrana J L. (1998). SARA, a FYVE domain protein recruits Smad2 to the TGF-β receptor. Cell 95: 779–791.

Turner A J (1994). PIG-tailed membrane proteins. Essays in Biochem. 28: 113–127.

Venneker G T., Das P K., Das P K., Melnardi M M H M., Marle J., Veen H A., Bos J D., and Asghar S S. (1994). GPI-anchored membrane proteins are constitutively down-regulated in psoriatic skin. J. Pathol. 172: 189–197.

Venneker, G T., Das, P K., Meinardi, M M., von Marle, J., van Veen, H A., Bos, J D., Asghar, S S. (1994). Glycosylphosphatidylinositol (GPI)-anchored membrane proteins are constitutively down-regulated in psoriatic skin. J. Path. 172: 189–197.

Wang X J, Greenlaugh D A. Bikenbach J R, Jiang A, Bundman D S, Kreig T, Oerynck R, Roop D R. 1997. Expression of a dominant-negative type II TGF-β receptor in the epidermis of transgenic mice blocks TGF-β-mediated growth inhibition. Proc Natl Acad Sci USA. 94: 2386–2391.

Wang Y., Li B Y., Danielson P D., Shah P C., Rockwell S., Lechlelder R J., Martin J., Manganaro T., and Donahue P K. (1996). The immunophilin FKBP12 functions as a common inhibitor of the TGF-β family type I receptors. Cell 86: 435–444.

Wieser R., Wrana J L., and Massague J. (1995). GS domain mutations that constitutively activate TβR-I, the downstream signaling component in the TGF-β receptor complex. EMBO J. 14: 2199–2208.

Wong S H., Hamel L., Chevalier S., and Philip A. (2000). Endoglin expression on human microvascular endothelial cells: association with betaglycan and fomation of higher order complexes with TGF-β signaling receptors. Eur. J. Biochem. 267: 5550–5560.

Wrana J L, Attisano L, Wieser R, Venturs F and Massague J. (1994). Mechanism of activation of the TGF-β receptor. Nature 370, 341–347.

Wrana, J. L., Attisano, L., Wieser, R., Ventura, F. and Massague, J. (1994). Mechanism of activation of the TGF-β receptor. Nature 370: 341–347.

Xie M, Sesko A M, Low M. 1993. Glycosyl phosphatidylinositol-specific phospholipase D. Am J Physiol 265: C1156–C1166

Yamamoto T. Noble N A, Miller D E, Border W A. 1994. Sustained expressed of TGF-β1 underlies development of progressive kidney fibrosis. Kidney Int 45: 916–927.

Yamashita H., Ichijo H., Grimsby S., Moren A, tan Dijke P., and Miyazono K. (1994b). Endoglin forms a heteromeric complex with the signaling receptors for TGF-β. J. Biol. Chem. 269: 1995–2001.

Zambruno G. Marchisio P C, Marconi A, Vaschieri C, Mechiori A, Giannett A, DeLuca M. 1995. TGF-β1 modulates β1 and β5 integrin receptors and induces the de novo expression of the alphaVβ6 heterodimer in normal human keratinocytes for wound healing. J Cell Biol 129: 853–865.

Zamze S E, Ferguson M A J, Collins R. Dwek R A, Rademacher T W. 1988. Characterization of the cross-reacting determinant (CRD) of the glycosylphosphatidyl membrane anchor of Trypanosoma brucei variant surface glycoprotein. Eur J Biochem 176: 527–534.

Pepin M-C. et al (1994). Mapping of the ligand binding domain of the transforming growth factor-β receptor type III by deletion mutagenesis. Proc. Natl. Acd. Sci. 91: 6997–7001.

Zaccaro, M. C. et al (2001). P75 coreceptors regulate ligand dependent and ligand independent TrK receptor activation, in part by altering Trk docking subdomains. J. Biol. Chem. 276: 31023–31029.

Taheri, M. et al (2000). Self recognition in the Ig superfamily. Identification of precise subdomains in carcinoembryonic antigen required for intracellular adhesion. J. Biol Chem. 275: 26935–26943.

Screaton, R. A. et al (2000). Specificity for the differentiation blocking activity of carcinoembryonic antigen resides in its glycosylphosphatidyl-inositol anchor. J. cell. Biol. 150: 613–625.

SEQUENCE LISTING

```
<160> NUMBER OF SEQ ID NOS: 12

<210> SEQ ID NO 1
<211> LENGTH: 4369
<212> TYPE: DNA
<213> ORGANISM: Homo sapiens
<220> FEATURE:
<221> NAME/KEY: misc_feature
<222> LOCATION: (2133)..(2133)
<223> OTHER INFORMATION: N = A or C

<400> SEQUENCE: 1
tgtagcccag gcagacgccg tcgagatgca gggcccaccg ctcctgaccg ccgcccacct      60
cctctgcgtg tgcaccgccg cgctggccgt ggctcccggg cctcggtttc tggtgacagc     120
cccagggatc atcaggcccg gaggaaatgt gactattggg gtggagcttc tggaacactg     180 ccctttcacag gtgactgtga aggcggagct gctcaagaca gcatcaaacc tcactgtctc    240
tgtcctggaa gcagaaggag tctttgaaaa aggctctttt aagacactta ctcttccatc     300
actacctctg aacagtgcag atgagattta tgagctacgt gtaaccggac gtacccagga     360
tgagatttta ttctctaata gtacccgctt atcatttgag accaagagaa tatctgtctt     420
cattcaaaca gacaaggcct tatacaagcc aaagcaagaa gtgaagtttc gcattgttac     480
actcttctca gattttaagc cttacaaaac ctctttaaac attctcatta aggaccccaa     540
atcaaatttg atccaacagt ggttgtcaca acaaagtgat cttggagtca tttccaaaac     600
ttttcagcta tcttcccatc caatacttgg tgactggtct attcaagttc aagtgaatga     660
ccagacatac tatcaatcat ttcaggtttc agaatatgta ttaccaaaat ttgaagtgac     720
tttgcagaca ccattatatt gttctatgaa ttctaagcat ttaaatggta ccatcacggc     780
aaagtataca tatgggaagc cagtgaaagg agacgtaacg cttacatttt tacctttatc     840
cttttgggga aagaagaaaa atattacaaa acatttaag ataaatggat ctgcaaactt     900
ctcttttaat gatgaagaga tgaaaaatgt aatggattct tcaaatggac tttctgaata    960
cctggatcta tcttcccctg gaccagtaga aatttaacc acagtgacag aatcagttac     1020
aggtatttca agaaatgtaa gcactaatgt gttcttcaag caacatgatt acatcattga    1080
gttttttgat tatactactg tcttgaagcc atctctcaac ttcacagcca ctgtgaaggt    1140
aactcgtgct gatggcaacc aactgactct tgaagaaaga gaaataatg tagtcataac    1200 agtgacacag agaaactata ctgagtactg gagcggatct aacagtggaa atcagaaaat    1260
ggaagctgtt cagaaaataa attatactgt cccccaaagt ggaactttta agattgaatt    1320
cccaatcctg gaggattcca gtgagctaca gttgaaggcc tatttccttg gtagtaaaag    1380
tagcatggca gttcatagtc tgtttaagtc tcctagtaag acatacatcc aactaaaaac    1440
aagagatgaa aatataaagg tgggatcgcc ttttgagttg gtggttagtg gcaacaaacg    1500
attgaaggag ttaagctata tggtagtatc caggggacag ttggtggctg taggaaaaca    1560
```

-continued

```
aaattcaaca atgttctctt taacaccaga aaattcttgg actccaaaag cctgtgtaat     1620
tgtgtattat attgaagatg atggggaaat tataagtgat gttctaaaaa ttcctgttca     1680
gcttgttttt aaaaataaga taaagctata ttggagtaaa gtgaaagctg aaccatctga     1740
gaaagtctct cttaggatct ctgtgacaca gcctgactcc atagttggga ttgtagctgt     1800
tgacaaaagt gtgaatctga tgaatgcctc taatgatatt acaatggaaa atgtggtcca     1860
tgagttggaa ctttataaca caggatatta tttaggcatg ttcatgaatt cttttgcagt     1920
ctttcaggaa tgtggactct gggtattgac agatgcaaac ctcacgaagg attatattga     1980
tggtgtttat gacaatgcag aatatgctga gaggtttatg gaggaaaatg aaggacatat     2040
tgtagatatt catgactttt ctttgggtag cagtccacat gtccgaaagc attttccaga     2100
gacttggatt tggctagaca ccaacatggg ttncaggatt taccaagaat ttgaagtaac     2160
tgtacctgat tctatcactt cttgggtggc tactggtttt gtgatctctg aggacctggg     2220
tcttggacta caactactc cagtggagct ccaagccttc caaccatttt tcatttttt      2280
gaatcttccc tactctgtta tcagaggtga agaatttgct ttggaaataa ctatattcaa     2340
ttatttgaaa gatgccactg aggttaaggt aatcattgag aaaagtgaca aatttgatat     2400
tctaatgact tcaaatgaaa taaatgccac aggccaccag cagacccttc tggttcccag     2460
tgaggatggg gcaactgttc ttttttcccat caggccaaca catctgggag aaattcctat    2520
cacagtcaca gctcttcac ccactgcttc tgatgctgtc acccagatga ttttagtaaa      2580
ggctgaagga atagaaaaat catattcaca atccatctta ttagacttga ctgacaatag     2640
gctacagagt accctgaaaa ctttgagttt ctcatttcct cctaatacag tgactggcag     2700
tgaaagagtt cagatcactg caattggaga tgttcttggt ccttccatca atggcttagc     2760
ctcattgatt cggatgcctt atgctgtgg tgaacagaac atgataaatt ttgctccaaa      2820
tatttacatt ttggattatc tgactaaaaa gaaacaactg acagataatt tgaaagaaaa     2880
agctctttca tttatgaggc aaggttacca gagagaactt ctctatcaga gggaagatgg     2940
ctctttcagt gcttttggga attatgaccc ttctgggagc acttggttgt cagcttttgt     3000
tttaagatgt ttccttgaag ccgatcctta catagatatt gatcagaatg tgttacacag     3060
aacatacact tggcttaaag gacatcagaa atccaacggt gaattttggg atccaggaag     3120
agtgattcat agtgagcttc aaggtggcaa taaaagtcca gtaacactta cagcctatat     3180
tgtaacttct ctcctgggat atagaaagta tcagcctaac attgatgtgc aagagtctat     3240
ccatttttg gagtctgaat tcagtagagg aatttcagac aattatactc tagcccttat     3300
aacttatgca ttgtcatcag tggggagtcc taaagcgaag gaagctttga atatgctgac     3360
ttggagagca gaacaagaag gtggcatgca attctgggtg tcatcagagt ccaaactttc     3420
tgactcctgg cagccacgct ccctggatat tgaagttgca gcctatgcac tgctctcaca     3480
cttcttacaa tttcagactt ctgagggaat cccaattatg aggtggctaa gcaggcaaag     3540
aaatagcttg ggtggttttg catctactca ggataccact gtggctttaa aggctctgtc     3600
tgaatttgca gccctaatga atacagaaag gacaaatatc caagtgaccg tgacggggcc     3660
tagctcacca gtcctcttg ctgtggtaca gccaacggca gttaatattt ccgcaaatgg      3720
ttttggattt gctatttgtc agctcaatgt tgtatataat gtgaaggctt ctgggtcttc     3780
tagaagacga agatctatcc aaaatcaaga agcctttgat ttagatgttg ctgtaaaaga     3840
aaataaagat gatctcaatc atgtggattt gaatgtgtgt acaagctttt cgggcccggg     3900
taggagtggc atggctctta tggaagttaa cctattaagt ggctttatgg tgccttcaga     3960
```

-continued

```
agcaatttct ctgagcgaga cagtgaagaa agtggaatat gatcatggaa aactcaacct    4020
ctatttagat tctgtaaatg aaacccagtt ttgtgttaat attcctgctg tgagaaactt    4080
taaagtttca aatacccaag atgcttcagt gtccatagtg gattactatg agccaaggag    4140
acaggcggtg agaagttaca actctgaagt gaagctgtcc tcctgtgacc tttgcagtga    4200
tgtccagggc tgccgtcctt gtgaggatgg agcttcaggc tcccatcatc actcttcagt    4260 cattttatt ttctgtttca agcttctgta ctttatgaa ctttggctgt gatttatttt      4320
taaaggactc tgtgtaacac taacatttcc agtagtcaca tgtgattgt                4369
```

```
<210> SEQ ID NO 2
<211> LENGTH: 1428
<212> TYPE: PRT
<213> ORGANISM: homo sapiens
<220> FEATURE:
<221> NAME/KEY: MISC_FEATURE
<222> LOCATION: (703)..(703)
<223> OTHER INFORMATION: Xaa = Ser or Tyr

<400> SEQUENCE: 2
```

| Met | Gln | Gly | Pro | Pro | Leu | Leu | Thr | Ala | Ala | His | Leu | Leu | Cys | Val | Cys |
|---|---|---|---|---|---|---|---|---|---|---|---|---|---|---|---|
| 1 | | | | 5 | | | | | 10 | | | | | 15 | |

Thr Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
    50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Lys Asn Ile Thr Lys Thr Phe Lys Ile Asn Gly

```
                275                 280                 285
Ser Ala Asn Phe Ser Phe Asn Asp Glu Glu Met Lys Asn Val Met Asp
    290                 295                 300
Ser Ser Asn Gly Leu Ser Glu Tyr Leu Asp Leu Ser Ser Pro Gly Pro
305                 310                 315                 320
Val Glu Ile Leu Thr Thr Val Thr Glu Ser Val Thr Gly Ile Ser Arg
                325                 330                 335
Asn Val Ser Thr Asn Val Phe Phe Lys Gln His Asp Tyr Ile Ile Glu
            340                 345                 350
Phe Phe Asp Tyr Thr Thr Val Leu Lys Pro Ser Leu Asn Phe Thr Ala
        355                 360                 365
Thr Val Lys Val Thr Arg Ala Asp Gly Asn Gln Leu Thr Leu Glu Glu
    370                 375                 380
Arg Arg Asn Asn Val Val Ile Thr Val Thr Gln Arg Asn Tyr Thr Glu
385                 390                 395                 400
Tyr Trp Ser Gly Ser Asn Ser Gly Asn Gln Lys Met Glu Ala Val Gln
                405                 410                 415
Lys Ile Asn Tyr Thr Val Pro Gln Ser Gly Thr Phe Lys Ile Glu Phe
            420                 425                 430
Pro Ile Leu Glu Asp Ser Ser Glu Leu Gln Leu Lys Ala Tyr Phe Leu
        435                 440                 445
Gly Ser Lys Ser Ser Met Ala Val His Ser Leu Phe Lys Ser Pro Ser
    450                 455                 460
Lys Thr Tyr Ile Gln Leu Lys Thr Arg Asp Glu Asn Ile Lys Val Gly
465                 470                 475                 480
Ser Pro Phe Glu Leu Val Val Ser Gly Asn Lys Arg Leu Lys Glu Leu
                485                 490                 495
Ser Tyr Met Val Val Ser Arg Gly Gln Leu Val Ala Val Gly Lys Gln
            500                 505                 510
Asn Ser Thr Met Phe Ser Leu Thr Pro Glu Asn Ser Trp Thr Pro Lys
        515                 520                 525
Ala Cys Val Ile Val Tyr Tyr Ile Glu Asp Asp Gly Glu Ile Ile Ser
    530                 535                 540
Asp Val Leu Lys Ile Pro Val Gln Leu Val Phe Lys Asn Lys Ile Lys
545                 550                 555                 560
Leu Tyr Trp Ser Lys Val Lys Ala Glu Pro Ser Glu Lys Val Ser Leu
                565                 570                 575
Arg Ile Ser Val Thr Gln Pro Asp Ser Ile Val Gly Ile Val Ala Val
            580                 585                 590
Asp Lys Ser Val Asn Leu Met Asn Ala Ser Asn Asp Ile Thr Met Glu
        595                 600                 605
Asn Val Val His Glu Leu Glu Leu Tyr Asn Thr Gly Tyr Tyr Leu Gly
    610                 615                 620
Met Phe Met Asn Ser Phe Ala Val Phe Gln Glu Cys Gly Leu Trp Val
625                 630                 635                 640
Leu Thr Asp Ala Asn Leu Thr Lys Asp Tyr Ile Asp Gly Val Tyr Asp
                645                 650                 655
Asn Ala Glu Tyr Ala Glu Arg Phe Met Glu Glu Asn Glu Gly His Ile
            660                 665                 670
Val Asp Ile His Asp Phe Ser Leu Gly Ser Ser Pro His Val Arg Lys
        675                 680                 685
His Phe Pro Glu Thr Trp Ile Trp Leu Asp Thr Asn Met Gly Xaa Arg
    690                 695                 700
```

```
Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
            725                 730                 735

Thr Thr Pro Val Glu Leu Gln Ala Phe Gln Pro Phe Phe Ile Phe Leu
            740                 745                 750

Asn Leu Pro Tyr Ser Val Arg Gly Glu Phe Ala Leu Glu Ile
            755                 760                 765

Thr Ile Phe Asn Tyr Leu Lys Asp Ala Thr Glu Val Lys Val Ile Ile
770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
                805                 810                 815

Thr Val Leu Phe Pro Ile Arg Pro Thr His Leu Gly Glu Ile Pro Ile
            820                 825                 830

Thr Val Thr Ala Leu Ser Pro Thr Ala Ser Asp Ala Val Thr Gln Met
            835                 840                 845

Ile Leu Val Lys Ala Glu Gly Ile Glu Lys Ser Tyr Ser Gln Ser Ile
850                 855                 860

Leu Leu Asp Leu Thr Asp Asn Arg Leu Gln Ser Thr Leu Lys Thr Leu
865                 870                 875                 880

Ser Phe Ser Phe Pro Pro Asn Thr Val Thr Gly Ser Glu Arg Val Gln
                885                 890                 895

Ile Thr Ala Ile Gly Asp Val Leu Gly Pro Ser Ile Asn Gly Leu Ala
            900                 905                 910

Ser Leu Ile Arg Met Pro Tyr Gly Cys Gly Glu Gln Asn Met Ile Asn
            915                 920                 925

Phe Ala Pro Asn Ile Tyr Ile Leu Asp Tyr Leu Thr Lys Lys Gln
930                 935                 940

Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
                965                 970                 975

Phe Gly Asn Tyr Asp Pro Ser Gly Ser Thr Trp Leu Ser Ala Phe Val
            980                 985                 990

Leu Arg Cys Phe Leu Glu Ala Asp Pro Tyr Ile Asp Ile Asp Gln Asn
            995                 1000                1005

Val Leu His Arg Thr Tyr Thr Trp Leu Lys Gly His Gln Lys Ser
    1010                1015                1020

Asn Gly Glu Phe Trp Asp Pro Gly Arg Val Ile His Ser Glu Leu
    1025                1030                1035

Gln Gly Gly Asn Lys Ser Pro Val Thr Leu Thr Ala Tyr Ile Val
    1040                1045                1050

Thr Ser Leu Leu Gly Tyr Arg Lys Tyr Gln Pro Asn Ile Asp Val
    1055                1060                1065

Gln Glu Ser Ile His Phe Leu Glu Ser Glu Phe Ser Arg Gly Ile
    1070                1075                1080

Ser Asp Asn Tyr Thr Leu Ala Leu Ile Thr Tyr Ala Leu Ser Ser
    1085                1090                1095

Val Gly Ser Pro Lys Ala Lys Glu Ala Leu Asn Met Leu Thr Trp
    1100                1105                1110
```

```
Arg Ala Glu Gln Glu Gly Gly Met Gln Phe Trp Val Ser Ser Glu
1115                1120                1125

Ser Lys Leu Ser Asp Ser Trp Gln Pro Arg Ser Leu Asp Ile Glu
1130                1135                1140

Val Ala Ala Tyr Ala Leu Leu Ser His Phe Leu Gln Phe Gln Thr
1145                1150                1155

Ser Glu Gly Ile Pro Ile Met Arg Trp Leu Ser Arg Gln Arg Asn
1160                1165                1170

Ser Leu Gly Gly Phe Ala Ser Thr Gln Asp Thr Thr Val Ala Leu
1175                1180                1185

Lys Ala Leu Ser Glu Phe Ala Ala Leu Met Asn Thr Glu Arg Thr
1190                1195                1200

Asn Ile Gln Val Thr Val Thr Gly Pro Ser Ser Pro Ser Pro Leu
1205                1210                1215

Ala Val Val Gln Pro Thr Ala Val Asn Ile Ser Ala Asn Gly Phe
1220                1225                1230

Gly Phe Ala Ile Cys Gln Leu Asn Val Val Tyr Asn Val Lys Ala
1235                1240                1245

Ser Gly Ser Ser Arg Arg Arg Arg Ser Ile Gln Asn Gln Glu Ala
1250                1255                1260

Phe Asp Leu Asp Val Ala Val Lys Glu Asn Lys Asp Asp Leu Asn
1265                1270                1275

His Val Asp Leu Asn Val Cys Thr Ser Phe Ser Gly Pro Gly Arg
1280                1285                1290

Ser Gly Met Ala Leu Met Glu Val Asn Leu Leu Ser Gly Phe Met
1295                1300                1305

Val Pro Ser Glu Ala Ile Ser Leu Ser Glu Thr Val Lys Lys Val
1310                1315                1320

Glu Tyr Asp His Gly Lys Leu Asn Leu Tyr Leu Asp Ser Val Asn
1325                1330                1335

Glu Thr Gln Phe Cys Val Asn Ile Pro Ala Val Arg Asn Phe Lys
1340                1345                1350

Val Ser Asn Thr Gln Asp Ala Ser Val Ser Ile Val Asp Tyr Tyr
1355                1360                1365

Glu Pro Arg Arg Gln Ala Val Arg Ser Tyr Asn Ser Glu Val Lys
1370                1375                1380

Leu Ser Ser Cys Asp Leu Cys Ser Asp Val Gln Gly Cys Arg Pro
1385                1390                1395

Cys Glu Asp Gly Ala Ser Gly Ser His His His Ser Ser Val Ile
1400                1405                1410

Phe Ile Phe Cys Phe Lys Leu Leu Tyr Phe Met Glu Leu Trp Leu
1415                1420                1425

<210> SEQ ID NO 3
<211> LENGTH: 5883
<212> TYPE: DNA
<213> ORGANISM: Homo sapiens
<220> FEATURE:
<221> NAME/KEY: misc_feature
<222> LOCATION: (2220)..(2220)
<223> OTHER INFORMATION: X = A or C

<400> SEQUENCE: 3
ctaaactcga attaagaggg aaaaaaaatc agggaggagg tggcaagcca caccccacgg      60
tgcccgcgaa cttccccggc agcggactgt agcccaggca gacgccgtcg agatgcaggg     120
```

-continued

```
cccaccgctc ctgaccgccg cccacctcct ctgcgtgtgc accgccgcgc tggccgtggc    180
tcccgggcct cggtttctgg tgacagcccc agggatcatc aggcccggag gaaatgtgac    240
tattggggtg gagcttctgg aacactgccc ttcacaggtg actgtgaagg cggagctgct    300
caagacagca tcaaacctca ctgtctctgt cctggaagca gaaggagtct ttgaaaaagg    360
ctcttttaag acacttactc ttccatcact acctctgaac agtgcagatg agatttatga    420
gctacgtgta accggacgta cccaggatga gattttattc tctaatagta cccgcttatc    480
atttgagacc aagagaatat ctgtcttcat tcaaacagac aaggcttat acaagccaaa     540
gcaagaagtg aagtttcgca ttgttacact cttctcagat tttaagcctt acaaaacctc    600
tttaaacatt tcattaagg accccaaatc aaatttgatc caacagtggt tgtcacaaca     660
aagtgatctt ggagtcattt ccaaaacttt tcagctatct tcccatccaa tacttggtga    720
ctggtctatt caagttcaag tgaatgacca gacatattat caatcatttc aggtttcaga    780
atatgtatta ccaaaatttg aagtgacttt gcagacacca ttatattgtt ctatgaattc    840
taagcattta aatggtacca tcacggcaaa gtatacatat gggaagccag tgaaaggaga    900
cgtaacgctt acatttttac ctttatcctt ttggggaaag aagaaaaata ttacaaaaac    960
atttaagata aatggatctg caaacttctc ttttaatgat gaagagatga aaatgtaat    1020
ggattcttca aatggacttt ctgaatacct ggatctatct tcccctggac cagtagaaat   1080
tttaaccaca gtgacagaat cagttacagg tatttcaaga aatgtaagca ctaatgtgtt   1140
cttcaagcaa catgattaca tcattgagtt ttttgattat actactgtct tgaagccatc   1200
tctcaacttc acagccactg tgaaggtaac tcgtgctgat ggcaaccaac tgactcttga   1260
agaaagaaga aataatgtag tcataacagt gacacagaga aactatactg agtactggag   1320
cggatctaac agtggaaatc agaaaatgga agctgttcag aaaataaatt atactgtccc   1380
ccaaagtgga acttttaaga ttgaattccc aatcctggag gattccagtg agctacagtt   1440
gaaggcctat ttccttggta gtaaaagtag catggcagtt catagtctgt ttaagtctcc   1500
tagtaagaca tacatccaac taaaaacaag agatgaaaat ataaaggtgg gatcgccttt   1560
tgagttggtg gttagtggca acaaacgatt gaaggagtta agctatatgg tagtatccag   1620
gggacagttg gtggctgtag aaaacaaaa ttcaacaatg ttctctttaa caccagaaaa    1680
ttcttggact ccaaaagcct gtgtaattgt gtattatatt gaagatgatg gggaaattat   1740
aagtgatgtt ctaaaaattc ctgttcagct tgttttttaaa aataagataa agctatattg   1800
gagtaaagtg aaagctgaac catctgagaa agtctctctt aggatctctg tgacacagcc   1860
tgactccata gttgggattg tagctgttga caaaagtgtg aatctgatga atgcctctaa   1920
tgatattaca atgaaaatg tggtccatga gttggaactt tataacacag gatattattt    1980
aggcatgttc atgaattctt ttgcagtctt tcaggaatgt ggactctggg tattgacaga   2040
tgcaaacctc acgaaggatt atattgatgg tgtttatgac aatgcagaat atgctgagag   2100
gtttatggag gaaatgaag gacatattgt agatattcat gactttcctt tgggtagcag    2160
tccacatgtc cgaaagcatt ttccagagac ttggatttgg ctagacacca acatgggttn   2220
caggatttac caagaatttg aagtaactgt acctgattct atcacttctt gggtggctac   2280
tggttttgtg atctctgagg acctgggtct tggactaaca actactccag tggagctcca   2340
agccttccaa ccattttca tttttttgaa tcttccctac tctgttatca gaggtgaaga   2400
atttgctttg gaaataacta tattcaatta tttgaaagat gccactgagg ttaaggtaat   2460
cattgagaaa agtgacaaat ttgatattct aatgacttca aatgaaataa atgccacagg   2520
```

-continued

```
ccaccagcag acccttctgg ttcccagtga ggatggggca actgttcttt ttcccatcag   2580
gccaacacat ctgggagaaa ttcctatcac agtcacagct ctttcaccca ctgcttctga   2640
tgctgtcacc cagatgattt tagtaaaggc tgaaggaata gaaaaatcat attcacaatc   2700
catcttatta gacttgactg acaataggct acagagtacc ctgaaaactt tgagtttctc   2760
atttcctcct aatacagtga ctggcagtga aagagttcag atcactgcaa ttggagatgt   2820
tcttggtcct tccatcaatg cttagcctc attgattcgg atgccttatg ctgtggtga    2880 acagaacatg ataaattttg ctccaaatat ttacattttg gattatctga ctaaaaagaa   2940
acaactgaca gataatttga agaaaaagc tctttcattt atgaggcaag gttaccagag    3000
agaacttctc tatcagaggg aagatggctc tttcagtgct tttgggaatt atgacccttc   3060
tgggagcact tggttgtcag cttttgtttt aagatgtttc cttgaagccg atccttacat   3120
agatattgat cagaatgtgt tacacagaac atacacttgg cttaaaggac atcagaaatc   3180
caacggtgaa ttttgggatc caggaagagt gattcatagt gagcttcaag gtggcaataa   3240
aagtccagta acacttacag cctatattgt aacttctctc ctgggatata gaaagtatca   3300
gcctaacatt gatgtgcaag agtctatcca ttttttggag tctgaattca gtagaggaat   3360
ttcagacaat tatactctag cccttataac ttatgcattg tcatcagtgg ggagtcctaa   3420
agcgaaggaa gctttgaata tgctgacttg gagagcagaa caagaaggtg gcatgcaatt   3480
ctgggtgtca tcagagtcca aactttctga ctcctggcag ccacgctccc tggatattga   3540
agttgcagcc tatgcactgc tctcacactt cttacaattt cagacttctg agggaatccc   3600
aattatgagg tggctaagca ggcaaagaaa tagcttgggt ggttttgcat ctactcagga   3660
taccactgtg gctttaaagg ctctgtctga atttgcagcc ctaatgaata cagaaaggac   3720
aaatatccaa gtgaccgtga cggggcctag ctcaccaagt cctgtaaagt ttctgattga   3780
cacacacaac cgcttactcc ttcagacagc agagcttgct gtggtacagc caatggcagt   3840
taatatttcc gcaaatggtt ttggatttgc tatttgtcag ctcaatgttg tatataatgt   3900
gaaggcttct gggtcttcta aagacgaag atctatccaa aatcaagaag cctttgattt    3960
agatgttgct gtaaaagaaa ataaagatga tctcaatcat gtggatttga atgtgtgtac   4020
aagcttttcg ggcccgggta ggagtggcat ggctcttatg gaagttaacc tattaagtgg   4080
ctttatggtg ccttcagaag caatttctct gagcgagaca gtgaagaaag tggaatatga   4140
tcatggaaaa ctcaacctct atttagattc tgtaaatgaa acccagtttt gtgttaatat   4200
tcctgctgtg agaaacttta agtttcaaa tacccaagat gcttcagtgt ccatagtgga    4260
ttactatgag ccaaggagac aggcggtgag aagttacaac tctgaagtga agctgtcctc   4320
ctgtgacctt tgcagtgatg tccagggctg ccgtccttgt gaggatggag cttcaggctc   4380
ccatcatcac tcttcagtca ttttttatttt ctgtttcaag cttctgtact ttatggaact   4440
ttggctgtga tttattttta aaggactctg tgtaacacta acatttccag tagtcacatg   4500
tgattgtttt gttttcgtag aagaatactg cttctatttt gaaaaagag ttttttttct    4560 ttctatgggg ttgcagggat ggtgtacaac aggtcctagc atgtatagct gcatagattt   4620
cttcacctga tctttgtgtg gaagatcaga atgaatgcag ttgtgtgtct atattttccc   4680
ctcacaaaat cttttagaat tttttttggag gtgtttgttt tctccagaat aaaggtatta   4740
ctttagaaat aggtattctc ctcatttttgt gaaagaaatg aacctagatt cttaagcatt   4800
attacacatc catgtttgct taaagatgga tttccctggg aatgggagaa aacagccagc   4860
```

```
aggaggagct tcatctgttc ccttcccacc tccaacctag ccctactgcc caccccaccc    4920
caacccaccc catgcccagt ggtctcagta gatacttctt aactgaaaat tctttctttt    4980
cagaatctag gtggtgaatt ttttttaagt ggcacggtct ttttctgctt gaaatctgat    5040
cacacccccc agccattgcc ctccctctct ttttcctctg tagagaaatg tgaggggcag    5100
tacatttact gtgcttttca caccatctca gaggttgagg agcatactga aaattgccct    5160 gggggtgct gggtgtgctg tctccttccc acatcctcag ccccacacca gctctatttc    5220 agggtgaga gtcagagagc actgcaatat gtgcttcatg ggatttcgat tcgaagatcc    5280
tagaccaggg agacactgtg agccagggat acaacaaaat actaggtaag tcactgcaga    5340
ccgacctccc tgcagtttgg gaaagaagct gggtttgtgg agaatcagag catcttgaca    5400
tgactgctga cctaaagatc cctggcattg gccagggatc ctgtggaacc tcttctagtt    5460
caggggtgtg agcattagac tgccagttgt ctagtgacat ctgatgcttg ctgtgaactt    5520
ttaagatccc cgaatcctga gcacctcaat ctttaattgc cctgtattcc gaagggtaat    5580
ataatttatc tggatggaaa ttttaaagat gaatcccct ttttctttt cttctctctt    5640 ttctttcctt ctccctttct tctttgcctt ctaaatatac tgaaatgatt tagatatgtg    5700
tcaacaatta atgatctttt attcaatcta agaaatggtt tagtttttct ctttagctct    5760
atggcatttc actcaagtgg acaggggaaa aagtaattgc catgggctcc aaagaatttg    5820
ctttatgttt ttagctattt aaaaataaat ccatcaaaaa taaagtatgc aaatgtatct    5880
ttt                                                                  5883

<210> SEQ ID NO 4
<211> LENGTH: 1445
<212> TYPE: PRT
<213> ORGANISM: Homo sapiens
<220> FEATURE:
<221> NAME/KEY: MISC_FEATURE
<222> LOCATION: (703)..(703)
<223> OTHER INFORMATION: Xaa = Ser or Tyr

<400> SEQUENCE: 4
```

Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
    50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile

-continued

```
                165                 170                 175
Gln Gln Trp Leu Ser Gln Ser Asp Leu Gly Val Ile Ser Lys Thr
                180                 185                 190

Phe Gln Leu Ser Ser His Pro Ile Leu Gly Asp Trp Ser Ile Gln Val
            195                 200                 205

Gln Val Asn Asp Gln Thr Tyr Tyr Gln Ser Phe Gln Val Ser Glu Tyr
            210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Asn Ile Thr Lys Thr Phe Lys Ile Asn Gly
        275                 280                 285

Ser Ala Asn Phe Ser Phe Asn Asp Glu Glu Met Lys Asn Val Met Asp
            290                 295                 300

Ser Ser Asn Gly Leu Ser Glu Tyr Leu Asp Leu Ser Ser Pro Gly Pro
305                 310                 315                 320

Val Glu Ile Leu Thr Thr Val Thr Glu Ser Val Thr Gly Ile Ser Arg
                325                 330                 335

Asn Val Ser Thr Asn Val Phe Phe Lys Gln His Asp Tyr Ile Ile Glu
            340                 345                 350

Phe Phe Asp Tyr Thr Thr Val Leu Lys Pro Ser Leu Asn Phe Thr Ala
        355                 360                 365

Thr Val Lys Val Thr Arg Ala Asp Gly Asn Gln Leu Thr Leu Glu Glu
        370                 375                 380

Arg Arg Asn Asn Val Val Ile Thr Val Thr Gln Arg Asn Tyr Thr Glu
385                 390                 395                 400

Tyr Trp Ser Gly Ser Asn Ser Gly Asn Gln Lys Met Glu Ala Val Gln
                405                 410                 415

Lys Ile Asn Tyr Thr Val Pro Gln Ser Gly Thr Phe Lys Ile Glu Phe
            420                 425                 430

Pro Ile Leu Glu Asp Ser Ser Glu Leu Gln Leu Lys Ala Tyr Phe Leu
        435                 440                 445

Gly Ser Lys Ser Ser Met Ala Val His Ser Leu Phe Lys Ser Pro Ser
        450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                485                 490                 495

Ser Tyr Met Val Val Ser Arg Gly Gln Leu Val Ala Val Gly Lys Gln
                500                 505                 510

Asn Ser Thr Met Phe Ser Leu Thr Pro Glu Asn Ser Trp Thr Pro Lys
            515                 520                 525

Ala Cys Val Ile Val Tyr Tyr Ile Glu Asp Asp Gly Glu Ile Ile Ser
        530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
                565                 570                 575

Arg Ile Ser Val Thr Gln Pro Asp Ser Ile Val Gly Ile Val Ala Val
            580                 585                 590
```

```
Asp Lys Ser Val Asn Leu Met Asn Ala Ser Asn Asp Ile Thr Met Glu
            595                 600                 605

Asn Val Val His Glu Leu Glu Leu Tyr Asn Thr Gly Tyr Tyr Leu Gly
        610                 615                 620

Met Phe Met Asn Ser Phe Ala Val Phe Gln Glu Cys Gly Leu Trp Val
625                 630                 635                 640

Leu Thr Asp Ala Asn Leu Thr Lys Asp Tyr Ile Asp Gly Val Tyr Asp
                645                 650                 655

Asn Ala Glu Tyr Ala Glu Arg Phe Met Glu Glu Asn Glu Gly His Ile
            660                 665                 670

Val Asp Ile His Asp Phe Ser Leu Gly Ser Ser Pro His Val Arg Lys
        675                 680                 685

His Phe Pro Glu Thr Trp Ile Trp Leu Asp Thr Asn Met Gly Xaa Arg
    690                 695                 700

Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
                725                 730                 735

Thr Thr Pro Val Glu Leu Gln Ala Phe Gln Pro Phe Ile Phe Leu
            740                 745                 750

Asn Leu Pro Tyr Ser Val Ile Arg Gly Glu Phe Ala Leu Glu Ile
        755                 760                 765

Thr Ile Phe Asn Tyr Leu Lys Asp Ala Thr Glu Val Lys Val Ile Ile
    770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
                805                 810                 815

Thr Val Leu Phe Pro Ile Arg Pro Thr His Leu Gly Glu Ile Pro Ile
            820                 825                 830

Thr Val Thr Ala Leu Ser Pro Thr Ala Ser Asp Ala Val Thr Gln Met
        835                 840                 845

Ile Leu Val Lys Ala Glu Gly Ile Glu Lys Ser Tyr Ser Gln Ser Ile
    850                 855                 860

Leu Leu Asp Leu Thr Asp Asn Arg Leu Gln Ser Thr Leu Lys Thr Leu
865                 870                 875                 880

Ser Phe Ser Phe Pro Pro Asn Thr Val Thr Gly Ser Glu Arg Val Gln
                885                 890                 895

Ile Thr Ala Ile Gly Asp Val Leu Gly Pro Ser Ile Asn Gly Leu Ala
            900                 905                 910

Ser Leu Ile Arg Met Pro Tyr Gly Cys Gly Glu Gln Asn Met Ile Asn
        915                 920                 925

Phe Ala Pro Asn Ile Tyr Ile Leu Asp Tyr Leu Thr Lys Lys Gln
    930                 935                 940

Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
                965                 970                 975

Phe Gly Asn Tyr Asp Pro Ser Gly Ser Thr Trp Leu Ser Ala Phe Val
            980                 985                 990

Leu Arg Cys Phe Leu Glu Ala Asp  Pro Tyr Ile Asp Ile  Asp Gln Asn
        995                 1000                1005
```

-continued

Val Leu His Arg Thr Tyr Thr Trp Leu Lys Gly His Gln Lys Ser
1010                1015                1020

Asn Gly Glu Phe Trp Asp Pro Gly Arg Val Ile His Ser Glu Leu
1025                1030                1035

Gln Gly Gly Asn Lys Ser Pro Val Thr Leu Thr Ala Tyr Ile Val
1040                1045                1050

Thr Ser Leu Leu Gly Tyr Arg Lys Tyr Gln Pro Asn Ile Asp Val
1055                1060                1065

Gln Glu Ser Ile His Phe Leu Glu Ser Glu Phe Ser Arg Gly Ile
1070                1075                1080

Ser Asp Asn Tyr Thr Leu Ala Leu Ile Thr Tyr Ala Leu Ser Ser
1085                1090                1095

Val Gly Ser Pro Lys Ala Lys Glu Ala Leu Asn Met Leu Thr Trp
1100                1105                1110

Arg Ala Glu Gln Glu Gly Gly Met Gln Phe Trp Val Ser Ser Glu
1115                1120                1125

Ser Lys Leu Ser Asp Ser Trp Gln Pro Arg Ser Leu Asp Ile Glu
1130                1135                1140

Val Ala Ala Tyr Ala Leu Leu Ser His Phe Leu Gln Phe Gln Thr
1145                1150                1155

Ser Glu Gly Ile Pro Ile Met Arg Trp Leu Ser Arg Gln Arg Asn
1160                1165                1170

Ser Leu Gly Gly Phe Ala Ser Thr Gln Asp Thr Thr Val Ala Leu
1175                1180                1185

Lys Ala Leu Ser Glu Phe Ala Ala Leu Met Asn Thr Glu Arg Thr
1190                1195                1200

Asn Ile Gln Val Thr Val Thr Gly Pro Ser Ser Pro Ser Pro Val
1205                1210                1215

Lys Phe Leu Ile Asp Thr His Asn Arg Leu Leu Leu Gln Thr Ala
1220                1225                1230

Glu Leu Ala Val Val Gln Pro Met Ala Val Asn Ile Ser Ala Asn
1235                1240                1245

Gly Phe Gly Phe Ala Ile Cys Gln Leu Asn Val Val Tyr Asn Val
1250                1255                1260

Lys Ala Ser Gly Ser Ser Arg Arg Arg Arg Ser Ile Gln Asn Gln
1265                1270                1275

Glu Ala Phe Asp Leu Asp Val Ala Val Lys Glu Asn Lys Asp Asp
1280                1285                1290

Leu Asn His Val Asp Leu Asn Val Cys Thr Ser Phe Ser Gly Pro
1295                1300                1305

Gly Arg Ser Gly Met Ala Leu Met Glu Val Asn Leu Leu Ser Gly
1310                1315                1320

Phe Met Val Pro Ser Glu Ala Ile Ser Leu Ser Glu Thr Val Lys
1325                1330                1335

Lys Val Glu Tyr Asp His Gly Lys Leu Asn Leu Tyr Leu Asp Ser
1340                1345                1350

Val Asn Glu Thr Gln Phe Cys Val Asn Ile Pro Ala Val Arg Asn
1355                1360                1365

Phe Lys Val Ser Asn Thr Gln Asp Ala Ser Val Ser Ile Val Asp
1370                1375                1380

Tyr Tyr Glu Pro Arg Arg Gln Ala Val Arg Ser Tyr Asn Ser Glu
1385                1390                1395

Val Lys Leu Ser Ser Cys Asp Leu Cys Ser Asp Val Gln Gly Cys

-continued

```
            1400                1405                1410
Arg Pro Cys Glu Asp Gly Ala Ser Gly Ser His  His His Ser Ser
    1415                1420                    1425

Val Ile Phe Ile Phe Cys Phe Lys Leu Leu Tyr Phe Met Glu Leu
    1430                1435                    1440

Trp Leu
    1445

<210> SEQ ID NO 5
<211> LENGTH: 4234
<212> TYPE: DNA
<213> ORGANISM: Homo sapiens
<220> FEATURE:
<221> NAME/KEY: misc_feature
<222> LOCATION: (2133)..(2133)
<223> OTHER INFORMATION: N = A or C

<400> SEQUENCE: 5
tgtagcccag gcagacgccg tcgagatgca gggcccaccg ctcctgaccg ccgcccacct      60
cctctgcgtg tgcaccgccg cgctggccgt ggctcccggg cctcggtttc tggtgacagc     120
cccagggatc atcaggcccg aggaaatgt gactattggg tggagcttc tggaacactg      180 cccttcacag gtgactgtga aggcggagct gctcaagaca gcatcaaacc tcactgtctc     240
tgtcctggaa gcagaaggag tctttgaaaa aggctctttt aagacactta ctcttccatc     300
actacctctg aacagtgcag atgagattta tgagctacgt gtaaccggac gtacccagga     360
tgagatttta ttctctaata gtacccgctt atcatttgag accaagagaa tatctgtctt     420
cattcaaaca gacaaggcct tatacaagcc aaagcaagaa gtgaagtttc gcattgttac     480
actcttctca gattttaagc cttacaaaac ctcttaaac attctcatta aggaccccaa     540
atcaaatttg atccaacagt ggttgtcaca acaaagtgat cttggagtca tttccaaaac     600
ttttcagcta tcttcccatc caatacttgg tgactggtct attcaagttc aagtgaatga     660
ccagacatac tatcaatcat ttcaggtttc agaatatgta ttaccaaaat ttgaagtgac     720
tttgcagaca ccattatatt gttctatgaa ttctaagcat ttaaatggta ccatcacggc     780
aaagtataca tatgggaagc cagtgaaagg agacgtaacg cttacatttt tacctttatc     840
cttttgggga aagaagaaaa atattacaaa aacatttaag ataaatggat ctgcaaactt     900 ctctttttaat gatgaagaga tgaaaaatgt aatggattct tcaaatggac tttctgaata     960
cctggatcta tcttccccctg accagtaga aatttttaacc acagtgacag aatcagttac    1020
aggtatttca agaaatgtaa gcactaatgt gttcttcaag caacatgatt acatcattga    1080 gtttttttgat tatactactg tcttgaagcc atctctcaac ttcacagcca ctgtgaaggt    1140
aactcgtgct gatggcaacc aactgactct tgaagaaaga agaaataatg tagtcataac    1200
agtgacacag agaaactata ctgagtactg gagcggatct aacagtggaa atcagaaaat    1260
ggaagctgtt cagaaaataa attatactgt cccccaaagt ggaactttta agattgaatt    1320
cccaatcctg gaggattcca gtgagctaca gttgaaggcc tatttccttg gtagtaaaag    1380
tagcatggca gttcatagtc tgtttaagtc tcctagtaag acatacatcc aactaaaaac    1440
aagagatgaa aatataaagg tgggatcgcc ttttgagttg gtggttagtg gcaacaaacg    1500
attgaaggag ttaagctata tggtagtatc cagggggacag ttggtggctg taggaaaaca    1560
aaattcaaca atgttctctt taacaccaga aaattcttgg actccaaaag cctgtgtaat    1620
tgtgtattat attgaagatg atgggaaat tataagtgat gttctaaaaa ttcctgttca    1680
```

-continued

```
gcttgttttt aaaaataaga taaagctata ttggagtaaa gtgaaagctg aaccatctga    1740
gaaagtctct cttaggatct ctgtgacaca gcctgactcc atagttggga ttgtagctgt    1800
tgacaaaagt gtgaatctga tgaatgcctc taatgatatt acaatggaaa atgtggtcca    1860
tgagttggaa ctttataaca caggatatta tttaggcatg ttcatgaatt cttttgcagt    1920
ctttcaggaa tgtggactct gggtattgac agatgcaaac ctcacgaagg attatattga    1980
tggtgtttat gacaatgcag aatatgctga gaggtttatg gaggaaaatg aaggacatat    2040
tgtagatatt catgactttt ctttgggtag cagtccacat gtccgaaagc attttccaga    2100
gacttggatt tggctagaca ccaacatggg ttncaggatt taccaagaat ttgaagtaac    2160
tgtacctgat tctatcactt cttgggtggc tactggtttt gtgatctctg aggacctggg    2220
tcttggacta acaactactc cagtggagct ccaagccttc caaccatttt tcattttttt    2280
gaatcttccc tactctgtta tcagaggtga agaatttgct ttggaaataa ctatattcaa    2340
ttatttgaaa gatgccactg aggttaaggt aatcattgag aaaagtgaca aatttgatat    2400
tctaatgact tcaaatgaaa taaatgccac aggccaccag cagacccttc tggttcccag    2460
tgaggatggg gcaactgttc ttttccccat caggccaaca catctgggag aaattcctat    2520
cacagtcaca gctctttcac ccactgcttc tgatgctgtc acccagatga ttttagtaaa    2580
ggctgaagga atagaaaaat catattcaca atccatctta ttagacttga ctgacaatag    2640
gctacagagt accctgaaaa ctttgagttt ctcatttcct cctaatacag tgactggcag    2700
tgaaagagtt cagatcactg caattggaga tgttcttggt ccttccatca atggcttagc    2760
ctcattgatt cggatgcctt atggctgtgg tgaacagaac atgataaatt ttgctccaaa    2820
tatttacatt ttggattatc tgactaaaaa gaaacaactg acagataatt tgaaagaaaa    2880
agctctttca tttatgaggc aaggttacca gagagaactt ctctatcaga gggaagatgg    2940
ctctttcagt gcttttggga attatgaccc ttctgggagc acttggttgt cagcttttgt    3000
tttaagatgt ttccttgaag ccgatcctta catagatatt gatcagaatg tgttacacag    3060
aacatacact tggcttaaag gacatcagaa atccaacggt gaattttggg atccaggaag    3120
agtgattcat agtgagcttc aaggtggcaa taaaagtcca gtaacactta cagcctatat    3180
tgtaacttct ctcctgggat atagaaagta tcagcctaac attgatgtgc aagagtctat    3240 ccatttttg gagtctgaat tcagtagagg aatttcagac aattatactc tagcccttat    3300
aacttatgca ttgtcatcag tggggagtcc taaagcgaag gaagctttga atatgctgac    3360
ttggagagca gaacaagaag gtggcatgca attctgggtg tcatcagagt ccaaactttc    3420
tgactcctgg cagccacgct ccctggatat tgaagttgca gcctatgcac tgctctcaca    3480
cttcttacaa tttcagactt ctgagggaat cccaattatg aggtggctaa gcaggcaaag    3540
aaatagcttg ggtggttttg catctactca ggataccact gtggctttaa aggctctgtc    3600
tgaatttgca gccctaatga atacagaaag gacaaatatc caagtgaccg tgacggggcc    3660
tagctcacca agtcctcttg ctgtggtaca gccaacggca gttaatattt ccgcaaatgg    3720
ttttggattt gctatttgtc agctcaatgt tgtatataat gtgaaggctt ctgggtcttc    3780
tagaagacga agatctatcc aaaatcaaga agcctttgat ttagatgttg ctgtaaaaga    3840
aaataaagat gatctcaatc atgtggattt gaatgtgtgt acaagctttt cgggcccggg    3900
taggagtggc atggctctta tggaagttaa cctattaagt ggctttatgg tgccttcaga    3960
agcaatttct ctgagcgaga cagtgaagaa agtggaatat gatcatggaa aactcaacct    4020
ctatttagat tctgtaaatg aaacccagtt ttgtgttaat attcctgctg tgagaaactt    4080
```

-continued

```
taaagtttca aatacccaag atgcttcagt gtccatagtg gattactatg agccaaggag    4140
acaggcggtg agaagttaca actctgaagt gaagctgtcc tcctgtgacc tttgcagtga    4200
tgtccagggc tgccgtcctt gtgaggatgg agct                                4234
```

<210> SEQ ID NO 6
<211> LENGTH: 1403
<212> TYPE: PRT
<213> ORGANISM: Homo sapiens
<220> FEATURE:
<221> NAME/KEY: MISC_FEATURE
<222> LOCATION: (703)..(703)
<223> OTHER INFORMATION: Xaa = Ser or Tyr

<400> SEQUENCE: 6

```
Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
    50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Asn Ile Thr Lys Thr Phe Lys Ile Asn Gly
        275                 280                 285

Ser Ala Asn Phe Ser Phe Asn Asp Glu Glu Met Lys Asn Val Met Asp
    290                 295                 300

Ser Ser Asn Gly Leu Ser Glu Tyr Leu Asp Leu Ser Ser Pro Gly Pro
305                 310                 315                 320
```

```
Val Glu Ile Leu Thr Thr Val Thr Glu Ser Val Thr Gly Ile Ser Arg
                325                 330                 335

Asn Val Ser Thr Asn Val Phe Phe Lys Gln His Asp Tyr Ile Ile Glu
            340                 345                 350

Phe Phe Asp Tyr Thr Thr Val Leu Lys Pro Ser Leu Asn Phe Thr Ala
        355                 360                 365

Thr Val Lys Val Thr Arg Ala Asp Gly Asn Gln Leu Thr Leu Glu Glu
    370                 375                 380

Arg Arg Asn Asn Val Val Ile Thr Val Thr Gln Arg Asn Tyr Thr Glu
385                 390                 395                 400

Tyr Trp Ser Gly Ser Asn Ser Gly Asn Gln Lys Met Glu Ala Val Gln
                405                 410                 415

Lys Ile Asn Tyr Thr Val Pro Gln Ser Gly Thr Phe Lys Ile Glu Phe
            420                 425                 430

Pro Ile Leu Glu Asp Ser Ser Glu Leu Gln Leu Lys Ala Tyr Phe Leu
        435                 440                 445

Gly Ser Lys Ser Ser Met Ala Val His Ser Leu Phe Lys Ser Pro Ser
    450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                485                 490                 495

Ser Tyr Met Val Val Ser Arg Gly Gln Leu Val Ala Val Gly Lys Gln
            500                 505                 510

Asn Ser Thr Met Phe Ser Leu Thr Pro Glu Asn Ser Trp Thr Pro Lys
        515                 520                 525

Ala Cys Val Ile Val Tyr Tyr Ile Glu Asp Asp Gly Glu Ile Ile Ser
    530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
                565                 570                 575

Arg Ile Ser Val Thr Gln Pro Asp Ser Ile Val Gly Ile Val Ala Val
            580                 585                 590

Asp Lys Ser Val Asn Leu Met Asn Ala Ser Asn Asp Ile Thr Met Glu
        595                 600                 605

Asn Val Val His Glu Leu Glu Leu Tyr Asn Thr Gly Tyr Tyr Leu Gly
    610                 615                 620

Met Phe Met Asn Ser Phe Ala Val Phe Gln Glu Cys Gly Leu Trp Val
625                 630                 635                 640

Leu Thr Asp Ala Asn Leu Thr Lys Asp Tyr Ile Asp Gly Val Tyr Asp
                645                 650                 655

Asn Ala Glu Tyr Ala Glu Arg Phe Met Glu Glu Asn Glu Gly His Ile
            660                 665                 670

Val Asp Ile His Asp Phe Ser Leu Gly Ser Ser Pro His Val Arg Lys
        675                 680                 685

His Phe Pro Glu Thr Trp Ile Trp Leu Asp Thr Asn Met Gly Xaa Arg
    690                 695                 700

Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
                725                 730                 735

Thr Thr Pro Val Glu Leu Gln Ala Phe Gln Pro Phe Phe Ile Phe Leu
```

-continued

```
                        740                 745                 750
Asn Leu Pro Tyr Ser Val Ile Arg Gly Glu Glu Phe Ala Leu Glu Ile
            755                 760                 765
Thr Ile Phe Asn Tyr Leu Lys Asp Ala Thr Glu Val Lys Val Ile Ile
        770                 775                 780
Glu Lys Ser Asp Lys Phe Asp Ile Leu Met Thr Ser Asn Glu Ile Asn
785                 790                 795                 800
Ala Thr Gly His Gln Gln Thr Leu Leu Val Pro Ser Glu Asp Gly Ala
                805                 810                 815
Thr Val Leu Phe Pro Ile Arg Pro Thr His Leu Gly Glu Ile Pro Ile
            820                 825                 830
Thr Val Thr Ala Leu Ser Pro Thr Ala Ser Asp Ala Val Thr Gln Met
        835                 840                 845
Ile Leu Val Lys Ala Glu Gly Ile Glu Lys Ser Tyr Ser Gln Ser Ile
850                 855                 860
Leu Leu Asp Leu Thr Asp Asn Arg Leu Gln Ser Thr Leu Lys Thr Leu
865                 870                 875                 880
Ser Phe Ser Phe Pro Pro Asn Thr Val Thr Gly Ser Glu Arg Val Gln
                885                 890                 895
Ile Thr Ala Ile Gly Asp Val Leu Gly Pro Ser Ile Asn Gly Leu Ala
            900                 905                 910
Ser Leu Ile Arg Met Pro Tyr Gly Cys Gly Glu Gln Asn Met Ile Asn
        915                 920                 925
Phe Ala Pro Asn Ile Tyr Ile Leu Asp Tyr Leu Thr Lys Lys Lys Gln
        930                 935                 940
Leu Thr Asp Asn Leu Lys Glu Lys Ala Leu Ser Phe Met Arg Gln Gly
945                 950                 955                 960
Tyr Gln Arg Glu Leu Leu Tyr Gln Arg Glu Asp Gly Ser Phe Ser Ala
                965                 970                 975
Phe Gly Asn Tyr Asp Pro Ser Gly Ser Thr Trp Leu Ser Ala Phe Val
            980                 985                 990
Leu Arg Cys Phe Leu Glu Ala Asp Pro Tyr Ile Asp Ile Asp Gln Asn
        995                 1000                1005
Val Leu His Arg Thr Tyr Thr Trp Leu Lys Gly His Gln Lys Ser
    1010                1015                1020
Asn Gly Glu Phe Trp Asp Pro Gly Arg Val Ile His Ser Glu Leu
    1025                1030                1035
Gln Gly Gly Asn Lys Ser Pro Val Thr Leu Thr Ala Tyr Ile Val
    1040                1045                1050
Thr Ser Leu Leu Gly Tyr Arg Lys Tyr Gln Pro Asn Ile Asp Val
    1055                1060                1065
Gln Glu Ser Ile His Phe Leu Glu Ser Glu Phe Ser Arg Gly Ile
    1070                1075                1080
Ser Asp Asn Tyr Thr Leu Ala Leu Ile Thr Tyr Ala Leu Ser Ser
    1085                1090                1095
Val Gly Ser Pro Lys Ala Lys Glu Ala Leu Asn Met Leu Thr Trp
    1100                1105                1110
Arg Ala Glu Gln Glu Gly Gly Met Gln Phe Trp Val Ser Ser Glu
    1115                1120                1125
Ser Lys Leu Ser Asp Ser Trp Gln Pro Arg Ser Leu Asp Ile Glu
    1130                1135                1140
Val Ala Ala Tyr Ala Leu Leu Ser His Phe Leu Gln Phe Gln Thr
    1145                1150                1155
```

-continued

| | | | | | | | | | | |
|---|---|---|---|---|---|---|---|---|---|---|
| Ser | Glu | Gly | Ile | Pro | Ile | Met | Arg | Trp | Leu | Ser | Arg | Gln | Arg | Asn |
| | 1160 | | | | | 1165 | | | | | 1170 | | | |
| Ser | Leu | Gly | Gly | Phe | Ala | Ser | Thr | Gln | Asp | Thr | Thr | Val | Ala | Leu |
| | 1175 | | | | | 1180 | | | | | 1185 | | | |
| Lys | Ala | Leu | Ser | Glu | Phe | Ala | Ala | Leu | Met | Asn | Thr | Glu | Arg | Thr |
| | 1190 | | | | | 1195 | | | | | 1200 | | | |
| Asn | Ile | Gln | Val | Thr | Val | Thr | Gly | Pro | Ser | Ser | Pro | Ser | Pro | Leu |
| | 1205 | | | | | 1210 | | | | | 1215 | | | |
| Ala | Val | Val | Gln | Pro | Thr | Ala | Val | Asn | Ile | Ser | Ala | Asn | Gly | Phe |
| | 1220 | | | | | 1225 | | | | | 1230 | | | |
| Gly | Phe | Ala | Ile | Cys | Gln | Leu | Asn | Val | Val | Tyr | Asn | Val | Lys | Ala |
| | 1235 | | | | | 1240 | | | | | 1245 | | | |
| Ser | Gly | Ser | Ser | Arg | Arg | Arg | Ser | Ile | Gln | Asn | Gln | Glu | Ala |
| | 1250 | | | | | 1255 | | | | | 1260 | | | |
| Phe | Asp | Leu | Asp | Val | Ala | Val | Lys | Glu | Asn | Lys | Asp | Asp | Leu | Asn |
| | 1265 | | | | | 1270 | | | | | 1275 | | | |
| His | Val | Asp | Leu | Asn | Val | Cys | Thr | Ser | Phe | Ser | Gly | Pro | Gly | Arg |
| | 1280 | | | | | 1285 | | | | | 1290 | | | |
| Ser | Gly | Met | Ala | Leu | Met | Glu | Val | Asn | Leu | Leu | Ser | Gly | Phe | Met |
| | 1295 | | | | | 1300 | | | | | 1305 | | | |
| Val | Pro | Ser | Glu | Ala | Ile | Ser | Leu | Ser | Glu | Thr | Val | Lys | Lys | Val |
| | 1310 | | | | | 1315 | | | | | 1320 | | | |
| Glu | Tyr | Asp | His | Gly | Lys | Leu | Asn | Leu | Tyr | Leu | Asp | Ser | Val | Asn |
| | 1325 | | | | | 1330 | | | | | 1335 | | | |
| Glu | Thr | Gln | Phe | Cys | Val | Asn | Ile | Pro | Ala | Val | Arg | Asn | Phe | Lys |
| | 1340 | | | | | 1345 | | | | | 1350 | | | |
| Val | Ser | Asn | Thr | Gln | Asp | Ala | Ser | Val | Ser | Ile | Val | Asp | Tyr | Tyr |
| | 1355 | | | | | 1360 | | | | | 1365 | | | |
| Glu | Pro | Arg | Arg | Gln | Ala | Val | Arg | Ser | Tyr | Asn | Ser | Glu | Val | Lys |
| | 1370 | | | | | 1375 | | | | | 1380 | | | |
| Leu | Ser | Ser | Cys | Asp | Leu | Cys | Ser | Asp | Val | Gln | Gly | Cys | Arg | Pro |
| | 1385 | | | | | 1390 | | | | | 1395 | | | |
| Cys | Glu | Asp | Gly | Ala |
| | 1400 | | | |

<210> SEQ ID NO 7
<211> LENGTH: 4372
<212> TYPE: DNA
<213> ORGANISM: Homo sapiens
<220> FEATURE:
<221> NAME/KEY: misc_feature
<222> LOCATION: (2220)..(2220)
<223> OTHER INFORMATION: N = A or C

<400> SEQUENCE: 7

| | | |
|---|---|---|
| ctaaactcga attaagaggg aaaaaaaatc agggaggagg tggcaagcca caccccacgg | 60 |
| tgcccgcgaa cttccccggc agcggactgt agcccaggca gacgccgtcg agatgcaggg | 120 |
| cccaccgctc ctgaccgccg cccacctcct ctgcgtgtgc accgccgcgc tggccgtggc | 180 |
| tcccgggcct cggtttctgg tgacagcccc aggatcatc aggcccggag gaaatgtgac | 240 |
| tattggggtg gagcttctgg aacactgccc ttcacaggtg actgtgaagg cggagctgct | 300 |
| caagacagca tcaaacctca ctgtctctgt cctggaagca gaaggagtct ttgaaaaagg | 360 |
| ctcttttaag acacttactc ttccatcact acctctgaac agtgcagatg agatttatga | 420 |
| gctacgtgta accggacgta cccaggatga gattttattc tctaatagta cccgcttatc | 480 |

```
atttgagacc aagagaatat ctgtcttcat tcaaacagac aaggccttat acaagccaaa      540
gcaagaagtg aagtttcgca ttgttacact cttctcagat tttaagcctt acaaaacctc      600
tttaaacatt ctcattaagg accccaaatc aaatttgatc caacagtggt tgtcacaaca      660
aagtgatctt ggagtcattt ccaaaacttt tcagctatct tcccatccaa tacttggtga      720
ctggtctatt caagttcaag tgaatgacca gacatattat caatcatttc aggtttcaga      780
atatgtatta ccaaaatttg aagtgacttt gcagacacca ttatattgtt ctatgaattc      840
taagcattta aatggtacca tcacggcaaa gtatacatat gggaagccag tgaaaggaga      900
cgtaacgctt acatttttac ctttatcctt tgggaaaag aagaaaaata ttacaaaaac      960
atttaagata aatggatctg caaacttctc ttttaatgat gaagagatga aaatgtaat      1020 ggattcttca aatggacttt ctgaatacct ggatctatct tcccctggac cagtagaaat      1080
tttaaccaca gtgacagaat cagttacagg tatttcaaga aatgtaagca ctaatgtgtt      1140
cttcaagcaa catgattaca tcattgagtt ttttgattat actactgtct tgaagccatc      1200
tctcaacttc acagccactg tgaaggtaac tcgtgctgat ggcaaccaac tgactcttga      1260
agaaagaaga aataatgtag tcataacagt gacacagaga aactatactg agtactggag      1320
cggatctaac agtggaaatc agaaaatgga agctgttcag aaaataaatt atactgtccc      1380
ccaaagtgga acttttaaga ttgaattccc aatcctggag gattccagtg agctacagtt      1440
gaaggcctat ttccttggta gtaaaagtag catggcagtt catagtctgt ttaagtctcc      1500
tagtaagaca tacatccaac taaaaacaag agatgaaaat ataaaggtgg atcgcctttt      1560
tgagttggtg gttagtggca acaaacgatt gaaggagtta agctatatgg tagtatccag      1620
gggacagttg gtggctgtag gaaaacaaa ttcaacaatg ttctctttaa caccagaaaa      1680
ttcttggact ccaaaagcct gtgtaattgt gtattatatt gaagatgatg gggaaattat      1740
aagtgatgtt ctaaaaattc ctgttcagct tgtttttaaa aataagataa agctatattg      1800
gagtaaagtg aaagctgaac catctgagaa agtctctctt aggatctctg tgacacagcc      1860
tgactccata gttgggattg tagctgttga caaaagtgtg aatctgatga atgcctctaa      1920
tgatattaca atggaaaatg tggtccatga gttggaactt tataacacag gatattattt      1980
aggcatgttc atgaattctt ttgcagtctt tcaggaatgt ggactctggg tattgacaga      2040
tgcaaacctc acgaaggatt atattgatgg tgtttatgac aatgcagaat atgctgagag      2100
gtttatggag gaaaatgaag gacatattgt agatattcat gacttttctt tgggtagcag      2160
tccacatgtc cgaaagcatt ttccagagac ttggatttgg ctagacacca acatgggttn      2220
caggatttac caagaatttg aagtaactgt acctgattct atcacttctt gggtggctac      2280
tggttttgtg atctctgagg acctgggtct tggactaaca actactccag tggagctcca      2340
agccttccaa ccatttttca tttttttgaa tcttccctac tctgttatca gaggtgaaga      2400
atttgctttg gaaataacta tattcaatta tttgaaagat gccactgagg ttaaggtaat      2460
cattgagaaa agtgacaaat tgatattct aatgacttca aatgaaataa atgccacagg      2520
ccaccagcag accttctgg ttcccagtga ggatgggca actgttcttt ttcccatcag      2580
gccaacacat ctgggagaaa ttcctatcac agtcacagct ctttcaccca ctgcttctga      2640
tgctgtcacc cagatgattt tagtaaaggc tgaaggaata gaaaaatcat attcacaatc      2700
catcttatta gacttgactg acaataggct acagagtacc ctgaaaactt tgagtttctc      2760
atttcctcct aatacagtga ctggcagtga aagagttcag atcactgcaa ttggagatgt      2820
```

```
tcttggtcct tccatcaatg gcttagcctc attgattcgg atgccttatg gctgtggtga    2880
acagaacatg ataaattttg ctccaaatat ttacattttg gattatctga ctaaaaagaa    2940
acaactgaca gataatttga agaaaaaagc tctttcattt atgaggcaag gttaccagag    3000
agaacttctc tatcagaggg aagatggctc tttcagtgct tttgggaatt atgacccttc    3060
tgggagcact tggttgtcag cttttgtttt aagatgtttc cttgaagccg atccttacat    3120
agatattgat cagaatgtgt tacacagaac atacacttgg cttaaaggac atcagaaatc    3180
caacggtgaa ttttgggatc caggaagagt gattcatagt gagcttcaag gtggcaataa    3240
aagtccagta acacttacag cctatattgt aacttctctc ctgggatata gaaagtatca    3300
gcctaacatt gatgtgcaag agtctatcca tttttttggag tctgaattca gtagaggaat    3360
ttcagacaat tatactctag cccttataac ttatgcattg tcatcagtgg ggagtcctaa    3420
agcgaaggaa gctttgaata tgctgacttg gagagcagaa caagaaggtg gcatgcaatt    3480
ctgggtgtca tcagagtcca aactttctga ctcctggcag ccacgctccc tggatattga    3540
agttgcagcc tatgcactgc tctcacactt cttacaattt cagacttctg agggaatccc    3600
aattatgagg tggctaagca ggcaaagaaa tagcttgggt ggttttgcat ctactcagga    3660
taccactgtg gctttaaagg ctctgtctga atttgcagcc ctaatgaata cagaaaggac    3720
aaatatccaa gtgaccgtga cggggcctag ctcaccaagt cctgtaaagt ttctgattga    3780
cacacacaac cgcttactcc ttcagacagc agagcttgct gtggtacagc caatggcagt    3840
taatatttcc gcaaatggtt ttggatttgc tatttgtcag ctcaatgttg tatataatgt    3900
gaaggcttct gggtcttcta aagacgaag atctatccaa aatcaagaag cctttgattt    3960
agatgttgct gtaaaagaaa ataaagatga tctcaatcat gtggatttga atgtgtgtac    4020
aagcttttcg ggcccgggta ggagtggcat ggctcttatg gaagttaacc tattaagtgg    4080
ctttatggtg ccttcagaag caatttctct gagcgagaca gtgaagaaag tggaatatga    4140
tcatggaaaa ctcaacctct atttagattc tgtaaatgaa acccagtttt gtgttaatat    4200
tcctgctgtg agaaacttta agtttcaaa tacccaagat gcttcagtgt ccatagtgga    4260
ttactatgag ccaaggagac aggcggtgag aagttacaac tctgaagtga agctgtcctc    4320
ctgtgacctt tgcagtgatg tccagggctg ccgtccttgt gaggatggag ct           4372
```

<210> SEQ ID NO 8
<211> LENGTH: 1420
<212> TYPE: PRT
<213> ORGANISM: Homo sapiens
<220> FEATURE:
<221> NAME/KEY: MISC_FEATURE
<222> LOCATION: (703)..(703)
<223> OTHER INFORMATION: Xaa = Ser or Tyr

<400> SEQUENCE: 8

```
Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
    50                  55                  60

Thr Ala Ser Asn Leu Thr Val Ser Val Leu Glu Ala Glu Gly Val Phe
65                  70                  75                  80
```

-continued

```
Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Asn Ile Thr Lys Thr Phe Lys Ile Asn Gly
        275                 280                 285

Ser Ala Asn Phe Ser Phe Asn Asp Glu Glu Met Lys Asn Val Met Asp
    290                 295                 300

Ser Ser Asn Gly Leu Ser Glu Tyr Leu Asp Leu Ser Ser Pro Gly Pro
305                 310                 315                 320

Val Glu Ile Leu Thr Thr Val Thr Glu Ser Val Thr Gly Ile Ser Arg
                325                 330                 335

Asn Val Ser Thr Asn Val Phe Phe Lys Gln His Asp Tyr Ile Ile Glu
            340                 345                 350

Phe Phe Asp Tyr Thr Thr Val Leu Lys Pro Ser Leu Asn Phe Thr Ala
        355                 360                 365

Thr Val Lys Val Thr Arg Ala Asp Gly Asn Gln Leu Thr Leu Glu Glu
    370                 375                 380

Arg Arg Asn Asn Val Val Ile Thr Val Thr Gln Arg Asn Tyr Thr Glu
385                 390                 395                 400

Tyr Trp Ser Gly Ser Asn Ser Gly Asn Gln Lys Met Glu Ala Val Gln
                405                 410                 415

Lys Ile Asn Tyr Thr Val Pro Gln Ser Gly Thr Phe Lys Ile Glu Phe
            420                 425                 430

Pro Ile Leu Glu Asp Ser Ser Glu Leu Gln Leu Lys Ala Tyr Phe Leu
        435                 440                 445

Gly Ser Lys Ser Ser Met Ala Val His Ser Leu Phe Lys Ser Pro Ser
    450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                485                 490                 495

Ser Tyr Met Val Val Ser Arg Gly Gln Leu Val Ala Val Gly Lys Gln
```

```
                500             505             510
Asn Ser Thr Met Phe Ser Leu Thr Pro Glu Asn Ser Trp Thr Pro Lys
            515                 520                 525
Ala Cys Val Ile Val Tyr Tyr Ile Glu Asp Asp Gly Glu Ile Ile Ser
            530                 535                 540
Asp Val Leu Lys Ile Pro Val Gln Leu Val Phe Lys Asn Lys Ile Lys
545                 550                 555                 560
Leu Tyr Trp Ser Lys Val Lys Ala Glu Pro Ser Glu Lys Val Ser Leu
                565                 570                 575
Arg Ile Ser Val Thr Gln Pro Asp Ser Ile Val Gly Ile Val Ala Val
            580                 585                 590
Asp Lys Ser Val Asn Leu Met Asn Ala Ser Asn Asp Ile Thr Met Glu
            595                 600                 605
Asn Val Val His Glu Leu Glu Leu Tyr Asn Thr Gly Tyr Tyr Leu Gly
            610                 615                 620
Met Phe Met Asn Ser Phe Ala Val Phe Gln Cys Gly Leu Trp Val
625                 630                 635                 640
Leu Thr Asp Ala Asn Leu Thr Lys Asp Tyr Ile Asp Gly Val Tyr Asp
                645                 650                 655
Asn Ala Glu Tyr Ala Glu Arg Phe Met Glu Glu Asn Glu Gly His Ile
                660                 665                 670
Val Asp Ile His Asp Phe Ser Leu Gly Ser Ser Pro His Val Arg Lys
            675                 680                 685
His Phe Pro Glu Thr Trp Ile Trp Leu Asp Thr Asn Met Gly Xaa Arg
            690                 695                 700
Ile Tyr Gln Glu Phe Glu Val Thr Val Pro Asp Ser Ile Thr Ser Trp
705                 710                 715                 720
Val Ala Thr Gly Phe Val Ile Ser Glu Asp Leu Gly Leu Gly Leu Thr
                725                 730                 735
Thr Thr Pro Val Glu Leu Gln Ala Phe Gln Pro Phe Phe Ile Phe Leu
            740                 745                 750
Asn Leu Pro Tyr Ser Val Ile Arg Gly Glu Glu Phe Ala Leu Glu Ile
            755                 760                 765
Thr Ile Phe Asn Tyr Leu Lys Asp Ala Thr Glu Val Lys Val Ile Ile
770                 775                 780
Glu Lys Ser Asp Lys Phe Asp Ile Leu Met Thr Ser Asn Glu Ile Asn
785                 790                 795                 800
Ala Thr Gly His Gln Gln Thr Leu Leu Val Pro Ser Glu Asp Gly Ala
                805                 810                 815
Thr Val Leu Phe Pro Ile Arg Pro Thr His Leu Gly Glu Ile Pro Ile
                820                 825                 830
Thr Val Thr Ala Leu Ser Pro Thr Ala Ser Asp Ala Val Thr Gln Met
            835                 840                 845
Ile Leu Val Lys Ala Glu Gly Ile Glu Lys Ser Tyr Ser Gln Ser Ile
            850                 855                 860
Leu Leu Asp Leu Thr Asp Asn Arg Leu Gln Ser Thr Leu Lys Thr Leu
865                 870                 875                 880
Ser Phe Ser Phe Pro Pro Asn Thr Val Thr Gly Ser Glu Arg Val Gln
                885                 890                 895
Ile Thr Ala Ile Gly Asp Val Leu Gly Pro Ser Ile Asn Gly Leu Ala
            900                 905                 910
Ser Leu Ile Arg Met Pro Tyr Gly Cys Gly Glu Gln Asn Met Ile Asn
            915                 920                 925
```

-continued

```
Phe Ala Pro Asn Ile Tyr Ile Leu Asp Tyr Leu Thr Lys Lys Gln
    930                 935                 940

Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
                965                 970                 975

Phe Gly Asn Tyr Asp Pro Ser Gly Ser Thr Trp Leu Ser Ala Phe Val
            980                 985                 990

Leu Arg Cys Phe Leu Glu Ala Asp Pro Tyr Ile Asp Ile Asp Gln Asn
        995                 1000                1005

Val Leu His Arg Thr Tyr Thr Trp Leu Lys Gly His Gln Lys Ser
    1010                1015                1020

Asn Gly Glu Phe Trp Asp Pro Gly Arg Val Ile His Ser Glu Leu
    1025                1030                1035

Gln Gly Gly Asn Lys Ser Pro Val Thr Leu Thr Ala Tyr Ile Val
    1040                1045                1050

Thr Ser Leu Leu Gly Tyr Arg Lys Tyr Gln Pro Asn Ile Asp Val
    1055                1060                1065

Gln Glu Ser Ile His Phe Leu Glu Ser Glu Phe Ser Arg Gly Ile
    1070                1075                1080

Ser Asp Asn Tyr Thr Leu Ala Leu Ile Thr Tyr Ala Leu Ser Ser
    1085                1090                1095

Val Gly Ser Pro Lys Ala Lys Glu Ala Leu Asn Met Leu Thr Trp
    1100                1105                1110

Arg Ala Glu Gln Glu Gly Gly Met Gln Phe Trp Val Ser Ser Glu
    1115                1120                1125

Ser Lys Leu Ser Asp Ser Trp Gln Pro Arg Ser Leu Asp Ile Glu
    1130                1135                1140

Val Ala Ala Tyr Ala Leu Leu Ser His Phe Leu Gln Phe Gln Thr
    1145                1150                1155

Ser Glu Gly Ile Pro Ile Met Arg Trp Leu Ser Arg Gln Arg Asn
    1160                1165                1170

Ser Leu Gly Gly Phe Ala Ser Thr Gln Asp Thr Thr Val Ala Leu
    1175                1180                1185

Lys Ala Leu Ser Glu Phe Ala Ala Leu Met Asn Thr Glu Arg Thr
    1190                1195                1200

Asn Ile Gln Val Thr Val Thr Gly Pro Ser Ser Pro Ser Pro Val
    1205                1210                1215

Lys Phe Leu Ile Asp Thr His Asn Arg Leu Leu Leu Gln Thr Ala
    1220                1225                1230

Glu Leu Ala Val Val Gln Pro Met Ala Val Asn Ile Ser Ala Asn
    1235                1240                1245

Gly Phe Gly Phe Ala Ile Cys Gln Leu Asn Val Val Tyr Asn Val
    1250                1255                1260

Lys Ala Ser Gly Ser Ser Arg Arg Arg Ser Ile Gln Asn Gln
    1265                1270                1275

Glu Ala Phe Asp Leu Asp Val Ala Val Lys Glu Asn Lys Asp Asp
    1280                1285                1290

Leu Asn His Val Asp Leu Asn Val Cys Thr Ser Phe Ser Gly Pro
    1295                1300                1305

Gly Arg Ser Gly Met Ala Leu Met Glu Val Asn Leu Leu Ser Gly
    1310                1315                1320
```

```
Phe Met Val Pro Ser Glu Ala Ile Ser Leu Ser Glu Thr Val Lys
    1325                1330                1335

Lys Val Glu Tyr Asp His Gly Lys Leu Asn Leu Tyr Leu Asp Ser
    1340                1345                1350

Val Asn Glu Thr Gln Phe Cys Val Asn Ile Pro Ala Val Arg Asn
    1355                1360                1365

Phe Lys Val Ser Asn Thr Gln Asp Ala Ser Val Ser Ile Val Asp
    1370                1375                1380

Tyr Tyr Glu Pro Arg Arg Gln Ala Val Arg Ser Tyr Asn Ser Glu
    1385                1390                1395

Val Lys Leu Ser Ser Cys Asp Leu Cys Ser Asp Val Gln Gly Cys
    1400                1405                1410

Arg Pro Cys Glu Asp Gly Ala
    1415                1420

<210> SEQ ID NO 9
<211> LENGTH: 99
<212> TYPE: DNA
<213> ORGANISM: Homo sapiens

<400> SEQUENCE: 9
attgatggtg tttatgacaa tgcagaatat gctgagaggt ttatggagga aaatgaagga      60
catattgtag atattcatga cttttctttg ggtagcagt                             99

<210> SEQ ID NO 10
<211> LENGTH: 33
<212> TYPE: PRT
<213> ORGANISM: homo sapiens

<400> SEQUENCE: 10

Ile Asp Gly Val Tyr Asp Asn Ala Glu Tyr Ala Glu Arg Phe Met Glu
1               5                   10                  15

Glu Asn Glu Gly His Ile Val Asp Ile His Asp Phe Ser Leu Gly Ser
            20                  25                  30

Ser

<210> SEQ ID NO 11
<211> LENGTH: 57
<212> TYPE: DNA
<213> ORGANISM: Homo sapiens
<220> FEATURE:
<221> NAME/KEY: misc_feature
<222> LOCATION: (29)..(29)
<223> OTHER INFORMATION: N = A or C

<400> SEQUENCE: 11
tggatttggc tagacaccaa catgggttnc aggatttacc aagaatttga agtaact         57

<210> SEQ ID NO 12
<211> LENGTH: 19
<212> TYPE: PRT
<213> ORGANISM: homo sapiens
<220> FEATURE:
<221> NAME/KEY: MISC_FEATURE
<222> LOCATION: (10)..(10)
<223> OTHER INFORMATION: Xaa = Ser or Tyr
```

```
<400> SEQUENCE: 12

Trp Ile Trp Leu Asp Thr Asn Met Gly Xaa Arg Ile Tyr Gln Glu Phe
1               5                   10                  15

Glu Val Thr
1/38
```

What is claimed is:

1. A method for inhibiting TGF-β1 activity in a biological tissue of an animal comprising an administration thereto of an effective amount of a protein comprising a sequence selected from the group consisting of:

a) SEQ ID NO:2 b) amino acids 694–712 of SEQ ID NO:2;

c) amino acids 651–683 of SEQ ID NO:2 d) a protein sequence having a tyrosine at position 703 of SEQ ID NO:2;

e) a protein sequence having amino acids 21 to 1428 of SEQ ID NO:2 f) a protein sequence having amino acids 21 to 1404 of SEQ ID NO:2; and g) a protein sequence having a methionine instead of threonine at position 1224 of SEQ ID NO:2 thereby inhibiting TGF-β1 activity in a biological tissue of an animal.

2. The method of claim 1, wherein said protein has the amino acid sequence of SEQ ID NO:2.

* * * * *